US011427591B2

(12) United States Patent
Aliper et al.

(10) Patent No.: US 11,427,591 B2
(45) Date of Patent: Aug. 30, 2022

(54) KINASE INHIBITORS

(71) Applicant: Insilico Medicine IP Limited, Hong Kong (HK)

(72) Inventors: Aleksandr M. Aliper, Moscow (RU); Yan Ivanenkov, Moscow (RU); Daniil Polykovskiy, Moscow (RU); Victor Terentiev, Moscow (RU); Aleksandrs Zavoronkovs, Pak Shek Kok (HK)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

(21) Appl. No.: 16/656,047

(22) Filed: Oct. 17, 2019

(65) Prior Publication Data

US 2020/0123165 A1 Apr. 23, 2020

Related U.S. Application Data

(60) Provisional application No. 62/746,771, filed on Oct. 17, 2018.

(51) Int. Cl.

| | |
|---|---|
| ***C07D 487/04*** | (2006.01) |
| ***C07D 413/06*** | (2006.01) |
| ***C07D 413/14*** | (2006.01) |
| ***C07D 498/04*** | (2006.01) |
| ***C07D 491/048*** | (2006.01) |
| ***C07D 491/04*** | (2006.01) |
| ***C07D 471/04*** | (2006.01) |

(52) U.S. Cl.

CPC ......... *C07D 487/04* (2013.01); *C07D 413/06* (2013.01); *C07D 413/14* (2013.01); *C07D 471/04* (2013.01); *C07D 491/04* (2013.01); *C07D 491/048* (2013.01); *C07D 498/04* (2013.01)

(58) Field of Classification Search

CPC .. C07D 487/04; C07D 413/06; C07D 413/14; C07D 498/04; C07D 491/048

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,544,545 | A | 10/1985 | Ryan et al. | |
| 5,013,556 | A | 5/1991 | Woodle et al. | |
| 6,677,368 | B2 * | 1/2004 | Cui | C07D 209/34 514/427 |
| 8,044,259 | B2 | 10/2011 | Clarke et al. | |
| 8,114,874 | B2 | 2/2012 | Zou et al. | |
| 8,115,014 | B2 * | 2/2012 | Ohmoto | A61P 43/00 548/491 |
| 9,815,811 | B2 * | 11/2017 | Banerjee | A61K 31/4436 |
| 2002/0156081 | A1 | 10/2002 | Hirst et al. | |
| 2009/0042820 | A1 * | 2/2009 | Matteucci | C07D 403/14 514/43 |

FOREIGN PATENT DOCUMENTS

| | | | |
|---|---|---|---|
| WO | WO2006057946 | A2 | 6/2006 |
| WO | WO2014186035 | A1 | 11/2014 |
| WO | WO2016096709 | A1 | 6/2016 |
| WO | WO-2020079652 | A1 | 4/2020 |

OTHER PUBLICATIONS

Yanagi et al., Organic & Biomolecular Chemistry (Jan. 2018), 16(9), 1496-1507. (Year: 2018).*

Corr et al., Chemical Science (2017), 8(3), 2039-2046. (Year: 2017).*

International Search Report issued in PCT/IB2019/058885 dated Jan. 23, 2020.

Written Opinion issued in PCT/IB2019/058885 dated Jan. 23, 2020.

Liao, Y. et al. "Palladium(II)-Mediated Cascade Carbonylative Annulation of o-Alkynyl-phenols on Silyl Linker-Based Macrobeads: A Combinatorial Synthesis of a 2,3-Disubstituted Benzo[b]furan Library". Organic Letters. 22 Jwr.2002 (Jun. 22, 2002) No. 15 vol. 4 pp. 2607-2609.

Bambuch, V. et al. C-Functionalization of 9-deazapurines by cross-coupling reactions. Tetrahedron. vol. 63, Issue 7, Feb. 12, 2007, pp. 1589-1601.

(Continued)

*Primary Examiner* — Laura L Stockton

(74) *Attorney, Agent, or Firm* — Wilson Sonsini Goodrich & Rosati

(57) ABSTRACT

A DDR1 inhibitor compound can have a structure of Formula A, derivative thereof, prodrug thereof, salt thereof, stereoisomer thereof, tautomer thereof, polymorph thereof, or solvate thereof, or having any chirality at any chiral center, Formula A

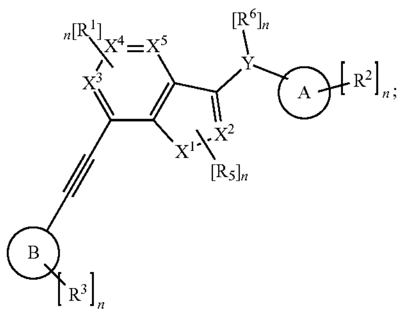

ring A is a ring structure; ring B is a ring structure; the $X^1$, $X^2$, $X^3$, $X^4$, and $X^5$ are each independently a carbon or a hetero atom with or without a substituent; the Y is a linker; and each $R^1$, $R^2$, $R^3$, $R^5$, and $R^6$ is independently a substituent; and each n is an integer, such as from 0 to the maximum number of allowed substituents on the linker or ring, wherein $R^5$ and/or $R^6$ is optionally nothing.

14 Claims, 19 Drawing Sheets

(56) References Cited

OTHER PUBLICATIONS

Eppstein, et al. Biological activity of liposome-encapsulated murine interferon gamma is mediated by a cell membrane receptor. Proc Natl Acad Sci USA. Jun. 1985; 82(11): 3688-3692. doi: 10.1073/pnas.82.11.3688.
Hwang, et al. Hepatic uptake and degradation of unilamellar sphingomyelin/cholesterol liposomes: A kinetic study. Proc Natl Acad Sci USA. Jul. 1980;77(7):4030-4034. doi: 10.1073/pnas.77.7.4030.
Liao, et al. Palladium(II)-mediated cascade carbonylative annulation of o-alkynyl-phenols on silyl linker-based macrobeads: a combinatorial synthesis of a 2,3-disubstituted benzo[b]furan library. Org Lett. Jul. 25, 2002;4(15):2607-2609. doi: 10.1021/ol020111y.

* cited by examiner

Compound 1

Scheme 1

Product 1-1

Product 1-2

Product 1-3

Product 1-4

Formula A

Formula B

Compound 115

Scheme 1A

Compound 118

Compound 119

Scheme 1C

Scheme 2

Product 2-3

Product 2-4C

Compound 111

Scheme 2C

Product 2-3

Product 2-4D

Compound 112

Scheme 2D

Product 2-3

Step 2-4E

Step 2-5E

Compound 113

Scheme 2E

Step A-1

Product A-1

Step A-2

Compound 114

Scheme A

Product B-1

Product B-2

Product B-3

Compound 116

Scheme B

Scheme C

Product 2-2

Product 3-1

Compound 120

Scheme 3

Step 2-2

Product 2-2

Step 3-1A

Product 3-1A

Step 3-2

Compound 121

Scheme 3A

Scheme 4

KINASE INHIBITORS

CROSS-REFERENCE

This patent application claims priority to U.S. Provisional Application No. 62/746,771 filed Oct. 17, 2018, which provisional is incorporated herein by specific reference in its entirety.

BACKGROUND

Field

The present disclosure relates to compounds and/or pharmaceutical compositions for use as inhibitors of a receptor tyrosine kinase as well as methods of synthesis and use of the same. More particularly, the compounds can be used for inhibiting a discoidin domain receptor, such as DDR1, or others.

Description of Related Art

A biologically active receptor known as the discoidin domain receptor family, member 1 (hereinafter "DDR1") is involved in various biological processes, such as being a receptor tyrosine kinase that facilitates communication of cells. DDR1 is a cell surface receptor for fibrillar collagen, and regulates cell attachment to the extracellular matrix, and remodeling the extracellular matrix. DDR1 is involved in regulation of cell growth, differentiation, cell migration, proliferation, and metabolism, and can be found in epithelial cells, such as the kidney, lung, gastrointestinal tract, and brain. DDR1 collagen binding triggers a signaling pathway that involves SRC (non-receptor tyrosine kinase) and leads to the activation of MAP kinases. DDR1 also regulates remodeling of the extracellular matrix by up-regulation of the matrix metalloproteinases MMP2, MMP7 and MMP9, and thereby facilitates cell migration and wound healing. It is thought that DDR1 may be required for normal blastocyst implantation during pregnancy, for normal mammary gland differentiation and normal lactation. Also, normal DDR1 production has been linked to normal ear morphology and normal hearing (by similarity). DDR1 also promotes smooth muscle cell migration, and thereby contributes to arterial wound healing.

However, DDR1 is significantly over-expressed in some human tumors, such as breast, ovarian, esophageal, and pediatric brain, and may play a role in tumor cell invasion. As a result, DDR1 inhibitors are desirable in order to inhibit the adverse activity of DDR1, and may be useful in cancer therapy.

Accordingly, it would be advantageous to have a DDR1 inhibitor that can inhibit DDR1 activity. It would also be advantageous to have a specific DDR1 inhibitor that selectively inhibits DDR1. Additionally, it would be advantageous to have a broad spectrum kinase inhibitor that inhibits a broad spectrum of kinases.

SUMMARY

In some embodiments, a compound that is a kinase inhibitor can have a structure of Formula A, derivative thereof, prodrug thereof, salt thereof, stereoisomer thereof, tautomer thereof, polymorph thereof, or solvate thereof, or having any chirality at any chiral center, Formula A

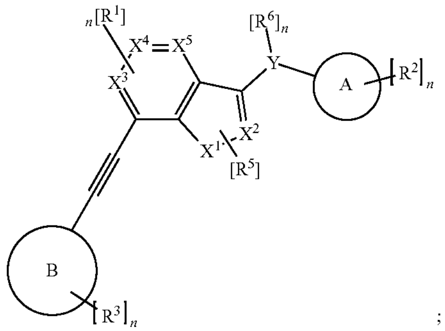

;

wherein: ring A is a ring structure; ring B is a ring structure; the $X^1$, $X^2$, $X^3$, $X^4$, and $X^5$ are each independently a carbon or a hetero atom with or without a substituent; the Y is a linker; and each $R^1$, $R^2$, $R^3$, $R^5$, and $R^6$ is independently at least one R group substituent, wherein $R^5$ and/or $R^6$ is optionally nothing, and each n is an integer and defines the number of R group substituents.

In some embodiments, ring A is a cycloaliphatic, hetero cycloaliphatic, aryl, hetero aryl, polyaryl, poly hetero aryl, or combinations thereof; ring B is a cycloaliphatic, hetero cycloaliphatic, aryl, hetero aryl, polyaryl, poly hetero aryl, or combinations thereof; X' is $CH_2$, NH, O, or S; $X^2$, $X^3$, $X^4$, and $X^5$ are each independently CH or N; Y is selected from O, S, C, N, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, any substituted or unsubstituted, or combinations thereof; and $R^1$, $R^2$, $R^3$, $R^5$, and $R^6$ are each at least one substituent that are each independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, any substituted or unsubstituted, or combinations thereof, wherein $R^5$ and/or $R^6$ is optionally nothing.

In some embodiments, ring A is a cycloaliphatic with 5-24 ring atoms, hetero cycloaliphatic with 5-24 ring atoms, aryl with 5-24 ring atoms, hetero aryl with 5-24 ring atoms, polyaryl with 5-24 ring atoms, poly hetero aryl with 5-24 ring atoms, or combinations thereof; ring B is a cycloaliphatic with 5-24 ring atoms, hetero cycloaliphatic with 5-24 ring atoms, aryl with 5-24 ring atoms, hetero aryl with 5-24 ring atoms, polyaryl with 5-24 ring atoms, poly hetero aryl with 5-24 ring atoms, or combinations thereof; $X^1$ is O; $X^2$ $X^3$, $X^4$, and $X^5$ are each independently CH or N; Y is selected from O, S, C, N, straight aliphatics with 1-24 chain atoms, branched aliphatics with 1-24 chain atoms, cyclic aliphatics with 5-20 ring atoms, substituted aliphatics with 1-24 chain atoms and/or 5-20 ring atoms, unsubstituted aliphatics with 1-24 chain atoms and/or 5-20 ring atoms, saturated aliphatics with 1-24 chain atoms and/or 5-20 ring atoms, unsaturated aliphatics with 1-24 chain atoms and/or 5-20 ring atoms, aromatics with 5-20 ring atoms, polyaromatics with 5-20 ring atoms, substituted aromatics with 5-20 ring atoms, hetero-aromatics with 5-20 ring atoms, substituted hetero-aromatics with 5-20 ring atoms, amines, primary amines, secondary amines, tertiary amines, aliphatic amines with 1-24 chain atoms and/or 5-20 ring atoms, carbonyls, carboxyls, amides, esters, amino acids, derivatives thereof, any substituted or unsubstituted, or combinations thereof; and each substituent of each $R^1$, $R^2$, $R^3$, $R^5$, and $R^6$ are each independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkyl sulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any being substituted, derivatives thereof, and combinations thereof, wherein $R^5$ and/or $R^6$ is optionally nothing.

In some embodiments, ring A is a cycloaliphatic with 5-12 ring atoms, hetero cycloaliphatic with 5-12 ring atoms, aryl with 5-12 ring atoms, hetero aryl with 5-12 ring atoms, polyaryl with 5-12 ring atoms, poly hetero aryl with 5-12 ring atoms, or combinations thereof; ring B is a cycloaliphatic with 5-12 ring atoms, hetero cycloaliphatic with 5-12 ring atoms, aryl with 5-12 ring atoms, hetero aryl with 5-12 ring atoms, polyaryl with 5-12 ring atoms, poly hetero aryl with 5-12 ring atoms, or combinations thereof; $X^1$ is O; $X^2$ $X^3$, $X^4$, and $X^5$ are each independently CH or N; Y is selected from O, S, C, N, straight aliphatics with 1-12 chain atoms, branched aliphatics with 1-12 chain atoms, cyclic aliphatics with 5-12 ring atoms, substituted aliphatics with 1-12 chain atoms and/or 5-12 ring atoms, unsubstituted aliphatics with 1-12 chain atoms and/or 5-12 ring atoms, saturated aliphatics with 1-12 chain atoms and/or 5-12 ring atoms, unsaturated aliphatics with 1-12 chain atoms and/or 5-12 ring atoms, aromatics with 5-12 ring atoms, hetero aromatics with 5-12 ring atoms, polyaromatics with 5-12 ring atoms, substituted aromatics with 5-12 ring atoms, hetero-aromatics with 5-12 ring atoms, amines, primary amines, secondary amines, tertiary amines, aliphatic amines with 1-12 chain atoms and/or 5-12 ring atoms, carbonyls, carboxyls, amides, esters, amino acids, derivatives thereof, substituted or unsubstituted, or combinations thereof; and the one or more substituents of each of $R^1$, $R^2$, $R^3$, $R^5$, and $R^6$ are each independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, any with or without hetero atoms, any substituted or unsubstituted, derivatives thereof, and combinations thereof, wherein $R^5$ and/or $R^6$ is optionally nothing. Accordingly, each shown R group substituent can be one or more substituents, and the number of substituents is defined by the available atoms of the structure for having a substituent.

In some embodiments, a pharmaceutical composition can include: the compound of one of the embodiments; and a pharmaceutically acceptable carrier having the compound.

In some embodiments, a method of inhibiting a kinase can include: providing the compound of one of the embodiments described herein to the kinase such that the kinase is inhibited. In some aspects, a method of inhibiting a kinase in a subject, such as DDR1, can include: administering the compound of one of the embodiments to a subject. In some aspects, the administering includes a therapeutically effective amount of the compound sufficient to treat cancer by: inhibiting cancer cell growth; inhibiting cancer cell migration; inhibiting cancer cell proliferation; or inhibiting cancer cell migration.

In some embodiments, a method of inhibiting cellular communication can include providing the compound of one of the embodiments to a cell so as to inhibit communication of the cell with a surrounding environment of the cell.

In some embodiments, a method of inhibiting a cell attachment to an extracellular matrix can include: providing the compound of one of the embodiments to a DDR1 receptor of the cell to inhibit the DDR1 receptor from interacting with fibrillar collagen.

In some embodiments, a method of inhibiting cell activity can include: providing the compound of one of the embodiments to a cell so as to inhibit at least one biological function of the cell.

In some embodiments, a method of promoting remodeling of an extracellular matrix can include: providing the compound of one of the embodiments to a DDR1 receptor so as to cause upregulation of a matrix metalloproteinase.

In some embodiments, a method of inhibiting blastocyte implantation during pregnancy can include: providing the compound of one of the embodiments to a DDR1 receptor of an undifferentiated cell in a blastula stage of an embryo.

In some embodiments, a method of inhibiting mammary gland differentiation can include: providing the compound of one of the embodiments to a DDR1 receptor of a mammary gland so as to inhibit differentiation of cells of the mammary gland.

In some embodiments, a method of inhibiting activity of a cancer cell can include: administering the compound of one of the embodiments to the cancer cell so as to inhibit a biological activity of the cancer cell.

In some embodiments, a method of treating cancer in a subject can include:

administering the compound of one of the embodiments to a subject that has cancer.

In some embodiments, a method of synthesizing the compound of Formula A can include performing at least one synthesis step with at least two reactants that react to form the compound having a structure of Formula A, derivative thereof, prodrug thereof, salt thereof, stereoisomer thereof, tautomer thereof, polymorph thereof, or solvate thereof, or having any chirality at any chiral center. In some aspects, the method can include: obtaining a reactant A that includes the ring A; and obtaining a reactant B that includes the ring B. In some aspects, the method can include: obtaining a first reactant having a ring structure; and reacting a second reactant with the first reactant to form a polycylic structure, the polycyclic structure having variables $X^1$, $X^2$, $X^3$, $X^4$, and $X^5$.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
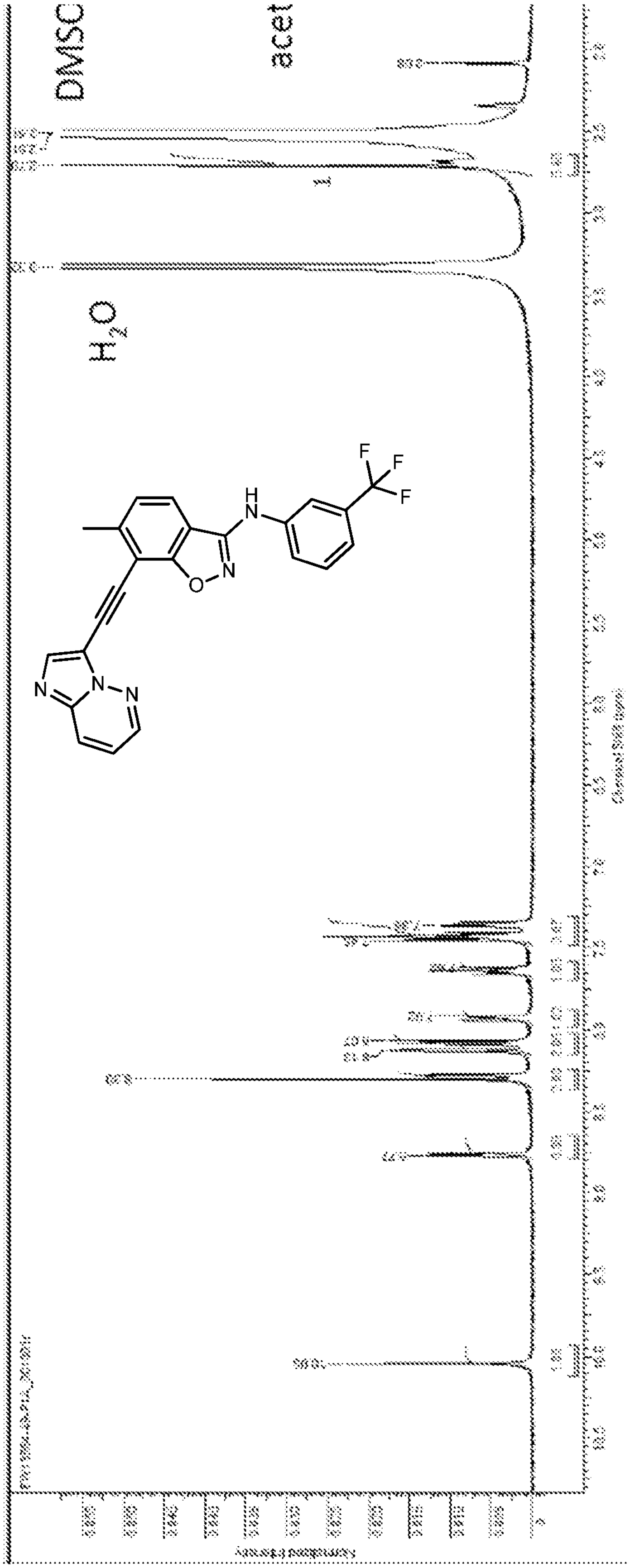
FIG. 1 shows a structure of a DDR1 inhibitor and NMR spectra.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting.

Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to at least one molecule that functions as a kinase inhibitor, such as a DDR1 inhibitor. As such, the molecules described herein can be used in methods related to inhibiting any kinase, such as DDR1, so as to inhibit the kinase (e.g., DDR1) biological activity. As a result, the molecules can be used in therapeutic methods where inhibiting a kinase, such as DDR1, can provide a therapy to a subject that is administered the molecule. Thus, the molecules described herein can each be referred to as a kinase inhibitor, where some are broad spectrum inhibitors of many kinases, and some are specific inhibitors that inhibit a specific kinase, such as DDR1 inhibitor.

Accordingly, the kinase (e.g., DDR1) inhibitors can be used to inhibit a receptor tyrosine kinase that facilitates communication of cells so as to inhibit such communication of cells. In some aspects, the DDR1 inhibitor can inhibit binding of the DDR1 receptor a cell surface receptor so as to inhibit binding with fibrillar collagen, and thereby can inhibit biological activity related to regulation of cell attachment to the extracellular matrix, and regulation of remodeling the extracellular matrix. The DDR1 inhibitor can inhibit regulation of cell growth, differentiation, cell migration, proliferation, and metabolism. Accordingly, the inhibitor compounds can be used to treat fibrosis. As such, the inhibitor compounds can be used to inhibit formation of excess fibrous connective tissue in an organ or tissue. The inhibitor compounds can inhibit scarring linked to fibrosis, such as by inhibition of accumulation of extracellular matrix proteins that inhibits thickening (e.g., scarring) of the affected tissue. This also allows for the inhibitor compounds to inhibit exaggerated or excessive wound healing and allow normal organ function.

In some embodiments, a method of inhibiting fibrosis can include providing the compound of claim 1 to a DDR1 receptor to inhibit formation of excess fibrous tissue. In some aspects, the DDR1 receptor is associated with a tissue or organ, and thereby inhibition inhibits fibrosis in the tissue or organ. In some aspects, the tissue is associated with a liver or lung, or the organ is the liver or the lung. In some aspects, the DDR1 receptor is associated with pulmonary fibrosis, cystic fibrosis, idiopathic pulmonary fibrosis (IPF), radiation-induced lung injury, bridging fibrosis, cirrhosis, non-alcoholic hepatosteatosis (NASH), non-alcoholic fatty liver disease (NAFLD), atrial fibrosis, endomyocardial fibrosis, myocardial infarction related fibrosis, glial scar, arterial stiffness, arthrofibrosis, crohn's disease, dupuytren contracture, keloid, mediastinal fibrosis, myelofibrosis, Peyronie's disease, nephrogenic systemic fibrosis, progressive massive fibrosis, retroperitoneal fibrosis, scleroderma sclerosis, or combinations thereof. Thus, the inhibitor compounds can treat this indications of fibrosis.

The DDR1 inhibitor can be applied to cells to be an antagonist or inhibitor of the DDR1 receptor. As such, the DDR1 inhibitor can be applied to epithelial cells, such as the kidney, lung, gastrointestinal tract, and brain so as to inhibit the DDR1 receptor on these cells. The DDR1 inhibitor can inhibit collagen binding to the DDR1 receptor, and thereby inhibit a signaling pathway that involves SRC (non-receptor tyrosine kinase). This can inhibit the activation of MAP kinases.

The DDR1 inhibitor can be used to inhibit DDR1 that is over-expressed in some human tumors, such as breast, ovarian, esophageal, and pediatric brain. As such, the DDR1 may be used in cancer therapy. The activity of the DDR1 inhibitor may also inhibit tumor cell invasion. As a result, the DDR1 inhibitor can inhibit the adverse activity of DDR1, and may be useful in cancer therapy.

In some embodiments, the invention provides agents (e.g., DDR1 inhibitors) which bind to and/or modulate the activity of DDR1. The DDR1 inhibitors can be included in compositions, such as pharmaceutical compositions for administration. In certain embodiments, the DDR1 inhibitors can specifically bind to DDR1 (e.g., human DDR1). In certain embodiments, the DDR1 inhibitors that specifically bind to and/or modulate the activity of DDR1 may further specifically bind to and/or modulate the activity of the discoidin domain receptor 2 (DDR2) or other kinases.

The invention further provides methods of targeting cancer cells with the DDR1 inhibitors. In certain embodiments, the methods comprise reducing the frequency of cancer cells or cancer stem cells in a tumor, reducing the number of cancer cells or cancer stem cells in a tumor, reducing the tumorigenicity of a tumor, and/or reducing the tumorigenicity of a tumor by reducing the number or frequency of cancer cells or cancer stem cells in the tumor. The invention also provides methods of using the DDR1 inhibitors in the treatment of cancer and/or in the inhibition of the growth of tumors. In one aspect, the invention provides a method of inhibiting the growth of a tumor in a subject, comprising administering to the subject a therapeutically effective amount of one or more DDR1 inhibitors that modulate the activity of DDR1. In certain embodiments of each of the aforementioned aspects, as well as other aspects described elsewhere herein, the tumors which are targeted are breast, colorectal, hepatic, renal, lung, pancreatic, bile duct, ovarian, prostate, or head and neck tumors. The broad spectrum kinase inhibitors may also be used to treat and/or inhibit cancer.

The present invention further provides methods of treating cancer in a subject. In some embodiments, the method comprises administering to a subject a therapeutically effective amount of any of the kinase (e.g., DDR1) inhibitors described herein. In some embodiments, the cancer to be treated is breast cancer, colorectal cancer, hepatic cancer, kidney cancer, liver cancer, lung cancer, pancreatic cancer, gastrointestinal cancer, melanoma, ovarian cancer, prostate cancer, cervical cancer, bile duct cancer, microsatellite instability-high (MSI-H) cancer, bladder cancer, glioblastoma, and head and neck cancer. In some embodiments, the methods further comprise administering to the subject at least one additional anti-cancer agent along with the kinase (e.g., DDR1) inhibitor.

In some embodiments, the invention provides a method of inhibiting the growth of a tumor in a subject, comprising administering to the subject a therapeutically effective amount of a kinase (e.g., DDR1) inhibitor that modulates the activity of the kinase (e.g., DDR1). In certain embodiments, the kinase (e.g., DDR1) inhibitors reduces tumorigenicity of the tumor by reducing the number or frequency of cancer stem cells in the tumor. In certain embodiments, the kinase (e.g., DDR1) inhibitor is Compound 1 that specifically binds to DDR1. In certain embodiments, the tumor is selected from the group consisting of a breast tumor, colorectal tumor, hepatic tumor, renal tumor, lung tumor, pancreatic tumor, ovarian tumor, prostate tumor, and head and neck tumor. In certain embodiments, the tumor expresses LGR5. In certain embodiments, the tumor expresses LGR5 and the tumor is a colorectal tumor, hepatic tumor, ovarian tumor, or pancreatic tumor. In certain embodiments, the cancer stem cells express LGR5. In certain embodiments, the cancer stem cells express LGR5 and the tumor is a colorectal tumor, hepatic tumor, ovarian tumor, or pancreatic tumor. In certain embodiments, the tumor expresses Hes1. In certain embodiments, the tumor expresses Hes1 and the tumor is a breast tumor, colorectal tumor, renal tumor, lung tumor, pancreatic tumor, or prostate tumor. In certain embodiments, the cancer stem cells express Hes1. In certain embodiments, the cancer stem cells express Hes1 and the tumor is a breast tumor, colorectal tumor, renal tumor, lung tumor, pancreatic tumor, or prostate tumor. In certain embodiments, the subject is a human. The other methods may also include the foregoing by inhibiting DDR1 with the DDR1 inhibitor.

In some embodiments, the invention provides a DDR1 inhibitor that modulates the activity of DDR1. In certain embodiments, the DDR1 inhibitors specifically binds to DDR1. In some embodiments, the DDR1 inhibitor binds the extracellular domain of DDR1. In certain embodiments, the DDR1 inhibitor binds the discoidin domain of DDR1.

In certain embodiments, the DDR1 inhibitor is an antagonist of DDR1. In some embodiments, the term "antagonist" includes any molecule that partially or fully blocks, inhibits, or neutralizes a biological activity of a DDR1 and/or DDR2 protein or fragment thereof. In some embodiments, the term "antagonist" includes any molecule that partially or fully blocks, inhibits, or neutralizes the expression of DDR1, and/or DDR2 protein or fragment thereof.

In certain embodiments, the DDR1 inhibitor does not have one or more effector functions. For instance, in some embodiments, the DDR1 inhibitors has minimal or no cellular cytotoxicity activity. In certain embodiments, the DDR1 inhibitor does not bind to an Fc receptor and/or complement factors. In certain embodiments, the DDR1 inhibitor has no effector function.

In certain embodiments, the treatment methods further comprise administering at least one additional therapeutic agent appropriate for effecting combination therapy (e.g., a chemotherapeutic agent or other anticancer agent if cancer is to be treated) in addition to the DDR1 inhibitors described herein. In certain embodiments, the additional therapeutic agent is irinotecan or gemcitabine. In certain embodiments, the additional therapeutic agent is irinotecan. In certain embodiments, the additional therapeutic agent is gemcitabine.

In certain embodiments, the compounds of the formulae provided herein can be used for cancer therapy and be administered to a subject that has a cancerous growth. The compounds can be used to inhibit tumor growth, or otherwise inhibit any neoplasm. The compounds may also be used to inhibit cancer metastasis. As such, the compounds can be tumorigenic.

In some aspects, the compounds can be used to treat cancer that may include a cancer stem cell or solid tumor stem cell. In some aspects, a tumor may be assayed to determine whether or not a cancer stem cell is present prior to the therapy with the compound. For example, stem cell cancer markers may be used to identify the presence of a cancer stem cell.

In some instances, a biopsy and diagnostic protocol can be performed to identify a cancer prior to the therapy with the compound.

In some embodiments, the compounds can be broad spectrum kinase inhibitors. In some aspects, the compounds can be receptor tyrosine kinase (RTK) inhibitors. Accordingly, the compounds can inhibit kinases from the following RTK families: RTK class I (EGF receptor family) (ErbB family); RTK class II (Insulin receptor family); RTK class III (PDGF receptor family); RTK class IV (VEGF receptors family); RTK class V (FGF receptor family); RTK class VI (CCK receptor family); RTK class VII (NGF receptor family); RTK class VIII (HGF receptor family); RTK class IX (Eph receptor family); RTK class X (AXL receptor family); RTK class XI (TIE receptor family); RTK class XII (RYK receptor family); RTK class XIII (DDR receptor family); RTK class XIV (RET receptor family); RTK class XV (ROS receptor family); RTK class XVI (LTK receptor family); RTK class XVII (ROR receptor family); RTK class XVIII (MuSK receptor family); RTK class XIX (LMR receptor); and/or RTK class XX (Undetermined).

In some embodiments, the DDR1 inhibitor has a structure of Formula A or Formula B or Formula C or Formula D or Formula E or Formula F or Formula G or Formula H, derivative thereof, prodrug thereof, salt thereof, or stereoisomer thereof, or having any chirality at any chiral center, or tautomer, polymorph, solvate, or combination thereof, as presented herein. In some instances, the compounds can be pharmaceutically acceptable salts. As in these formulae, the R substituent groups can be any substituents. For example, the R substituent groups can be one or more of the substituents recited herein or combinations thereof.

Formula A

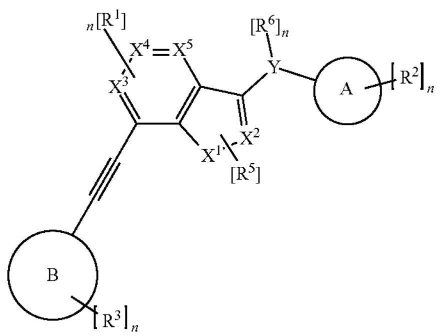

In Formula A, rings A and B can be any ring structure with a single ring or two or more fused rings, which can be cycloaliphatic, hetero cycloaliphatic, aryl, hetero aryl, polyaryl, poly hetero aryl, or combinations thereof with 4, 5, 6, 7, 8, 9, 10, 11, or 12 atoms. When including hetero atoms, they can be C, O, N, or S and depend on the number of bonds therewith, and any ring A or B can include 1, 2, 3, 4, 5, 6 or more hetero atoms. Rings A and B can be substituted with one or more R groups, shown as $R^2$ and $R^3$, where each shown R group can be at least one R group substituent, and each R group substituent can be independently any of the R group substituents provided herein. The number of R group substituents for rings A and B are determined by the number of atoms in the ring when single rings being n−1 where n is the number of ring atoms. Each R group substituent on a ring can be different from the others.

In Formula A, the X ring atoms can be carbon (C) or a hetero atom, such as O, N, or S, or other. As noted, when carbon, the X ring atom may or may not have a substituent, such as shown by as $R^2$, $R^3$, and $R^5$, which can be on any atom of the respective ring, such as on the X ring atom, if present, such as in $X^1$, $X^2$, $X^3$, $X^4$, and $X^5$. As such, $X^1$ can be a C (e.g., $CH_2$) or O or N (e.g., NH) or S, with the appropriate hydrogen atoms. The $X^2$ can be a C (e.g., CH) or N, with the appropriate hydrogen atoms. The $X^3$ can be a C (e.g., CH) or N, with the appropriate hydrogen atoms. The $X^4$ can be a C (e.g., CH) or N, with the appropriate hydrogen atoms. The $X^5$ can be a C (e.g., CH) or N, with the appropriate hydrogen atoms. When the X ring atom has two bonds it can be C, O, N, or S, when 3 bonds it can be as C, or N. When Y is an O or S, $R^6$ is nothing. When one or more of $X^3$, $X^4$, and $X^5$ is carbon, $R^1$ is a substituent as defied herein on each carbon. When $X^3$, $X^4$, and $X^5$ is nitrogen, $R^1$ is a nothing or electrons as described herein. In some aspects, only one of $X^3$, $X^4$, or $X^5$ is a hetero atom. In some aspects, only two of $X^3$, $X^4$, or $X^5$ is a hetero atom, which may be adjacent or separated.

In Formula A, the Y can be any linker. When Y is one chain atom or more than one chain atom, there may be a $R^6$ on one or more of the chain atoms. The linker can be O, S, C, N, or a hydrocarbon chain with or without hetero atoms, such as those recited herein for the X ring atoms. The linker may include O, S, C, N, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, substituted or unsubstituted, or combinations. In some aspects, the liker can include $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any substituted or unsubstituted, derivatives thereof, and combinations thereof. In some instances, Y is the linker substituted with $R^6$, which can be a substituent as described herein. In other instances, Y—$R^6$ defines the linker as described herein for any embodiment. In an example, the Y—$R^6$ is a $[CH_2]n$ or $[CR^6{}_2]_n$ wherein n is an integer. In another example, Y is N, where Y—$R^6$ is NH or $NR^6$.

In Formula A, the R substituent groups, such as $R^1$, $R^2$, $R^3$, $R^5$, and $R^6$ can be any possible substituent or one substituent or a combination of the substituents recited herein. Each ring atom may have the corresponding R substituent, or only 1, 2, 3, 4, or 5 ring atoms may have the R substituent, which may be adjacent or separate from each other. Depending on the ring atom, there may or may not be an R substituent group. These R substituent groups can be on one or more ring atoms or linker atom (e.g., Y). As such, each atom of a ring or linker atom may include a substituent as shown in Formula A. Each R substituent for a specific atom can be any possible substituent or one substituent or a combination of substituents. As such, the $R^1$ ring may include 1, 2, or 3 substituents that are the same or different from each other; and the $R^5$ ring may include 1 or 2 substituents that are the same or different from each other. When on a hetero atom, the $R^1$, $R^2$, $R^3$, $R^5$ may be devoid of a substituent, and thereby nothing but electrons, such as electron pairs etc.

In some embodiments of Formula A, each $R^1$, $R^2$, $R^3$, $R^5$, and $R^6$ are independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, any substituted or unsubstituted, or combinations thereof as well as other well-known chemical substituents. When on a hetero atom, the $R^1$, $R^2$, $R^3$, or $R^5$ may be devoid of a substituent, and thereby nothing but electrons, such as electron pairs etc. When on a hetero atom, $R^6$ can be as defined herein. When on a carbon atom, $R^6$ can be two or more substituents as defined herein.

In some embodiments of Formula A, each $R^1$, $R^2$, $R^3$, $R^5$, and $R^6$ are independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkyl sulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any including straight chains, any including branches, and any including rings, derivatives thereof, any substituted or unsubstituted, and combinations thereof. When on a hetero atom, $R^6$ can be as defined herein. When on a carbon atom, $R^6$ can be two or more substituents as defined herein.

In some embodiments of Formula 1, each $R^1$, $R^2$, $R^3$, $R^5$, and $R^6$ are independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—$NH_2$),), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—$N^+$≡$C^-$), cyanato (—O—C≡N), isocyanato (—O—$N^+$≡$C^-$), thiocyanato (—S—C≡N), isothiocyanato (—S—$N^+$≡$C^-$), azido (—N═$N^+$═$N^-$), formyl (—(CO)—H), thioformyl (—(CS)—H), amino (—$NH_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, $C_1$-$C_{24}$ alkyl, aryl, alkaryl, aralkyl, etc.), arylimino (CR═N(aryl), where R=hydrogen, alkyl, aryl, alkaryl, etc.), nitro (—$NO_2$), nitroso (—NO), sulfonic acid (—$SO_2$—OH), sulfonato (—$SO_2$—$O^-$), $C_1$-$C_{24}$ alkylsulfanyl (—S-alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)(O—)), phospho (—$PO_2$), phosphino (—$PH_2$), any with or without hetero atoms (e.g., N, O, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any inducing rings, any being substituted or unsubstituted, derivatives thereof, and combinations thereof. When on a hetero atom, $R^6$ can be as defined herein. When on a carbon atom, $R^6$ can be two or more substituents as defined herein.

In some embodiments, ring A represents a 5- or 6-membered aryl or heteroaryl ring and is optionally substituted with 1-4 $R^2$ groups; ring B represents one or more (e.g., fused rings) 5- or 6-membered aryl or heteroaryl ring and is optionally substituted with 1-5 $R^3$ groups for each ring; Y is selected from $NR^6C(O)$, $C(O)NR^6$, $NR^6C(O)O$, $NR^6C(O)NR^6$, and $OC(O)NR^6$; each occurrence of $R^1$, $R^2$, $R^3$, and $R^5$ is independently selected from the group consisting of H, halo, —CN, —$NO_2$, —R, —OR, —NRR, —C(O)WR, —OC(O)WR, —NRC(O)WR, —SC(O)WR, NRC(═S)WR, —OC(═S)WR, —C(═S)WR, —WC(═NR)WR, —WP(═O)(WR)(WR), —Si(R)$_3$, —$NR_2$C(═S)WR, —OC(═S)WR, —C(═S)WR, —WC(═NR)WR, —WP(═O)(WR)(WR), —Si(R)$_3$, $NRSO_2R$, —S(O)$_r$R, —$SO_2$NRR and —$NRSO_2$NRR, wherein each W is independently a bond, —O—, —S— or —NR—, and each R s a substituent as defined herein; each R is independently selected from H, alkyl, alkenyl, alkynyl, cycloalkyl, cycloalkenyl, cycloalkynyl, aryl, heterocyclic and heteroaryl; alternatively, adjacent R groups, taken together with the atom to which they are attached, form a 5- or 6-membered saturated, partially saturated or unsaturated ring, which can be optionally substituted and which contains 0-2 heteroatoms selected from N, O and S(O)$_r$; and r is 0, 1, or 2.

Formula B

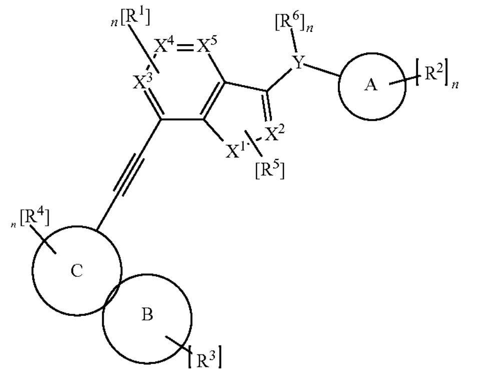

In Formula B, rings A and B and C can be any ring structure with a single ring or two or more fused rings, which can be cycloaliphatic, hetero cycloaliphatic, aryl, hetero aryl, polyaryl, poly hetero aryl, or combinations thereof with 4, 5, 6, 7, 8, 9, 10, 11, or 12 atoms or more for each ring, where fused rings can include more atoms. In some embodiments, rings B and C are single rings that are fused together to form a polycyclic, such as a poly cyclo alkyl or polyaryl. When including hetero atoms, they can be C, O, N, or S, and depend on the number of bonds therewith, and any ring A or B or C can include 1, 2, 3, 4, 5, 6 or more hetero atoms. Rings A and B and C can be substituted with one or more R groups, shown as $R^2$ and $R^3$ and $R^4$. The n is an integer that defines the number of R group substituents for each shown R group in the formula. The number of R group substituents for rings A and B and C are determined by the number of atoms in the ring when single rings (not fused rings B and C) as shown for Ring A being n−1 where n is the number of ring atoms. Each R group substituent on a ring can be different from the others.

In Formula B, the X ring atoms can be the same as defined for Formula A, which can include $X^1$, $X^2$, $X^3$, $X^4$, and $X^5$. The Y may be the same as defined for Formula A. For example, when Y is an O or S, $R^6$ is nothing. When one or more of $X^3$, $X^4$, and $X^5$ is carbon, $R^1$ is a substituent as defied herein on each carbon. When all $X^3$, $X^4$, and $X^5$ are nitrogen, $R^1$ is a nothing or electrons as described herein.

In Formula B, each $R^1$, $R^2$, $R^3$, $R^5$, and $R^6$ are independently as defined for Formula A. Additionally, $R^4$ can be the same as defined for any of $R^1$, $R^2$, $R^3$, $R^5$, and $R^6$ herein, such as for Formula A.

Formula C

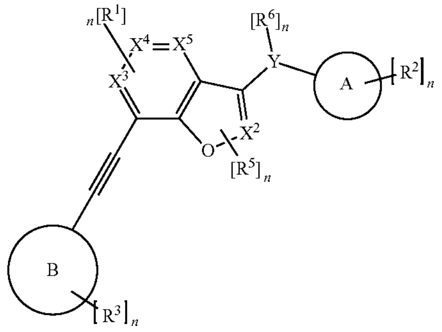

In Formula C, rings A and B can be as defined for Formula A. Rings A and B can be substituted with one or more R groups, shown as $R^2$ and $R^3$. The n is an integer that defines the number of R groups for each shown R group. The number of R group substituents for rings A and B are determined by the number of atoms in the ring as defined for Formula A. The n can range from 0 to the maximum allowed R groups for the structure to which the substituent is attached.

In Formula C, the X ring atoms can be the same as defined for Formula A, which can include $X^2$, $X^3$, $X^4$, and $X^5$. The Y may be the same as defined for Formula A. When one or more of $X^3$, $X^4$, and $X^5$ is carbon, $R^1$ is a substituent as defied herein on each carbon. When all $X^3$, $X^4$, and $X^5$ are nitrogen, $R^1$ is a nothing or electrons as described herein.

In Formula C, each $R^1$, $R^2$, $R^3$, $R^5$, and $R^6$ are independently as defined for Formula A.

Formula D

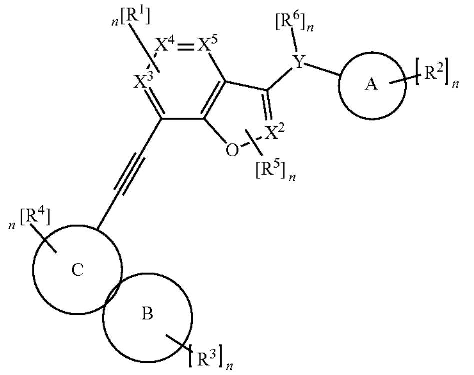

In Formula D, rings A and B and C can be as defined for Formula B. Rings A and B and C can be substituted with one or more R groups, shown as $R^2$ and $R^3$ and $R^4$. The number of R group substituents for rings A and B and C are determined by the number of atoms in the ring when single rings (not fused rings B and C) as shown for Ring A being n−1 where n is the number of ring atoms. Each R group substituent on a ring can be different from the others. The n can range from 0 to the maximum allowed R groups for the structure to which the substituent is attached.

In Formula D, the X ring atoms can be the same as defined for Formula B, which can include $X^2$, $X^3$, $X^4$, and $X^5$. The Y may be the same as defined for Formula B. When one or more of $X^3$, $X^4$, and $X^5$ is carbon, $R^1$ is a substituent as defied herein on each carbon. When all $X^3$, $X^4$, and $X^5$ are nitrogen, $R^1$ is a nothing or electrons as described herein.

In Formula D, each $R^1$, $R^2$, $R^3$, $R^4$, $R^5$, and $R^6$ are independently as defined for Formula B.

Formula E

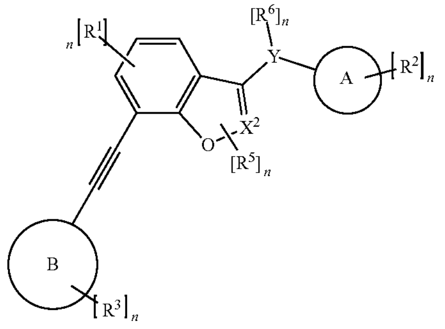

In Formula E, rings A and B can be as defined for Formula A. Rings A and B can be substituted with one or more R groups, shown as $R^2$ and $R^3$. The number of R group substituents for rings A and B are determined by the number of atoms in the ring as defined for Formula A. Each n can independently range from 0 to the maximum allowed R groups for the structure to which the substituent is attached.

In Formula E, the X ring atoms can be the same as defined for Formula A, which can include $X^2$. The Y may be the same as defined for Formula A.

In Formula E, each $R^1$, $R^2$, $R^3$, $R^5$, and $R^6$ are independently as defined for Formula A.

Formula F

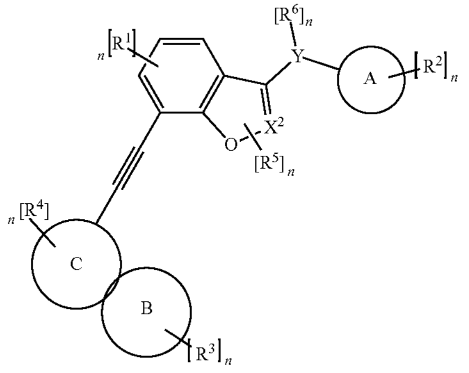

In Formula F, rings A and B and C can be as defined for Formula B. Rings A and B and C can be substituted with one or more R groups, shown as $R^2$ and $R^3$ and $R^4$. The number of R group substituents for rings A and B and C are determined by the number of atoms in the ring when single rings (not fused rings B and C) as shown for Ring A being n−1 where n is the number of ring atoms. Each R group substituent on a ring can be different from the others. Each n can independently range from 0 to the maximum allowed R groups for the structure to which the substituent is attached.

In Formula F, the X ring atoms can be the same as defined for Formula B, which can include $X^2$. The Y may be the same as defined for Formula B.

In Formula F, each $R^1$, $R^2$, $R^3$, $R^4$, $R^5$, and $R^6$ are independently as defined for Formula B.

Formula G

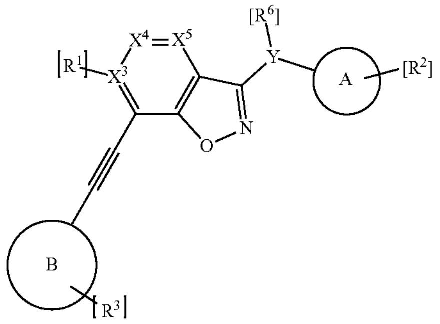

In Formula G, rings A and B can be as defined for Formula A. Rings A and B can be substituted with one or more R groups, shown as $R^2$ and $R^3$. The number of R group substituents for rings A and B are determined by the number of atoms in the ring as defined for Formula A. Each n can independently range from 0 to the maximum allowed R groups for the structure to which the substituent is attached.

In Formula G, the X ring atoms can be the same as defined for Formula A, which can include $X^3$, $X^4$, and $X^5$. The Y may be the same as defined for Formula A.

In Formula G, each $R^1$, $R^2$, $R^3$, $R^5$, and $R^6$ are independently as defined for Formula A.

Formula H

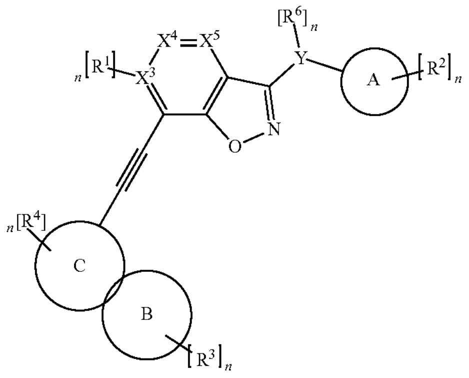

In Formula H, rings A and B and C can be as defined for Formula B. Rings A and B and C can be substituted with one or more R groups, shown as $R^2$ and $R^3$ and $R^4$. The number of R group substituents for rings A and B and C are determined by the number of atoms in the ring when single rings (not fused rings B and C) as shown for Ring A being n−1 where n is the number of ring atoms. Each R group substituent on a ring can be different from the others. Each n can independently range from 0 to the maximum allowed R groups for the structure to which the substituent is attached.

In Formula H, the X ring atoms can be the same as defined for Formula B, which can include $X^3$, $X^4$, and $X^5$. The Y may be the same as defined for Formula B.

In Formula H, each $R^1$, $R^2$, $R^3$, $R^4$, $R^5$, and $R^6$ are independently as defined for Formula B.

In some embodiments, the Formula A-H can include $X^1$ is O. In some embodiments, $X^2$ is N. In some embodiments, $X^1$ is O and $X^2$ is N. These embodiments can be applied to any formula shown herein.

In some embodiments, the Formula A-H can include at least one of $X^1$, $X^2$, or $X^3$ is carbon. In some embodiments, at least two of $X^1$, $X^2$, or $X^3$ is carbon. In some embodiments, all of $X^1$, $X^2$, or $X^3$ is carbon. These embodiments can be applied to any formula shown herein, and may be combined with any other embodiments, such as when $X^1$ is O and/or $X^2$ is N. In some embodiments, the Formula A-H can include one or more of V, $X^2$, or $X^3$ being carbon or nitrogen.

The Formulae A-H show embodiments of the kinase (e.g., DDR1) inhibitor, where the substituents and variables have been defined herein.

In some embodiments, the Formula A-H can include $R^1$ on the $X^1$ atom.

In some embodiments, the Formula A-H can include $R^1$ being H, halogen, $C_1$-$C_5$ alkyl optionally substituted by a substituent that includes halogen, S, O, or N along with appropriate hydrogen atoms or additional substituents. In some embodiments, the Formula A-H can include $R^1$ being $C_3$-$C_6$ cycloalkyl or heterocycloalkyl.

In some embodiments, the Formula A-H can include Y or Y—$R^6$ being $(CH_2)_n$ with n=1-3, N, —NHC(O)—, —C(O)NH—, S, —NHS(O)—, —S(O)NH—S(O), $S(O)_2$, or O.

In some embodiments, the Formula A-H can include one or both of $R^3$ or $R^4$ can be hydrogen or no substituent.

For the Formulae A-H, the Ring A can be a $C_3$-$C_6$ cycloalkyl or heterocycloalkyl that is substituted or unsubstituted; or $C_1$-$C_5$ alkyl containing 1-3 halogens; aromatic ring with or without hetro atoms that is substituted or unsubstituted; or heterocycle ring (e.g., aliphatic or aromatic) containing 5-9 ring atoms including C, N, S, or O with or without fused or annelated cycles, or combinations thereof.

For the Formulae A-H, the Ring A can be substituted with one or more substituents (e.g., 2 substituents), and thereby have two different $R^2$ groups. The $R^2$ groups can be $C_1$-$C_5$ alkyl or $C_1$-$C_5$ hetero alkyl (e.g., with N, S, or O) that is substituted or unsubstituted; $C_3$-$C_6$ cycloalkyl (including N, S, O substituted) or heterocycloalkyl that is substituted or unsubstituted; or $C_1$-$C_5$ alkyl substituted or unsubstituted; or $C_1$-$C_5$ alkyl substituted with halo atoms at one or more locations.

For the Formulae A-H, the Ring A can be Formula Ring A, where each ring X ring atom can be as defined herein in any of the formulae, with the dashed lines showing optional bonds so as to form optional double bonds, and thereby may aliphatic or aromatic. In Formula Ring A, m may be an integer, or 1, 2, 3, 4, 5, or 6, and the n can be from 0 to the maximum allowed number of substituents, which can be applied to any of the formulae herein.

Formula Ring A

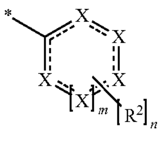

In some embodiments, Formula Ring A can be any of the following:

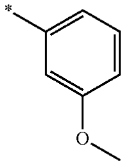
;
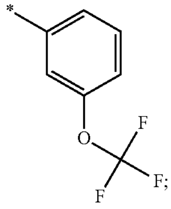
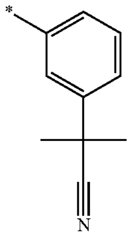
;

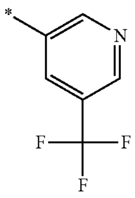
;
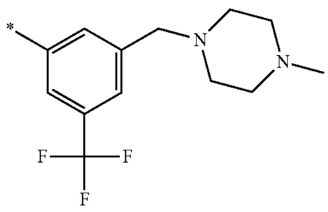
;

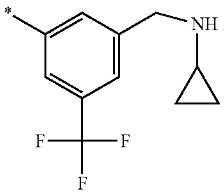
;
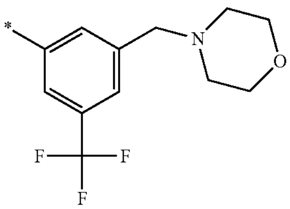
;

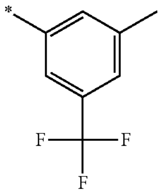
;
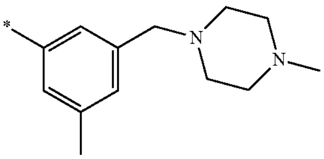
;

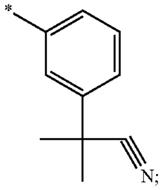
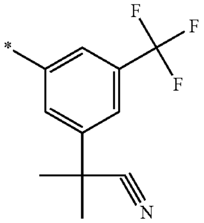
;

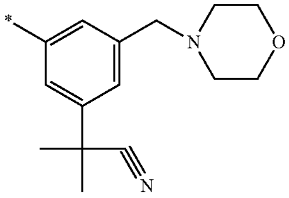

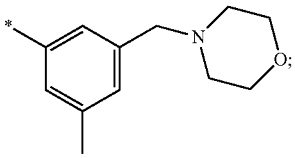

-continued

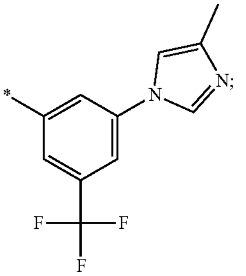

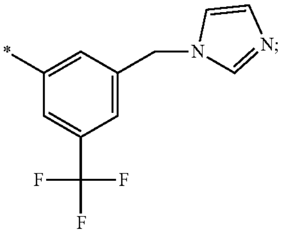

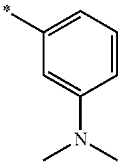
;
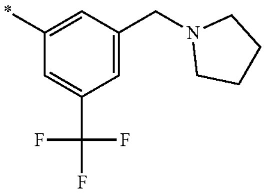
;

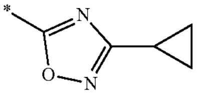
;
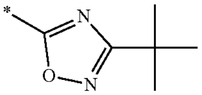
;

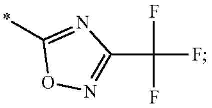

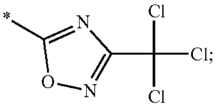

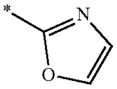
; or
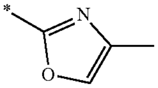
.

In some embodiments, Formula Ring A can be any of the following:

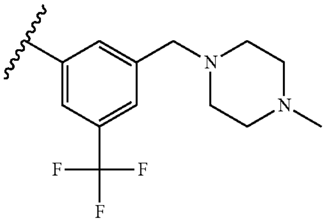
,

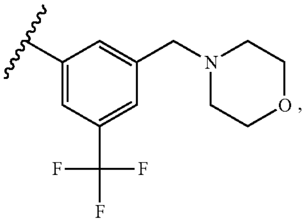

-continued

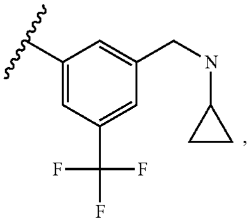
,
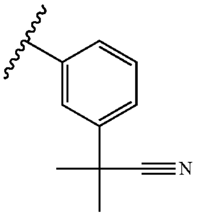
,

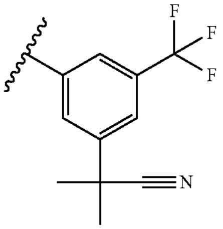
,
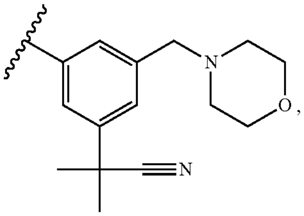

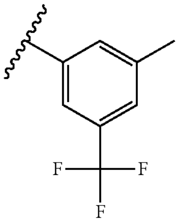
,
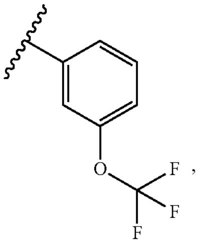

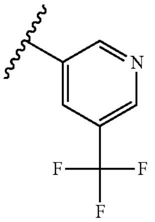
,
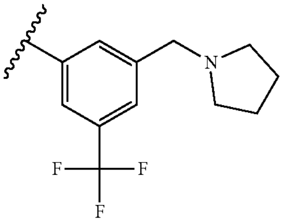
,

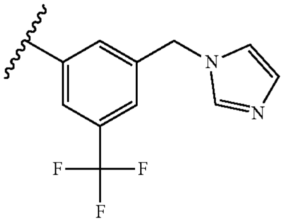
,

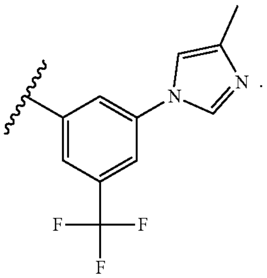
.

For the Formulae A-H, the Ring B or combination of Ring B fused with Ring C can be Formula Fused Ring B1, where each ring X ring atom can be as defined herein in any of the formulae. The dashed lines represent optional bonds that may be present depending on the atoms, which can be part of single or double bonds, so as to be aliphatic or aromatic. Any of the carbon atoms in the Formula Fused Ring B1 can be substituted with a R group in accordance with the formulae and structures recited herein.

Formula Fused Ring B1

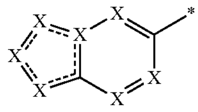

In some embodiments, Formula Fused Ring B1 can be any of the following:

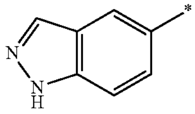 ; 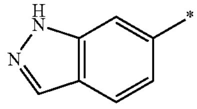 ;

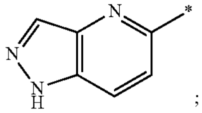 ; 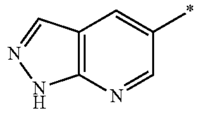 ;

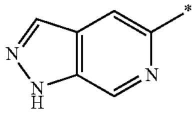 ; 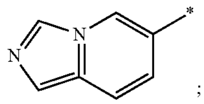 ;

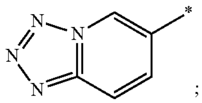 ; or 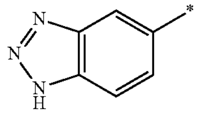 .

For the Formulae A-H, the Ring B or combination of Ring B fused with Ring C can be Formula Fused Ring B2, where each ring X ring atom can be as defined herein in any of the formulae. The dashed lines represent optional bonds that may be present depending on the atoms, which can be in single or double bonds. Any of the carbon atoms in the Formula Fused Ring B2 can be substituted with a R group in accordance with the formulae and structures recited herein.

Formula Fused Ring B2

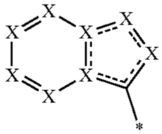

In some embodiments, Formula Fused Ring B2 can be any of the following:

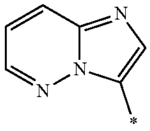 ; 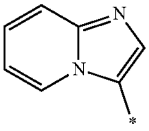 ;

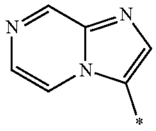 ; 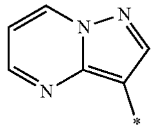 ;

-continued

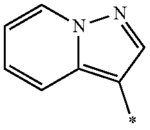 ; 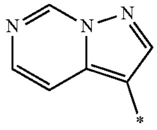 ;

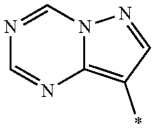 ; or 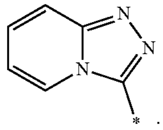 .

For the Formulae A-H, the Ring B can be Formula Ring B3, where each ring X ring atom can be as defined herein in any of the formulae. Any of the carbon atoms in the Formula Ring B3 can be substituted with a R group in accordance with the formulae and structures recited herein.

Formula Ring B3

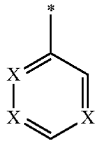

In some embodiments, Formula Ring B3 can be any of the following:

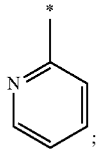 ; 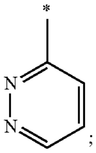 ; 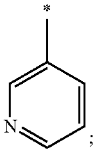 ; or 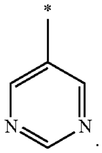 .

Ring B or combination of Ring B fused with Ring C can be Formula Fused Ring B4, where each ring X ring atom can be as defined herein in any of the formulae. Any of the carbon atoms in the Formula Fused Ring B4 can be substituted with a R group in accordance with the formulae and structures recited herein.

Formula Fused Ring B4

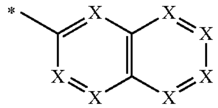

For the Formulae A-H, the Ring B or combination of Ring B fused with Ring C can be Formula Fused Ring B4 can be as shown below, wherein any of the carbon atoms can be substituted with a R group in accordance with the formulae and structures recited herein.

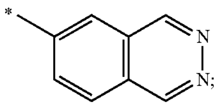 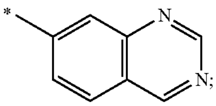

-continued

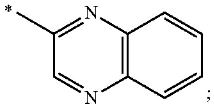;
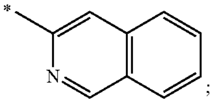;
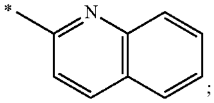; or
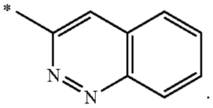.

For the Formulae A-H, the ring atoms of Ring B or combination of Ring B fused with Ring C may be devoid of a substituent, and only include appropriate hydrogens and electrons.

In some embodiments, ring B can be as follows:

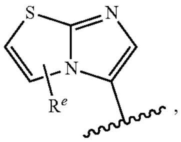,
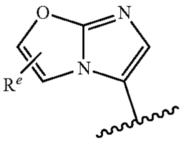,
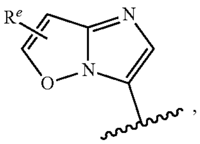,
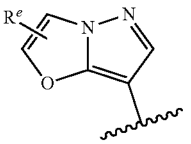, wherein each $R^e$ is independently selected from H, alkyl, alkenyl, alkynyl, cycloalkyl, cycloalkenyl, cycloalkynyl, aryl, heterocyclic and heteroaryl.

In some embodiments, ring B can be as follows:

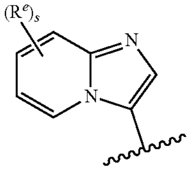,
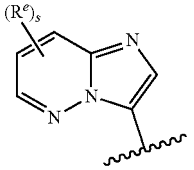,
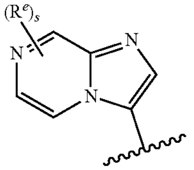,
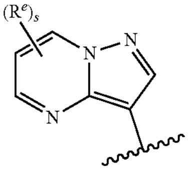,
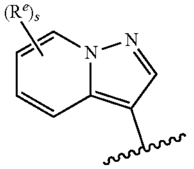,
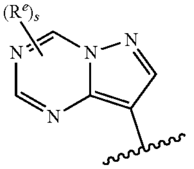,
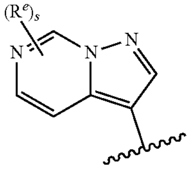, wherein each W is independently selected from H, alkyl, alkenyl, alkynyl, cycloalkyl, cycloalkenyl, cycloalkynyl, aryl, heterocyclic and heteroaryl, and s is an integer, such as 0, 1, 2, 3, 4, 5, or 6.

In some embodiments, ring A can be as follows:

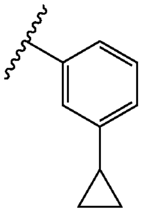,
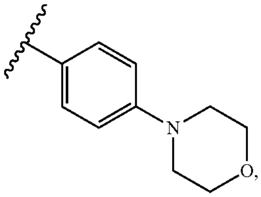
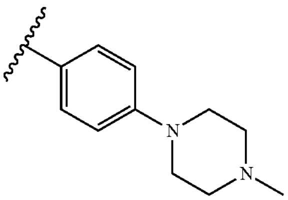,
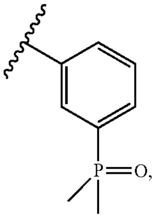
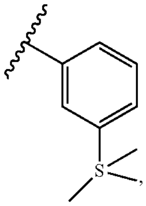
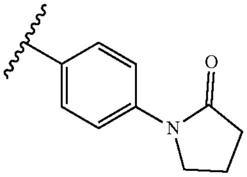,
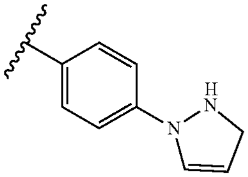,
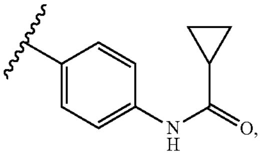
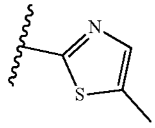,
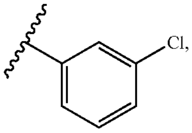
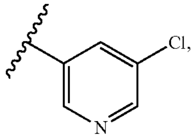
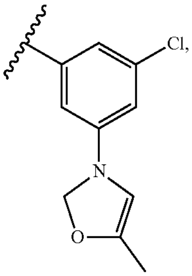
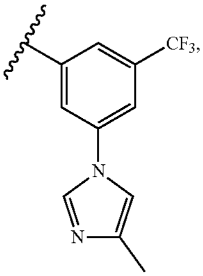
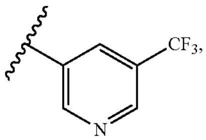
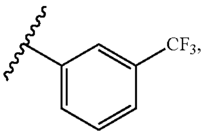

-continued
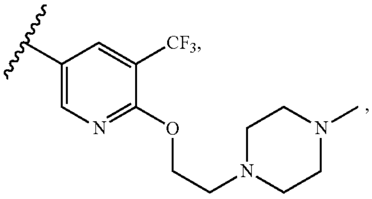
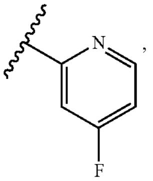
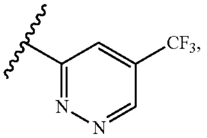
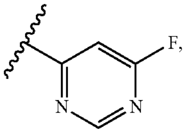
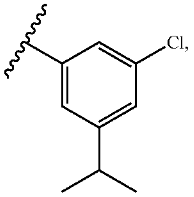
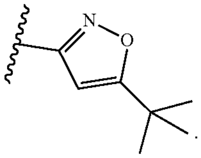
In some embodiments, $R^2$ can be as follows:
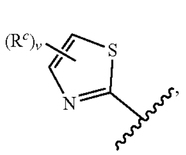
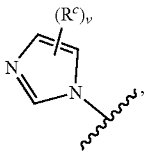
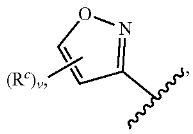
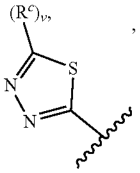
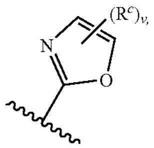
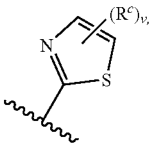
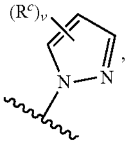
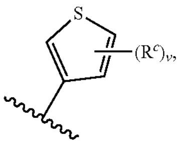
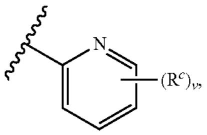
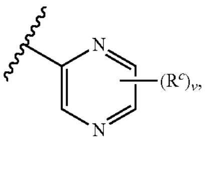
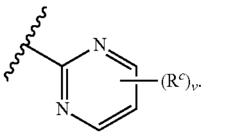
wherein RC is as defined for $R^2$ and v is an integer, such as 0, 1, 2, 3, 4, or 5.
Some additional examples of ring A can also include:
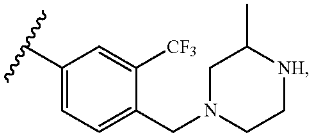
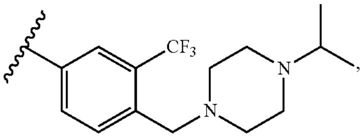
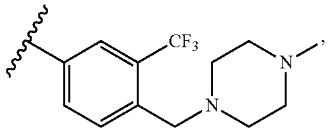
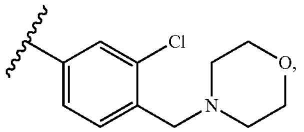
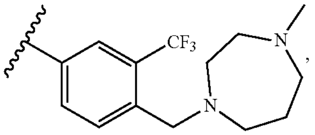
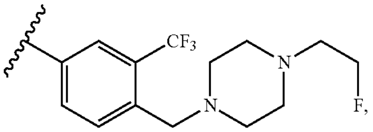
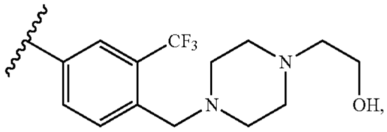
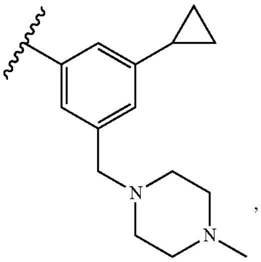
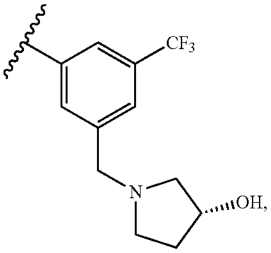
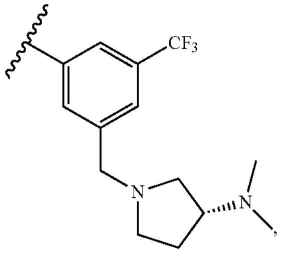
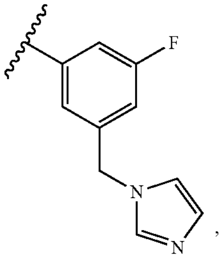

Some additional examples of ring B can include:

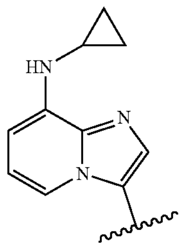 ,

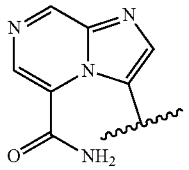 ,

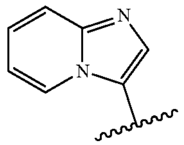 ,

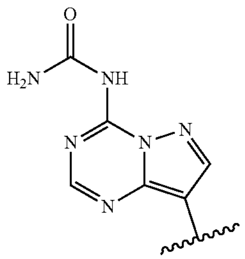 ,

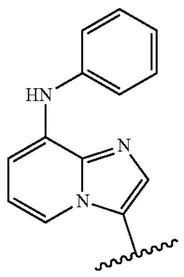 ,

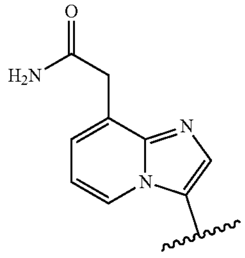 ,

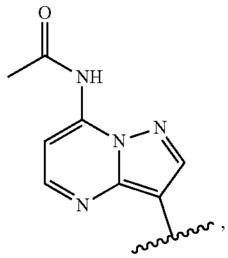 ,

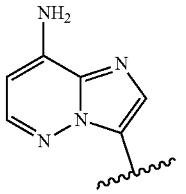 ,

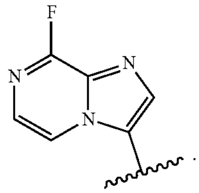 .

In some embodiments, the kinase (e.g., DDR1) inhibitor has a structure of Formula 1 through Formula 28, derivative thereof, prodrug thereof, salt thereof, or stereoisomer thereof, or having any chirality at any chiral center, or tautomer, polymorph, solvate, or combination thereof, as presented herein. In some instances, the compounds can be pharmaceutically acceptable salts. As in these formulae, the R substituent groups can be any substituents. For example, the R substituent groups can be one or more of the substituents recited herein or combinations thereof.

Formula 1

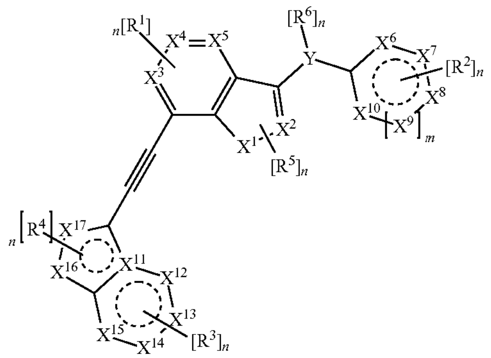

In Formula 1, the X ring atoms can be carbon (C) or a hetero atom, such as O, N, S, or other. As noted, when carbon, each X ring atom may or may not have a substituent, such as shown by as $R^1$, $R^2$, $R^3$, $R^4$, and $R^5$, which can be on any of the one or more atoms of the respective ring, such as on the X ring atom, if present, such as in $X^1$, $X^2$, $X^3$, $X^4X^5$, $X^6$, $X^7$, $X^8$, $X^9$, $X^{10}$, $X^{11}$, $X^{12}$, $X^{13}$, $X^{14}$, $X^{15}$, $X^{16}$, and $X^{17}$. As such, $X^1$ can be a C (e.g., $CH_2$) or O or N (e.g., NH) or S, with the appropriate hydrogen atoms. The $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, and $X^{17}$ can be a C (e.g., CH or CR) or N, with the appropriate hydrogen atoms. When the X ring atom has two bonds it can be C, O, N, or S, when 3 bonds it can be as C, or N. The m for the number of ring atoms can be an integer, such as 0, 1, 2, 3, 4, 5, 6, etc. Each n can independently range from 0 to the maximum allowed R groups for the structure to which the substituent is attached, which can be applied to any formula herein.

In Formula 1, the Y can be any linker, such as defined herein. When Y is one chain atom or more than one chain atom, there may be a $R^6$ on one or more of the chain atoms. In an example, when Y is an O or S, $R^6$ is nothing. Otherwise, $R^6$ can be as defined herein. The dashed circles show the ring can optionally be aliphatic or aromatic, which is for any embodiment.

In Formula 1, the R substituent groups, such as $R^1$, $R^2$, $R^3$, $R^4$, $R^5$ and $R^6$ can be as defined herein, such as for Formulae A-H or others. When $X^1$ is O and $X^2$ is N, then $R^5$ is nothing (e.g., no substituent), which can be only electrons.

Formula 2

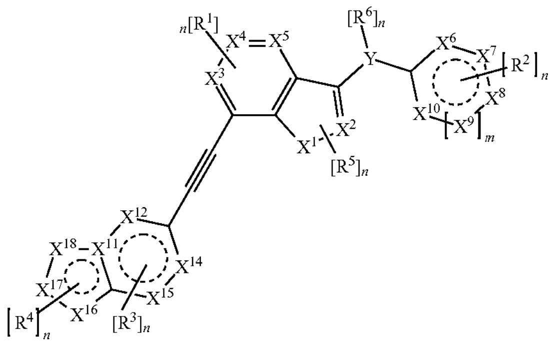

In Formula 2, the X ring atoms (e.g., $X^1$, $X^2$, $X^3$, $X^4$, $X^5$, $X^6$, $X^7$, $X^8$, $X^9$, $X^{10}$, $X^{11}$, $X^{12}$, $X^{14}$, $X^{15}$, $X^{16}$, $X^{17}$, and $X^{18}$), linker Y, and R groups $R^1$, $R^2$, $R^3$, $R^4$, $R^5$, and $R^6$ can be as defined for Formula 1. $X^{18}$ can be the same as for $X^{17}$ as defined herein.

Formula 3

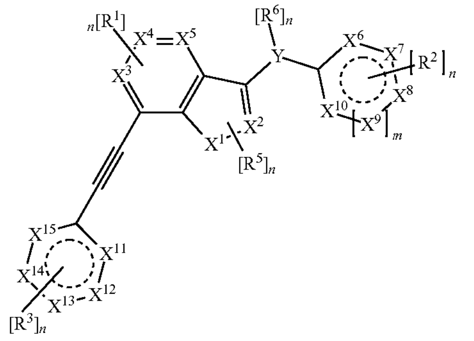

In Formula 3, the X ring atoms (e.g., $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$), linker Y, and R groups $R^1$, $R^2$, $R^3$, $R^4$, $R^5$, and $R^6$ can be as defined for Formula 1.

Formula 4

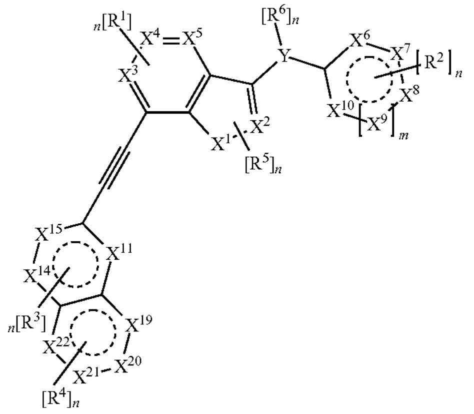

In Formula 4, the X ring atoms (e.g., $X^1$, $X^2$, $X^3$, $X^4$, $X^5$, $X^6$, $X^7$, $X^8$, $X^9$, $X^{10}$, $X^{11}$, $X^{14}$, $X^{15}$, $X^{19}$, $X^{20}$, $X^{21}$, and $X^{22}$), linker Y, and R groups $R^1$, $R^2$, $R^3$, $R^4$, $R^5$, and $R^6$ can be as defined for Formula 1. $X^{19}$, $X^{20}$, $X^{21}$, and $X^{22}$ can be the same as for $X^{17}$ as defined herein.

Formula 5

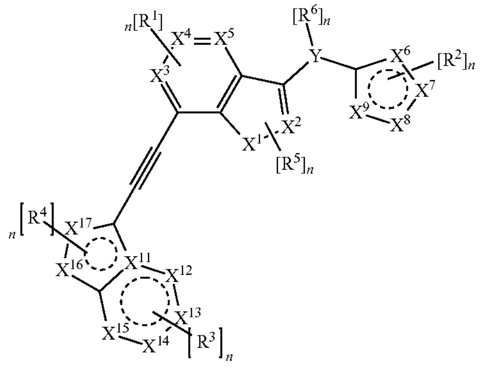

In Formula 5, the X ring atoms (e.g., $X^1$, $X^2$, $X^3$, $X^4$, $X^5$, $X^6$, $X^7$, $X^8$, $X^9$, $X^{11}$, $X^{12}$, $X^{13}$, $X^{14}$, $X^{15}$, $X^{16}$, and $X^{17}$), linker Y, and R groups $R^1$, $R^2$, $R^3$, $R^4$, $R^5$, and $R^6$ can be as defined for Formula 1.

Formula 6

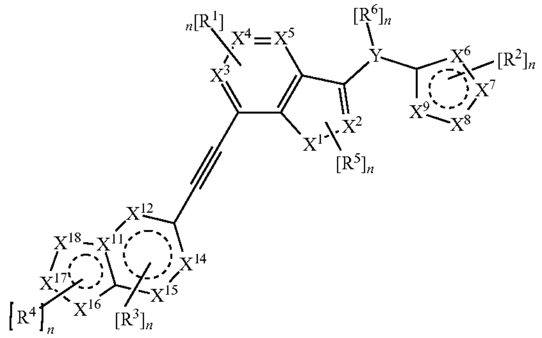

In Formula 6, the X ring atoms (e.g., $X^1$, $X^2$, $X^3$, $X^4$, $X^5$, $X^6$, $X^7$, $X^8$, $X^9$, $X^{11}$, $X^{12}$, $X^{14}$, $X^{15}$, $X^{16}$, $X^{17}$, and $X^{18}$), linker Y, and R groups $R^1$, $R^2$, $R^3$, $R^4$, $R^5$, and $R^6$ can be as defined for Formulae 1-5.

Formula 7

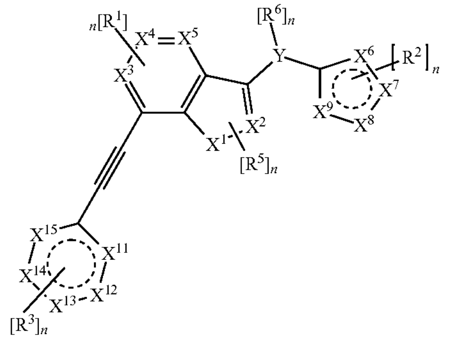

In Formula 7, the X ring atoms (e.g., $X^1$, $X^2$, $X^3$, $X^4$, $X^5$, $X^6$, $X^7$, $X^8$, $X^9$, $X^{11}$, $X^{12}$, $X^{13}$, $X^{14}$, and $X^{15}$), linker Y, and R groups $R^1$, $R^2$, $R^3$, $R^4$, $R^5$, and $R^6$ can be as defined for Formulae 1-5.

Formula 8

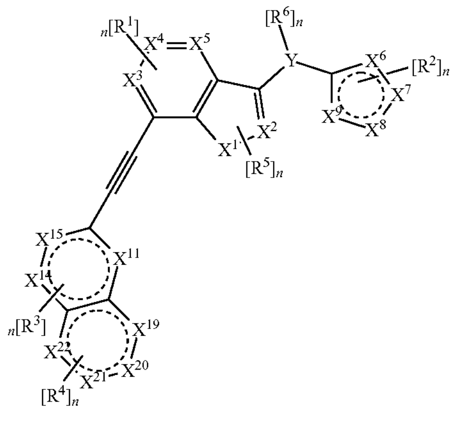

In Formula 8, the X ring atoms (e.g., $X^1$, $X^2$, $X^3$, $X^4$, $X^5$, $X^6$, $X^7$, $X^8$, $X^9$, $X^{11}$, $X^{14}$, $X^{15}$, $X^{19}$, $X^{20}$, $X^{21}$, and $X^{22}$), linker Y, and R groups $R^1$, $R^2$, $R^3$, $R^4$, $R^5$, and $R^6$ can be as defined for Formula 1-5.

Formula 9

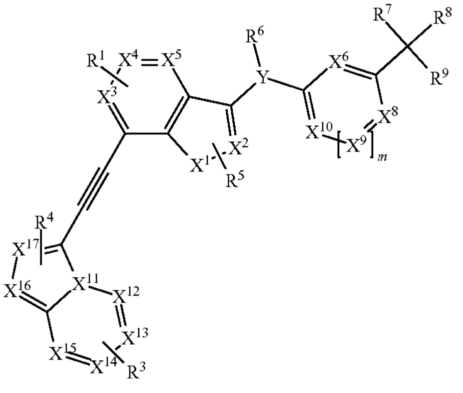

In Formula 9, the X ring atoms (e.g., $X^1$, $X^2$, $X^3$, $X^4$, $X^5$, $X^6$, $X^8$, $X^9$, $X^{10}$, $X^{11}$, $X^{12}$, $X^{13}$, $X^{14}$, $X^{15}$, $X^{16}$, and $X^{14}$), linker Y, and R groups $R^1$, $R^2$, $R^3$, $R^4$, $R^5$, and $R^6$ can be as defined for Formula 1-5.

Formula 10

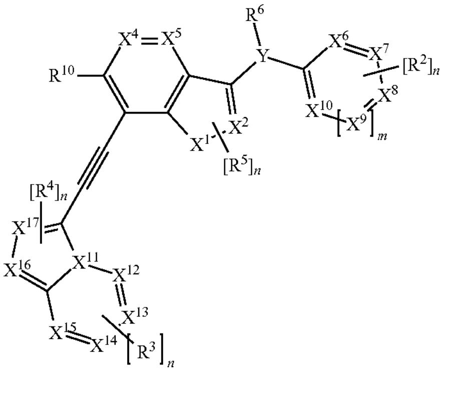

In Formula 10, the X ring atoms (e.g., $X^1$, $X^2$, $X^4$, $X^5$, $X^6$, $X^8$, $X^9$, $X^{10}$, $X^{11}$, $X^{12}$, $X^{13}$, $X^{14}$, $X^{15}$, $X^{16}$, and $X^{17}$), linker Y, and R groups $R^1$, $R^2$, $R^3$, $R^4$, $R^5$, and $R^6$ can be as defined for Formula 1-5.

Formula 11

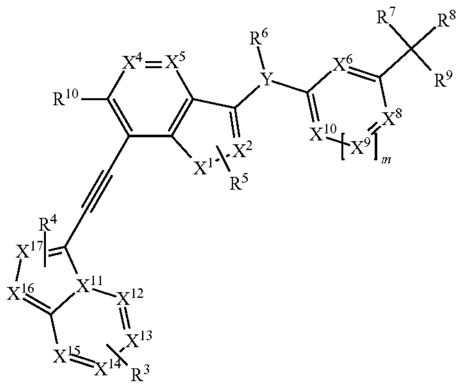

In Formula 11, the X ring atoms (e.g., $X^1$, $X^2$, $X^4$, $X^5$, $X^6$, $X^8$, $X^9$, $X^{10}$, $X^{11}$, $X^{12}$, $X^{13}$, $X^{14}$, $X^{15}$, $X^{16}$ and $X^{17}$), linker Y, and R groups $R^1$, $R^2$, $R^3$, $R^4$, $R^5$, and $R^6$ can be as defined for Formula 1-5.

Formula 12

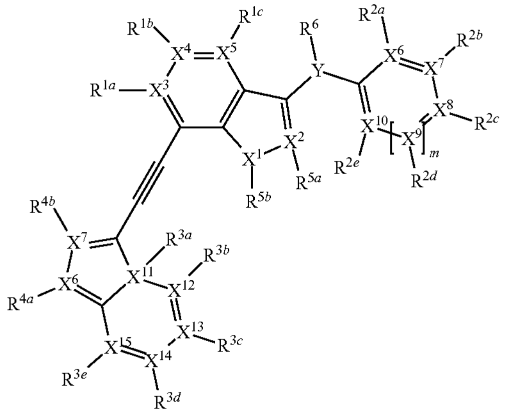

In Formula 12, the X ring atoms and Y linker can be as defined for Formulae 1-5.

The $R^{1a}$, $R^{1b}$, and $R^{1c}$ can each independently be the same as $R^1$ is defined herein. The $R^{2a}$, $R^{2b}$, $R^{2c}$, $R^{2d}$, and $R^{2c}$ can each independently be the same as $R^2$ is defined herein. The $R^{3a}$, $R^{3b}$, $R^{3c}$, $R^{3d}$, and $R^{3e}$ can each independently be the same as $R^3$ is defined herein. The $R^{4a}$ and $R^{4b}$ can each independently be the same as $R^4$ is defined herein. The $R^{5a}$ and $R^{5b}$ can each independently be the same as $R^5$ is defined herein. When on a hetero atom (e.g., N), $R^6$ can be as defined herein. When on a carbon atom, $R^6$ can be two or more substituents as defined herein. When Y is an O or S, $R^6$ is nothing.

Formula 13

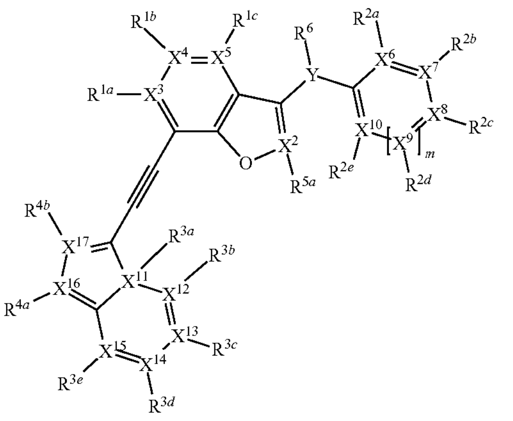

In Formula 13, the X ring atoms, Y linker, and R group substituents can be as defined in Formula 12.

Formula 14

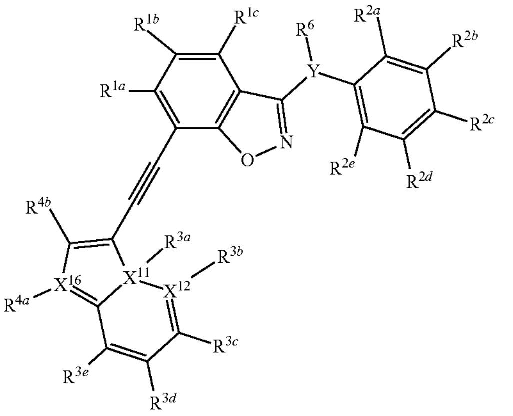

In Formula 14, the X ring atoms, Y linker, and R group substituents can be as defined in Formula 12.

Formula 15

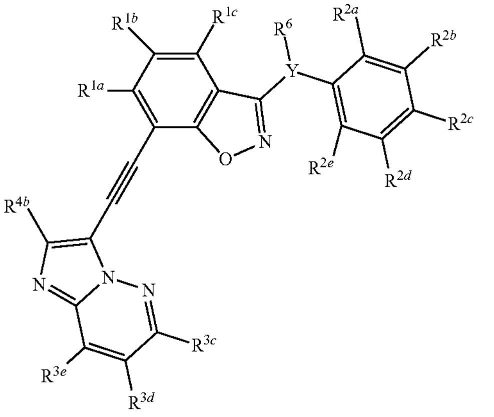

In Formula 15, the Y linker, and R group substituents can be as defined in Formula 12.

Formula 16

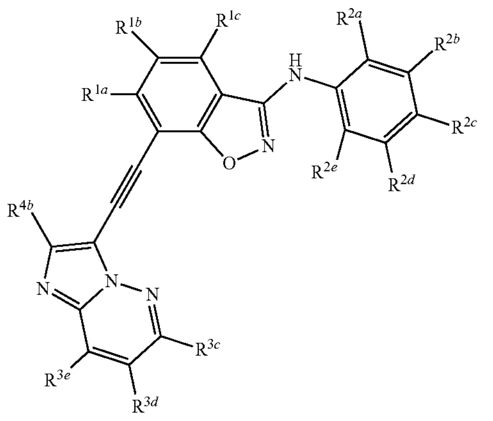

In Formula 16, the R group substituents can be as defined in Formula 12.

Formula 17

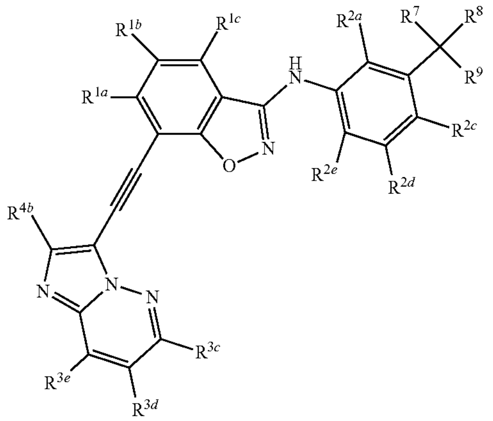

In Formula 17, the R group substituents can be as defined in Formula 12. The $R^7$, $R^8$, and $R^9$ can be as defined herein, such as for $R^2$.

Formula 18

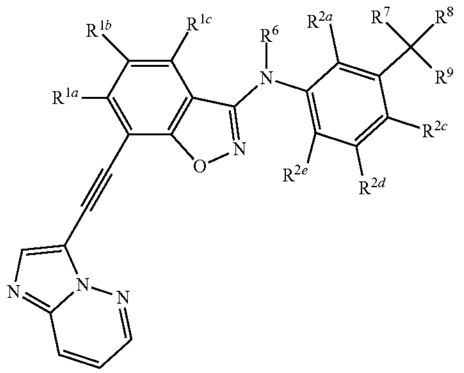

In Formula 18, the R group substituents can be as defined in Formula 17.

Formula 19

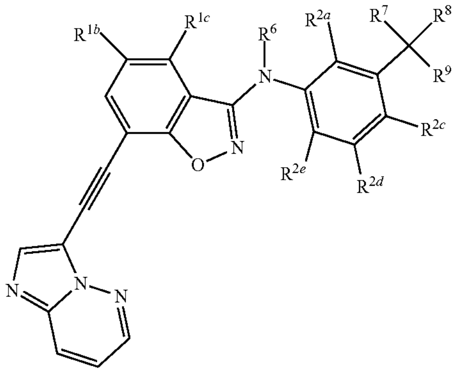

In Formula 19, the R group substituents can be as defined in Formula 17.

Formula 20

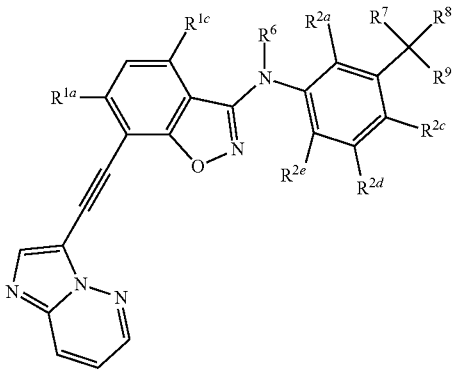

In Formula 20, the R group substituents can be as defined in Formula 17.

Formula 21

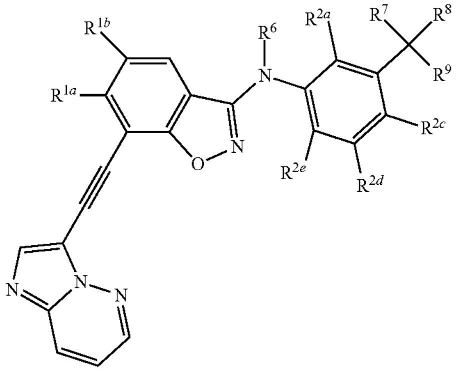

In Formula 21, the R group substituents can be as defined in Formula 17.

Formula 22

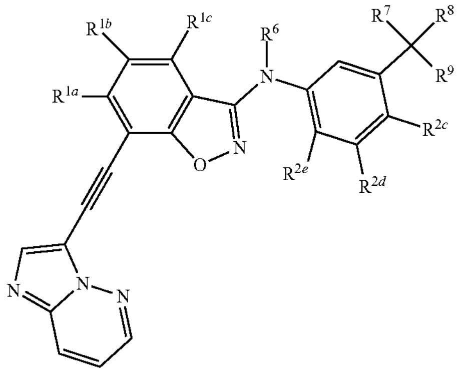

In Formula 22, the R group substituents can be as defined in Formula 17.

Formula 23

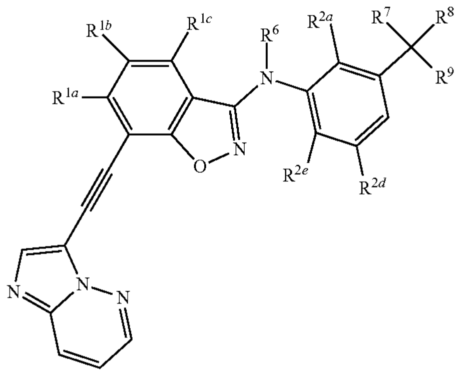

In Formula 23, the R group substituents can be as defined in Formula 17.

Formula 24

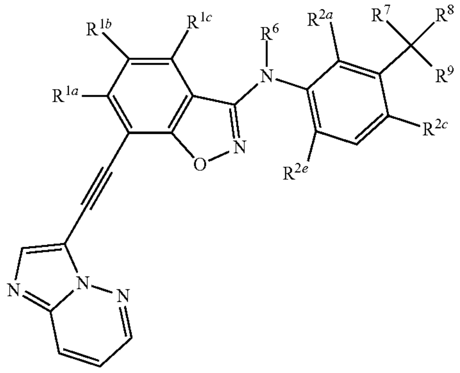

In Formula 24, the R group substituents can be as defined in Formula 17.

Formula 25

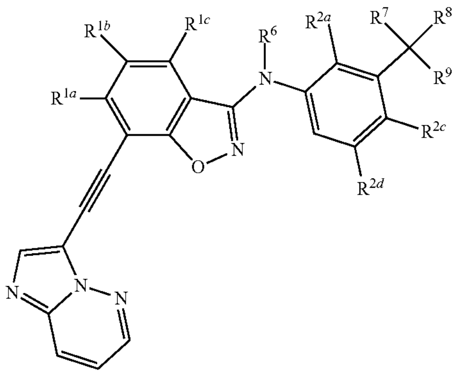

In Formula 25, the R group substituents can be as defined in Formula 17.

Formula 26

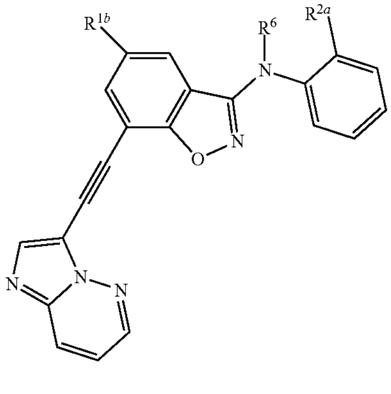

In Formula 26, the R group substituents can be as defined in Formula 12.

Formula 27

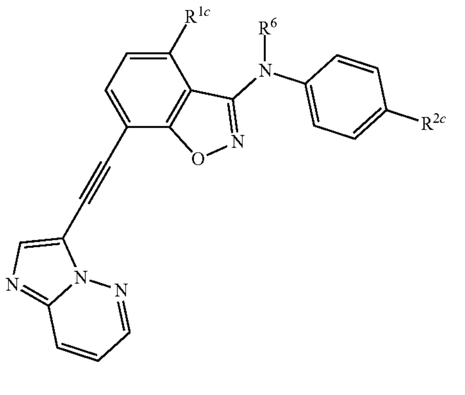

In Formula 27, the R group substituents can be as defined in Formula 12.

Formula 28

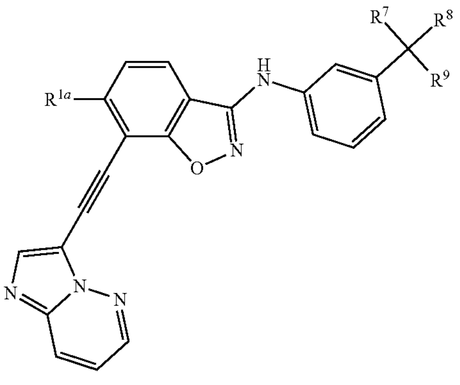

In Formula 28, the R group substituents can be as defined in Formula 17.

Compound 1

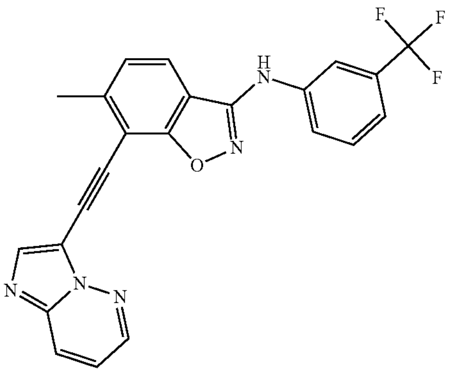

Compound 1, which is 7-(Imidazo[1,2-b]pyridazin-3-ylethynyl)-6-methyl-N-(3-(trifluoromethyl)phenyl)benzo[d]isoxazol-3-amine, is an Example of a DDR1 inhibitor. Compounds 2-121 are also examples of DDR1 inhibitors, shown as follows:

Compound 2

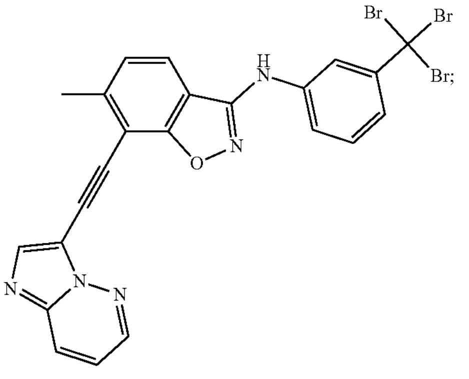

7-(imidazo[1,2-b]pyridazin-3-ylethynyl)-6-methyl-N-(3-(tribromomethyl)phenyl)benzo[d]isoxazol-3-amine -continued Compound 3

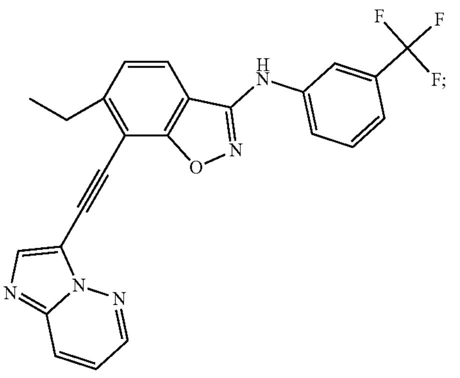

6-ethyl-7-(imidazo[1,2-b]pyridazin-3-ylethynyl)-N-(3-(trifluoromethyl)phenyl)benzo[d]isoxazol-3-amine Compound 4

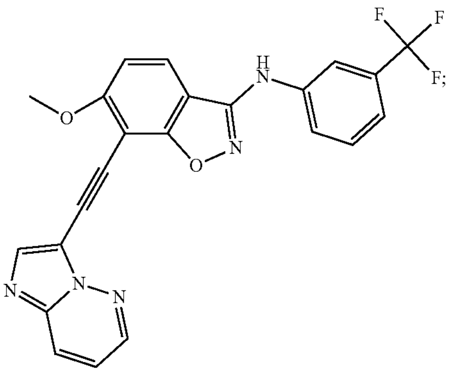

7-(imidazo[1,2-b]pyridazin-3-ylethynyl)-6-methoxy-N-(3-(trifluoromethyl)phenyl)benzo[d]isoxazol-3-amine Compound 5

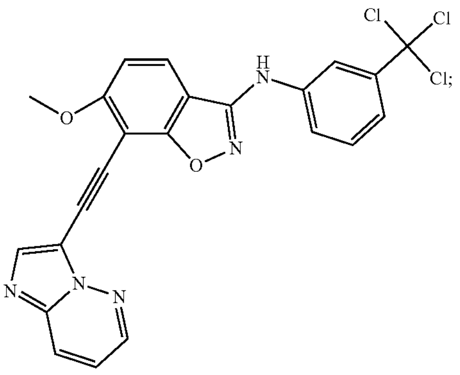

7-(imidazo[1,2-b]pyridazin-3-ylethynyl)-6-methoxy-N-(3-(trichloromethyl)phenyl)benzo[d]isoxazol-3-amine -continued Compound 6

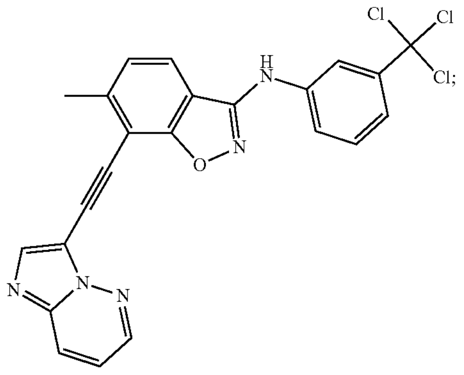

7-(imidazo[1,2-b]pyridazin-3-ylethynyl)-6-methyl-N-(3-(trichloromethyl)phenyl)benzo[d]isoxazol-3-amine Compound 7

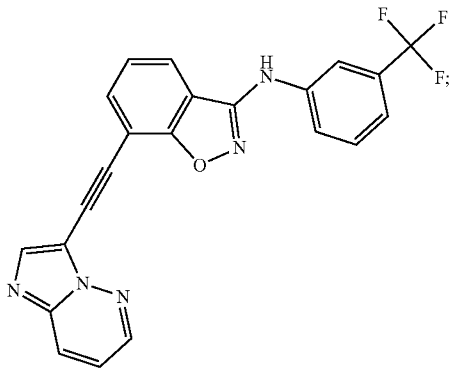

7-(imidazo[1,2-b]pyridazin-3-ylethynyl)-N-(3-(trifluoromethyl)phenyl)benzo[d]isoxazol-3-amine Compound 8

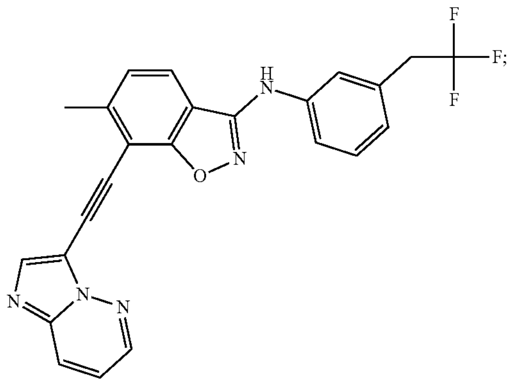

7-(imidazo[1,2-b]pyridazin-3-ylethynyl)-6-methyl-N-(3-(2,2,2-trifluoroethyl)phenyl)benzo[d]isoxazol-3-amine -continued Compound 9

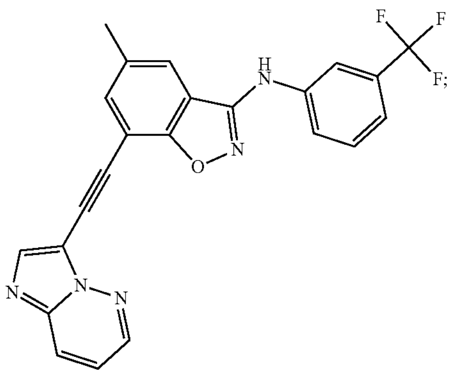

7-(imidazo[1,2-b]pyridazin-3-ylethynyl)-5-methyl-N-(3-(trifluoromethyl)phenyl)benzo[d]isoxazol-3-amine Compound 10

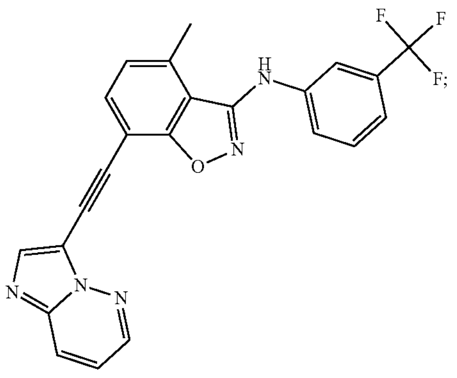

7-(imidazo[1,2-b]pyridazin-3-ylethynyl)-4-methyl-N-(3-(trifluoromethyl)phenyl)benzo[d]isoxazol-3-amine Compound 11

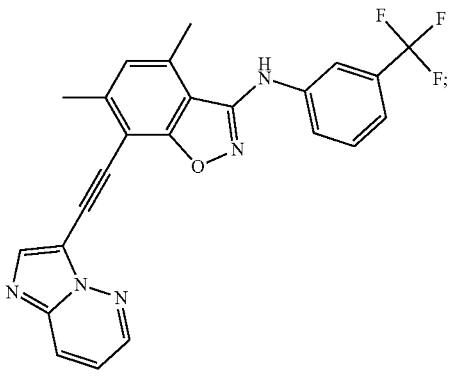

7-(imidazo[1,2-b]pyridazin-3-ylethynyl)-4,6-dimethyl-N-(3-(trifluoromethyl)phenyl)benzo[d]isoxazol-3-amine -continued Compound 12

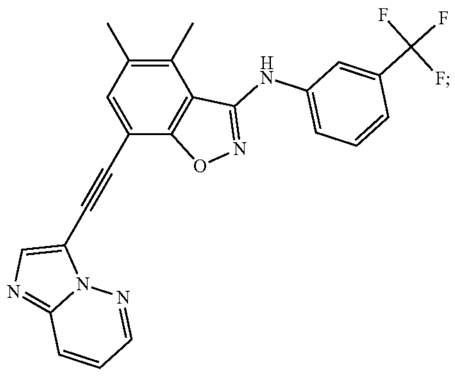

7-(imidazo[1,2-b]pyridazin-3-ylethynyl)-4,5-dimethyl-N-(3-(trifluoromethyl)phenyl)benzo[d]isoxazol-3-amine Compound 13

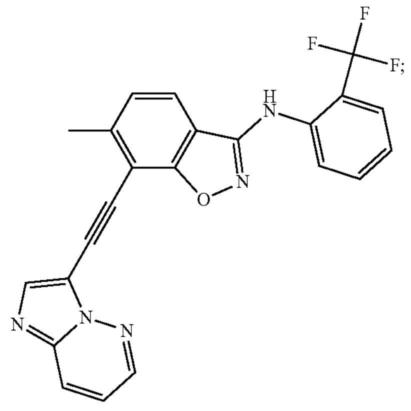

7-(imidazo[1,2-b]pyridazin-3-ylethynyl)-6-methyl-N-(2-(trifluoromethyl)phenyl)benzo[d]isoxazol-3-amine Compound 15

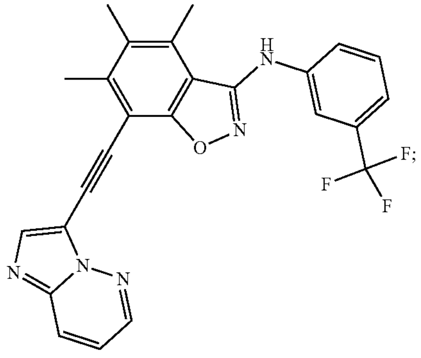

7-(imidazo[1,2-b]pyridazin-3-ylethynyl)-6-methyl-N-(4-(trifluoromethyl)phenyl)benzo[d]isoxazol-3-amine -continued Compound 14

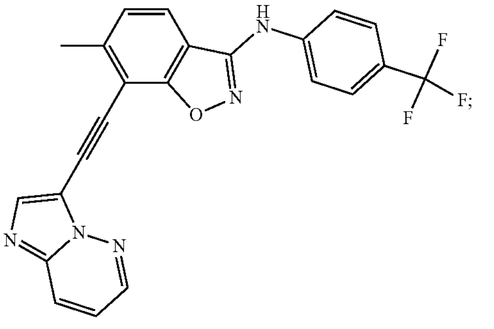

7-(imidazo[1,2-b]pyridazin-3-ylethynyl)-6-methyl-N-(4-(trifluoromethyl)phenyl)benzo[d]isoxazol-3-amine Compound 15

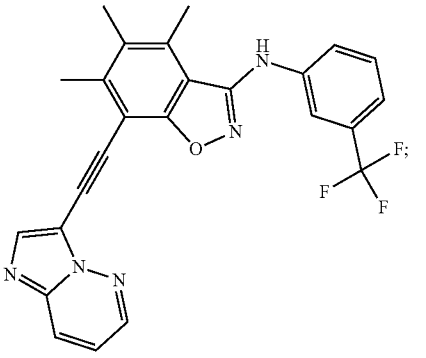

7-(imidazo[1,2-b]pyridazin-3-ylethynyl)-4,5,6-trimethyl-N-(3-(trifluoromethyl)phenyl)benzo[d]isoxazol-3-amine Compound 16

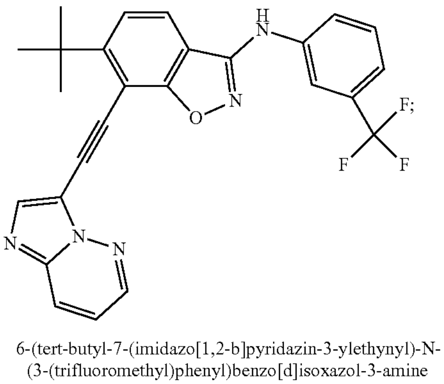

6-(tert-butyl-7-(imidazo[1,2-b]pyridazin-3-ylethynyl)-N-(3-(trifluoromethyl)phenyl)benzo[d]isoxazol-3-amine -continued Compound 17

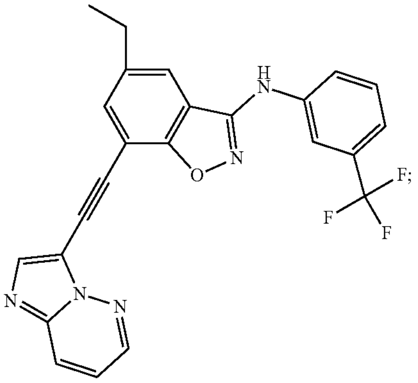

5-ethyl-7-(imidazo[1,2-b]pyridazin-3-ylethynyl)-N-(3-(trifluoromethyl)phenyl)benzo[d]isoxazol-3-amine Compound 18

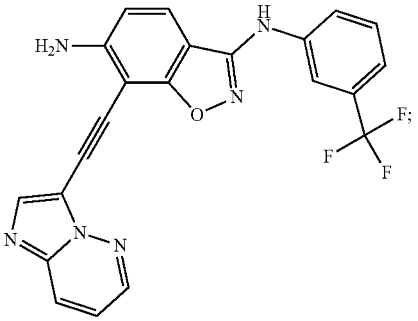

7-(imidazo[1,2-b]pyridazin-3-ylethynyl)-$N^3$-(3-(trifluoromethyl)phenyl)benzo[d]isoxazole-3,6-diamine Compound 19

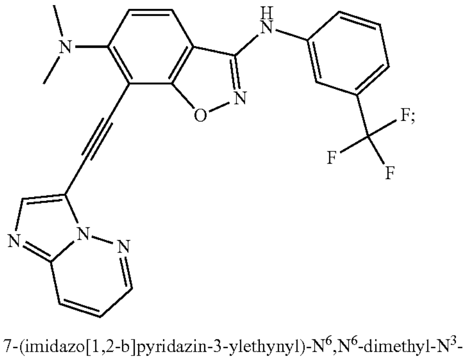

7-(imidazo[1,2-b]pyridazin-3-ylethynyl)-$N^6$,$N^6$-dimethyl-$N^3$-(3-(trifluoromethyl)phenyl)benzo[d]isoxazole-3,6-diamine -continued Compound 20

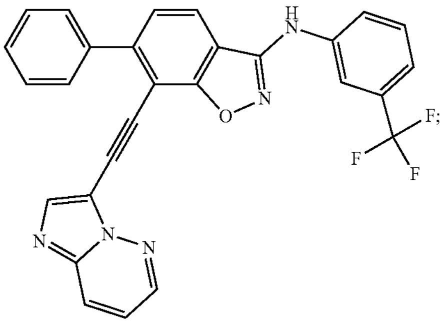

7-(imidazo[1,2-b]pyridazin-3-ylethynyl)-6-phenyl-N-(3-(trifluoromethyl)phenyl)benzo[d]isoxazol-3-amine Compound 21

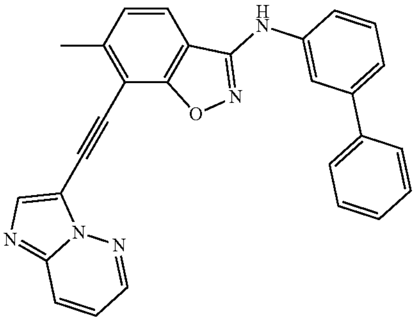

;

N-([1,1'-biphenyl]-3-yl)-7-(imidazo[1,2-b]pyridazin-3-ylethynyl)-6-methylbenzo[d]isoxazol-3-amine Compound 22

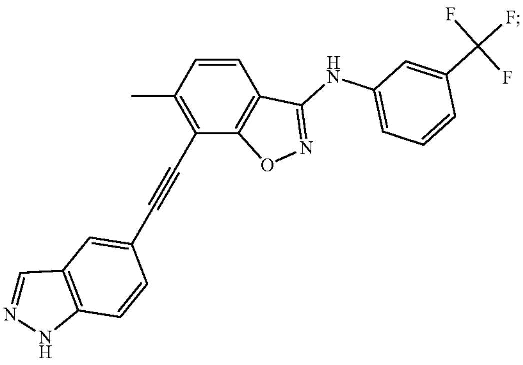

7-((1H-indazol-5-yl)ethynyl)-6-methyl-N-(3-(trifluoromethyl)phenyl)benzo[d]isoxazol-3-amine -continued Compound 23

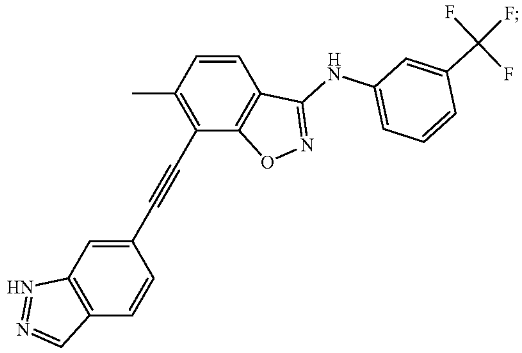

7-((1H-indazol-6-yl)ethynyl)-6-methyl-N-(3-(trifluoromethyl)phenyl)benzo[d]isoxazol-3-amine Compound 24

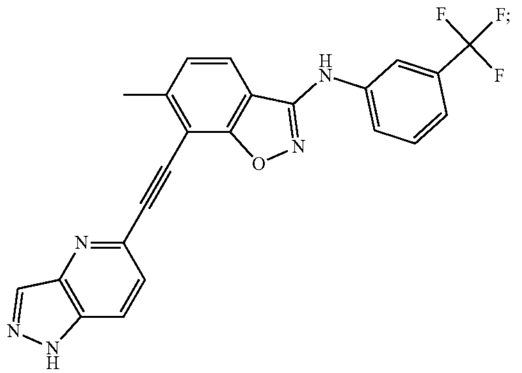

7-((1H-pyrazolo[4,3-b]pyridin-5-yl)ethynyl)-6-methyl-N-(3-(trifluoromethyl)phenyl)benzo[d]isoxazol-3-amine Compound 25

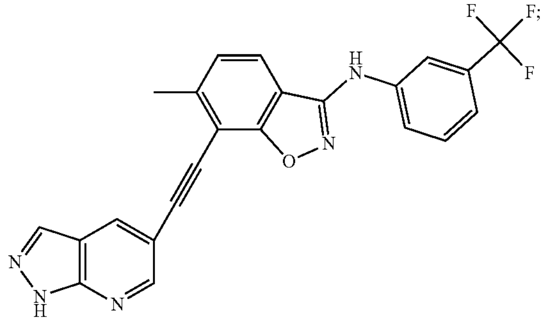

7-((1H-pyrazolo[3,4-b]pyridin-5-yl)ethynyl)-6-methyl-N-(3-(trifluoromethyl)phenyl)benzo[d]isoxazol-3-amine -continued Compound 26

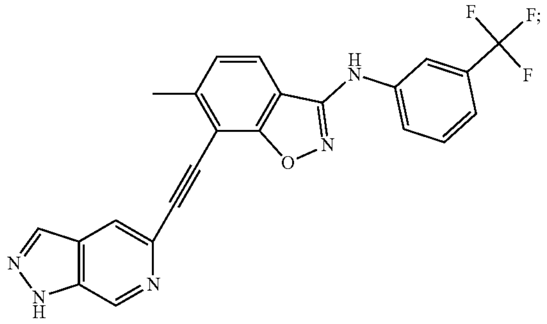

7-((1H-pyrazolo[3,4-c]pyridin-5-yl)ethynyl)-6-methyl-N-(3-(trifluoromethyl)phenyl)benzo[d]isoxazol-3-amine Compound 27

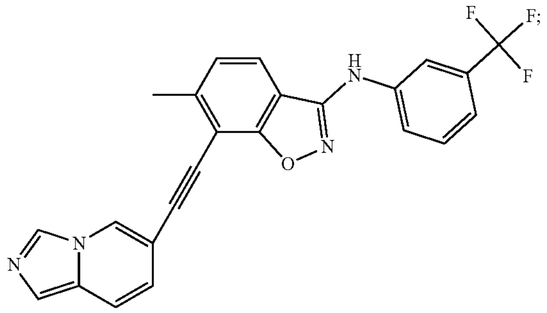

7-(imidazo[1,5-a]pyridin-6-ylethynyl)-6-methyl-N-(3-(trifluoromethyl)phenyl)benzo[d]isoxazol-3-amine Compound 28

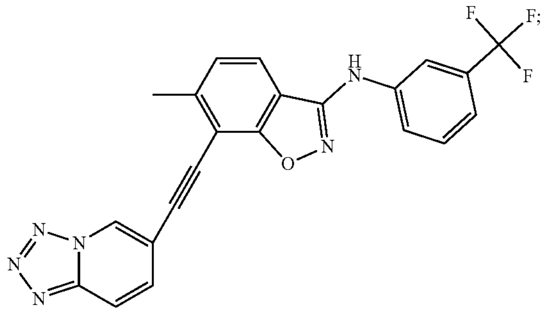

6-methyl-7-(tetrazolo[1,5-a]pyridin-6-ylethynyl)-N-(3-(trifluoromethyl)phenyl)benzo[d]isoxazol-3-amine Compound 29

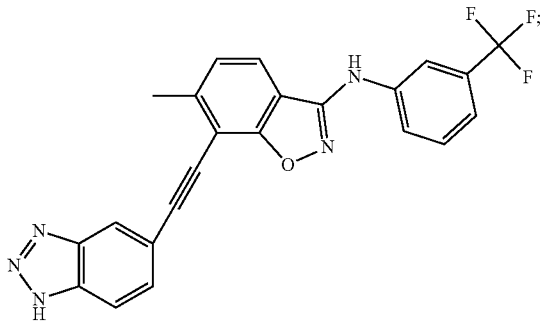

7-((1H-benzo[d][1,2,3]triazol-5-yl)ethynyl)-6-methyl-N-(3-(trifluoromethyl)phenyl)benzo[d]isoxazol-3-amine -continued Compound 30

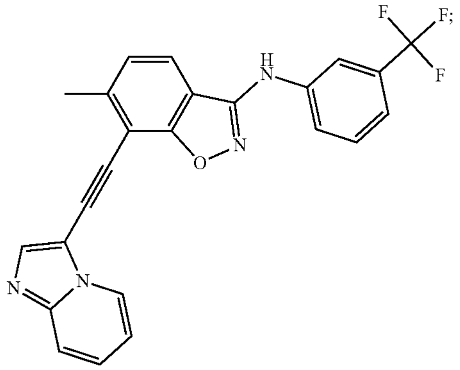

7-(imidazo[1,2-a]pyridin-3-ylethynyl)-6-methyl-N-(3-(trifluoromethyl)phenyl)benzo[d]isoxazol-3-amine Compound 31

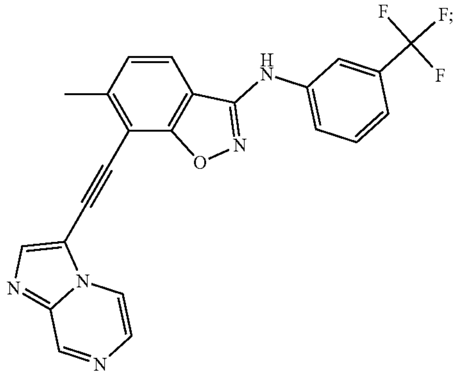

7-(imidazo[1,2-a]pyrazin-3-ylethynyl)-6-methyl-N-(3-(trifluoromethyl)phenyl)benzo[d]isoxazol-3-amine Compound 32

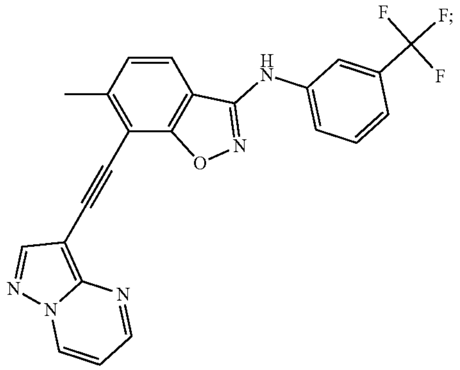

6-methyl-7-(pyrazolo[1,5-a]pyrimidin-3-ylethynyl)-N-(3-(trifluoromethyl)phenyl)benzo[d]isoxazol-3-amine -continued Compound 33

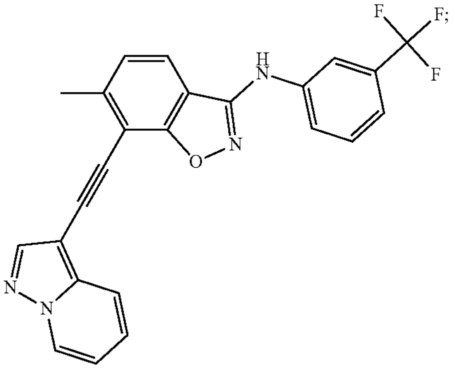

6-methyl-7-(pyrazolo[1,5-a]pyridin-3-ylethynyl)-N-(3-(trifluoromethyl)phenyl)benzo[d]isoxazol-3-amine Compound 34

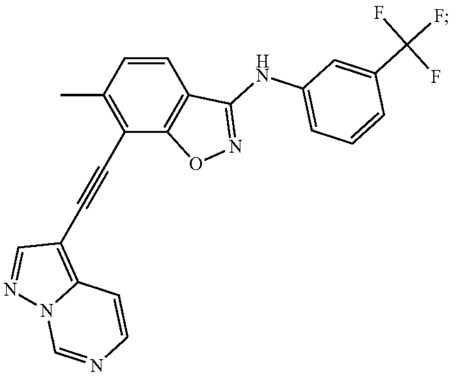

6-methyl-7-(pyrazolo[1,5-c]pyrimidin-3-ylethynyl)-N-(3-(trifluoromethyl)phenyl)benzo[d]isoxazol-3-amine Compound 35

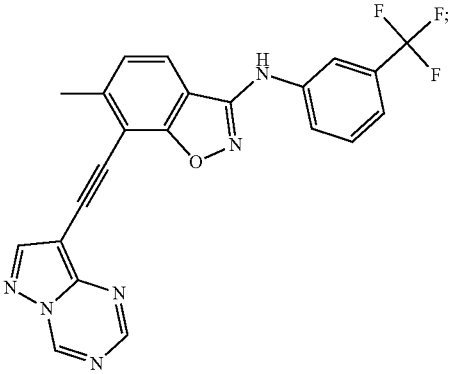

6-methyl-7-(pyrazolo[1,5-a][1,3,5]triazin-8-ylethynyl)-N-(3-(trifluoromethyl)phenyl)benzo[d]isoxazol-3-amine -continued Compound 36

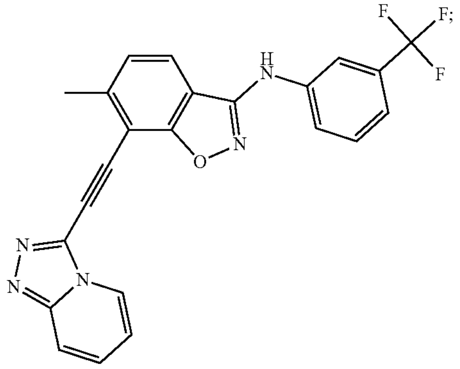

7-([1,2,4]triazolo[4,3-a]pyridin-3-ylethynyl)-6-methyl-N-(3-(trifluoromethyl)phenyl)benzo[d]isoxazol-3-amine Compound 37

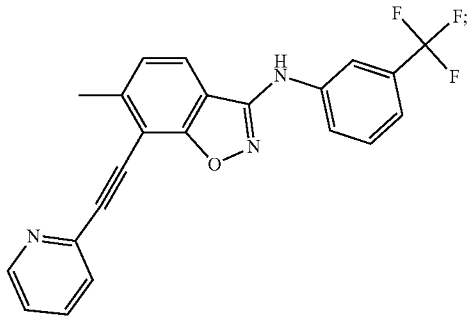

6-methyl-7-(pyridin-2-ylethynyl)-N-(3-(trifluoromethyl)phenyl)benzo[d]isoxazol-3-amine Compound 38

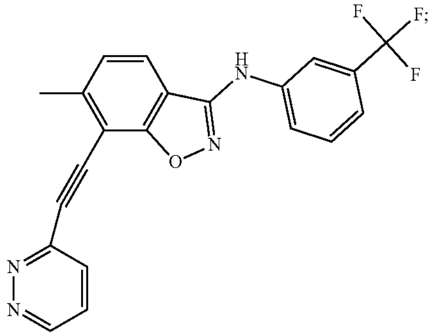

6-methyl-7-(pyridazin-3-ylethynyl)-N-(3-(trifluoromethyl)phenyl)benzo[d]isoxazol-3-amine Compound 39

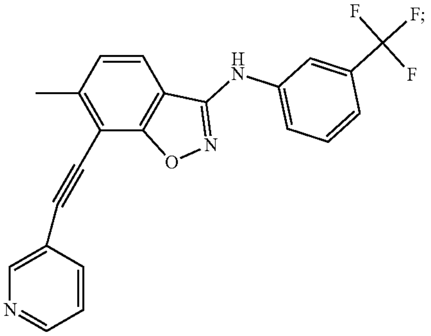

6-methyl-7-(pyridin-3-ylethynyl)-N-(3-(trifluoromethyl)phenyl)benzo[d]isoxazol-3-amine Compound 40

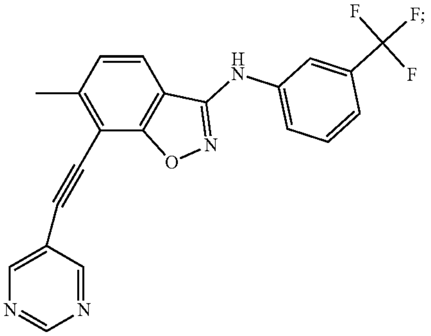

6-methyl-7-(pyrimidin-5-ylethynyl)-N-(3-(trifluoromethyl)phenyl)benzo[d]isoxazol-3-amine Compound 41

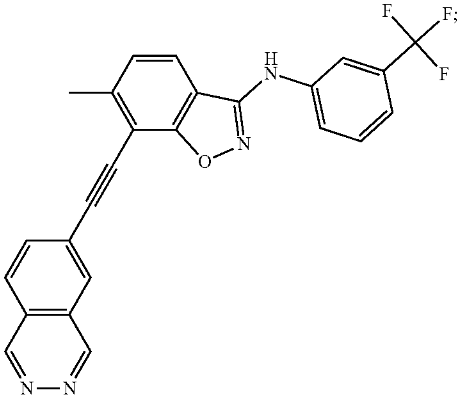

6-methyl-7-(phthalazin-6-ylethynyl)-N-(3-(trifluoromethyl)phenyl)benzo[d]isoxazol-3-amine Compound 42

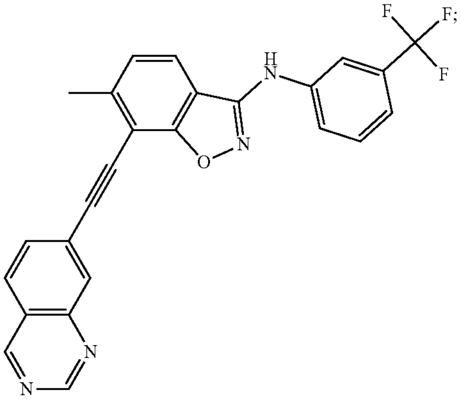

6-methyl-7-(quinazolin-7-ylethynyl)-N-(3-(trifluoromethyl)phenyl)benzo[d]isoxazol-3-amine Compound 43

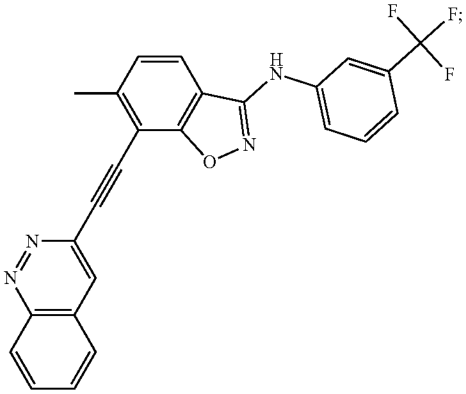

7-(cinnolin-7-ylethynyl)-6-methyl-N-(3-(trifluoromethyl)phenyl)benzo[d]isoxazol-3-amine Compound 44

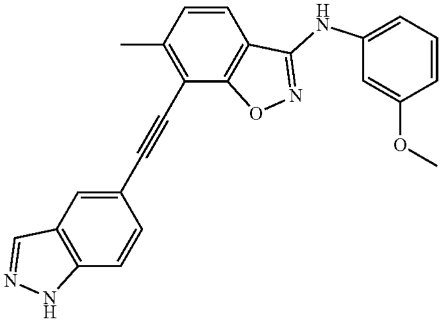

;

7-((1H-indazol-5-yl)ethynyl)-N-(3-methoxyphenyl)-6-methylbenzo[d]isoxazol-3-amine -continued Compound 45

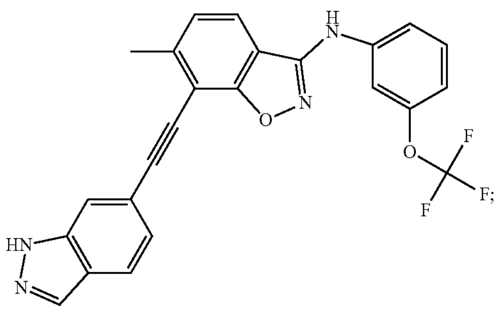

7-((1H-indazol-6-yl)ethynyl)-6-methyl-N-(3-(trifluoromethoxy)phenyl)benzo[d]isoxazol-3-amine Compound 46

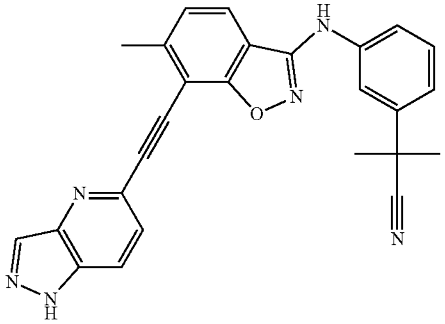

;

2-(3-((7-((1H-pyrazolo[4,3-b]pyridin-5-yl)ethynyl)-6-methylbenzo[d]isoxazol-3-yl)amino)phenyl)-2-methylpropanenitrile Compound 47

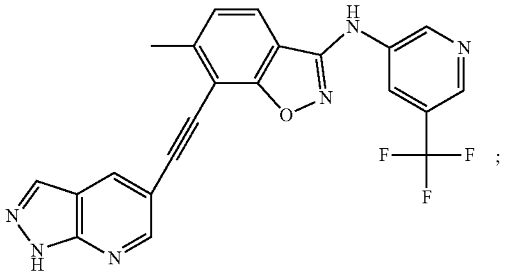

;

7-((1H-pyrazolo[3,4-b]pyridin-5-yl)ethynyl)-6-methyl-N-(5-trifluoromethyl)pyridin-3yl)benzo[d]isoxazol-3-amine Compound 48

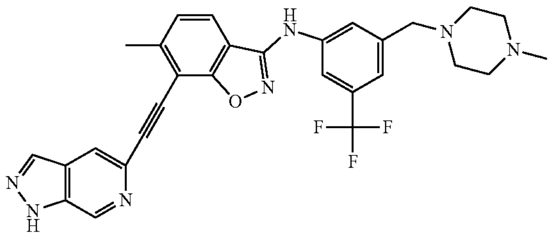

;

7-((1H-pyrazolo[3,4-c]pyridin-5-yl)ethynyl)-6-methyl-N-(3-((4-methylpiperazin-1-yl)methyl)-5-(trifluorometh1)phenyl)benzo[d]isoxazol-3-amine -continued Compound 49

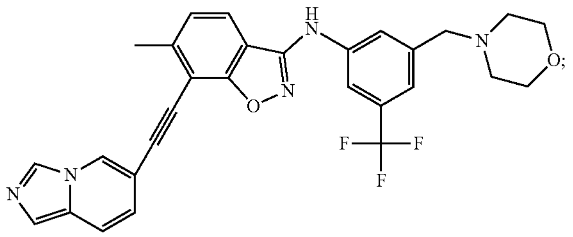

7-(imidazo[1,5-a]pyridin-6-ylethynyl)-6-methyl-N-(3-(morpholinomethyl)-5-(trifluorometh1)phenyl)benzo[d]isoxazol-3-amine Compound 50

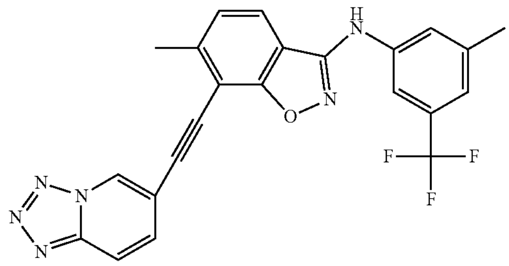

;

6-methyl-N-(3-methyl-5-(trifluoromethyl)phenyl)-7-(tetrazolo[1,5-a]pyridin-6-ylethynyl)benzo[d]isoxazol-3-amine Compound 51

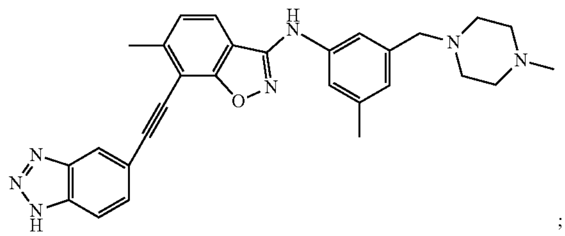

;

7-((1H-benzo[d][1,2,3]triazol-5-yl)ethynyl)-6-methyl-N-(3-methyl-5-((4-methylpiperazin-1-yl)methyl)phenyl)benzo[d]isoxazol-3-amine Compound 52

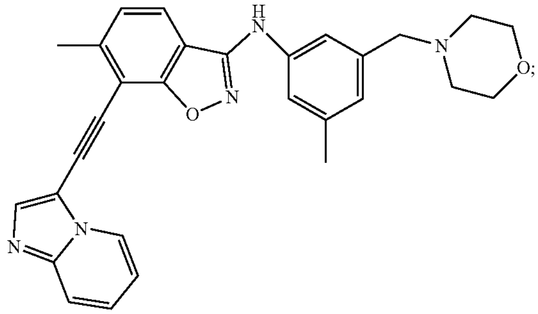

7-(imidazo[1,2-a]pyridin-3-ylethynyl)-6-methyl-N-(3-methyl-5-(morpholinomethyl)phenyl)benzo[d]isoxazol-3-amine -continued Compound 53

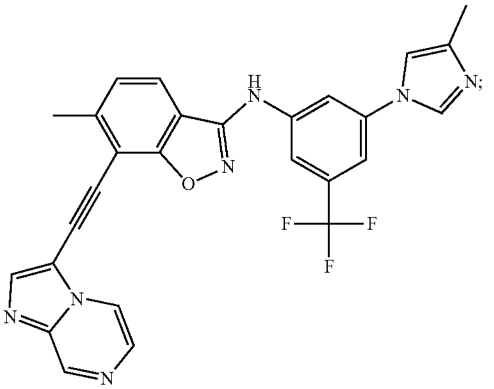

7-(imidazo[1,2-a]pyrazin-3-ylethynyl)-6-methyl-N-(3-(4-methyl-1H-imidazol-1-yl)-5-(trifluoromethyl)phenyl)benzo[d]isoxazol-3-amine Compound 54

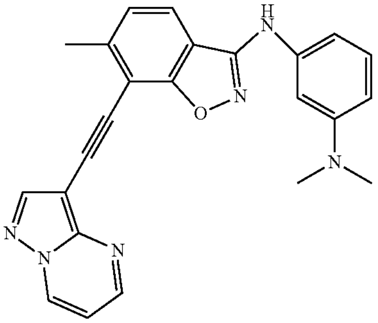

;

$N^1$,$N^1$-dimethyl-$N^3$-(6-methyl-7-(pyrazolo[1,5-a]pyrimidin-3-ylethynyl)benzo[d]isoxazol-3-yl)benzene-1,3-diamine Compound 55

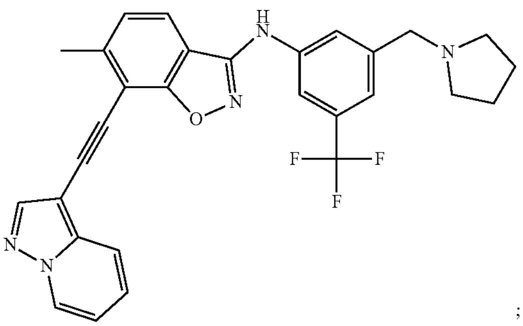

;

6-methyl-7-(pyrazolo[1,5-a]pyridin-3ylethynyl)-N-(3-(pyrrolidin-1-ylmethyl)-5-(trifluoromethyl)phenyl)benzo[d]isoxazol-3-amine -continued Compound 56

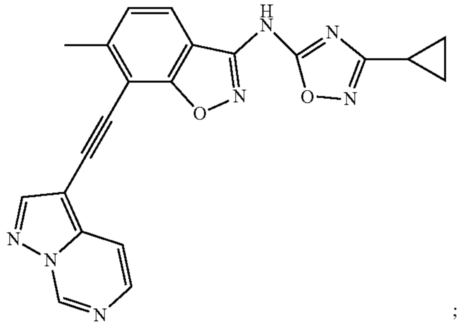

;

N-(3-cyclopropyl-1,2,4-oxadiazol-5-yl)-6-methyl-7-(pyrazolo[1,5-c]pyrimidin-3-ylethynyl)benzo[d]isoxazol-3-amine Compound 57

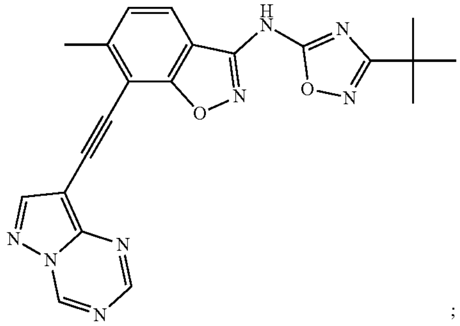

;

N-(3-(tert-butyl)-1,2,4-oxadiazol-5-yl)-6-methyl-7-(pyrazolo[1,5-a][1,3,5]triazin-8-ylethynyl)benzo[d]isoxazol-3-amine Compound 58

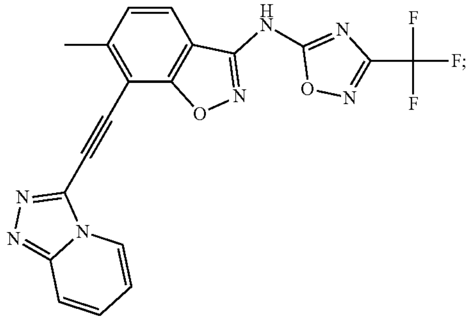

7-([1,2,4]triazolo[4,3-a]pyridin-3-ylethynyl-6-methyl-N-(3-trifluoromethyl-1,2,4-oxodiazol-5-yl)benzo[d]isoxazol-3-amine -continued Compound 59

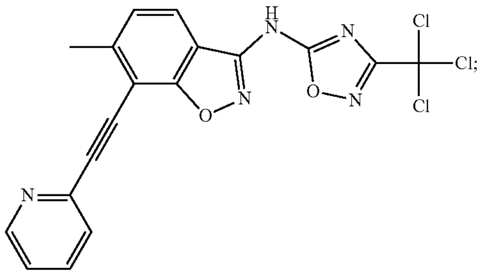

6-methyl-7-(pyridin-2-ylethynyl)-N-(3-(trichloromethyl)-1,2,4-oxadiazol-5-yl)benzo[d]isoxazol-3-amine Compound 60

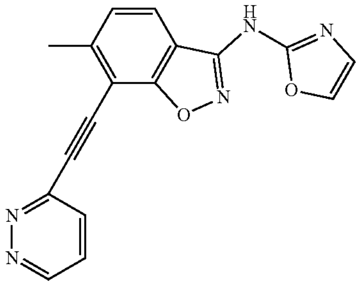

;

6-methyl-N-(oxazol-2-yl)-7-(pyridazin-3-ylethynyl)benzo[d]isoxazol-3-amine

Compound 61

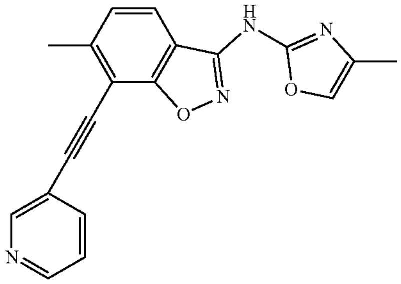

;

6-methyl-N-(4-methyloxazol-2-yl)-7-(pyridin-3-ylethynyl)benzo[d]isoxazol-3-amine Compound 62

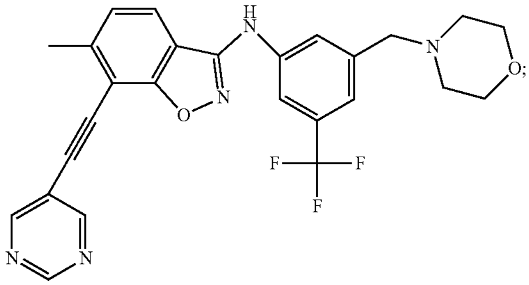

6-methyl-N-(3-(morpholinomethyl)-5-(trifluoromethyl)phenyl)-7-(pyrimidin-5-ylethynyl)benzo[d]isoxazol-3-amine -continued Compound 63

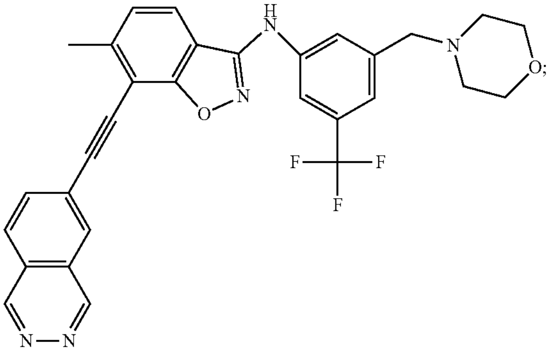

6-methyl-N-(3-(morpholinomethyl)-5-(trifluoromethyl)phenyl)-7-(phthalazin-6-ylethynyl)benzo[d]isoxazol-3-amine Compound 64

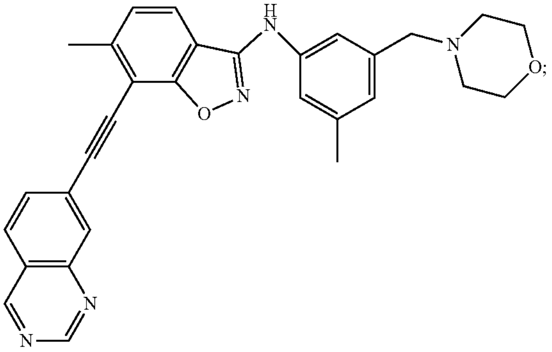

6-methyl-N-(3-methyl-5-(morpholinomethyl)phenyl)-7-(quinazolin-y-ylethynyl)benzo[d]isoxazol-3-amine Compound 65

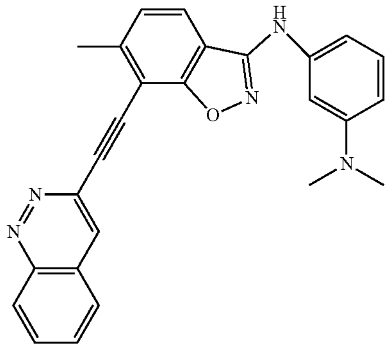

;

$N^1$-(7-(cinnolin-3-ylethynyl)-6-methylbenzo[d]isoxazol-3-yl)-$N^3$,$N^3$-dimethylbenzene-1,3-diamine -continued Compound 66

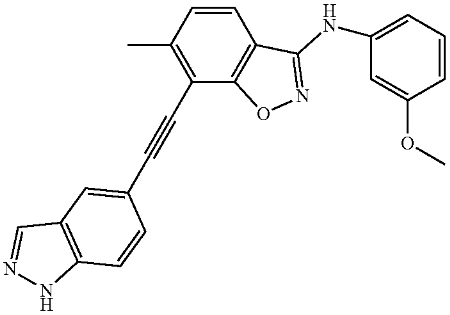

;

7-((1H-indazol-5-yl)ethynyl)-N-(3-methoxyphenyl)-6-methylbenzo[d]isoxazol-3-amine Compound 67

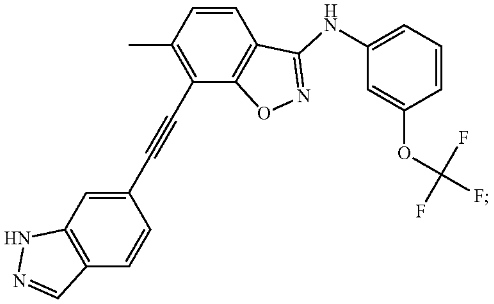

7-((1H-indazol-6-yl)ethynyl)-6-methyl-N-(3-(trifluoromethoxy)phenyl)benzo[d]isoxazol-3-amine Compound 68

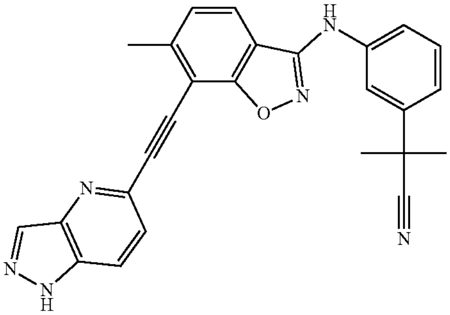

;

2-(3-((7-((1H-pyrazolo[4,3-b]pyridin-5-yl)ethynyl)-6-methylbenzo[d]isoxazol-3-yl)amino)phenyl)-2-methylpropanenitrile Compound 69

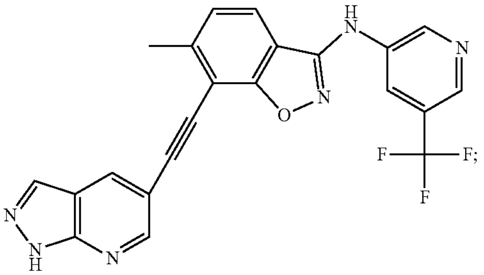

7-((1H-pyrazolo[3,4-b]pyridin-5-yl)ethynyl)-6-methyl-N-(5-(trifluoromethyl)pyridin-3-yl)benzo[d]isoxazol-3-amine -continued Compound 70

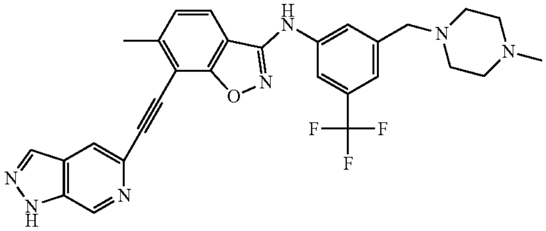

;

7-((1H-pyrazolo[3,4-c]pyridin-5-yl)ethynyl)-6-methyl-N-(3-((4-methylpiperazin-1-yl)methyl)-5-(trifluoromethyl)phenyl)benzo[d]isoxazol-3-amine Compound 71

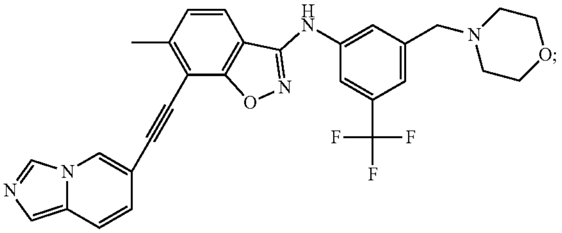

7-(imidazo[1,5-1]pyridin-6-ylethynyl)-6-methyl-N-(3-(morpholinomethyl)-5-(trifluoromethyl)phenyl)benzo[d]isoxazol-3-amine Compound 72

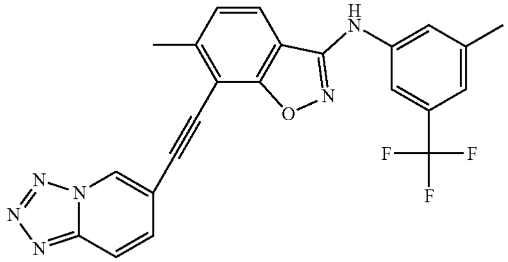

;

6-methyl-N-(3-methyl-5-(trifluoromethyl)phenyl)-7-(tetrazolo[1,5-a]pyridin-6-ylethynyl)benzo[d]isoxazol-3-amine Compound 73

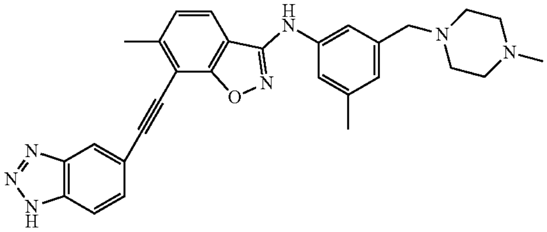

;

7-((1H-benzo[d][1,2,3]triazol-5-yl)ethynyl)-6-methyl-N-(3-methyl-5-((4-methylpiperazin-1-yl)methyl)phenyl)benzo[d]isoxazol-3-amine -continued Compound 74

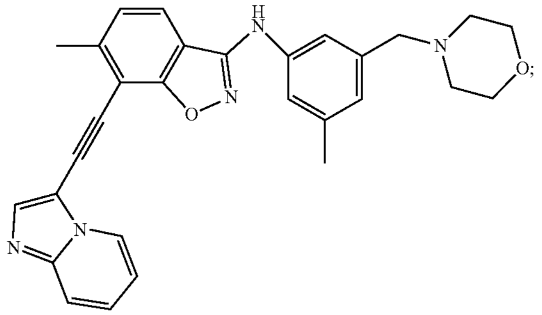

7-(imidazo[1,2-a]pyridin-3-ylethynyl)-6-methyl-N-(3-methyl-5-(morpholinomethyl)phenyl)benzo[d]isoxazol-3-amine Compound 75

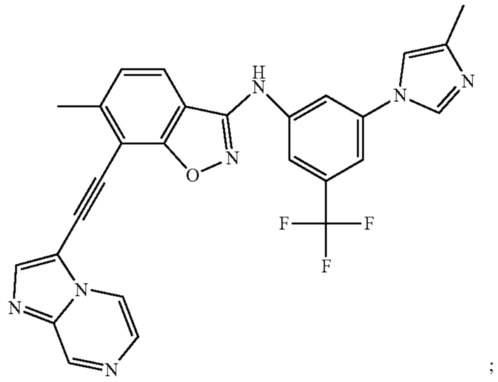

;

7-(imidazo[1,2-a]pyrazin-3-ylethynyl)-6-methyl-N-(3-(4-methyl-1H-imidazol-1-yl)-5-(trifluoromethyl)phenyl)benzo[d]isoxazol-3-amine Compound 76

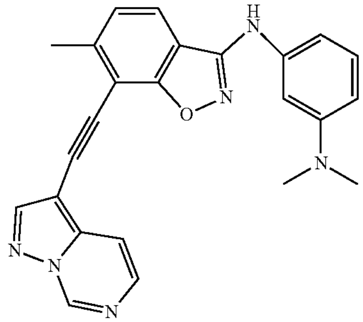

;

$N^1$,$N^1$-dimethyl-$N^3$-(6-methyl-7-(pyrazolo[1,5-a]pyrimidin-3-ylethynyl)benzo[d]isoxazol-3-yl)benzxene-1,3-diamine -continued Compound 77

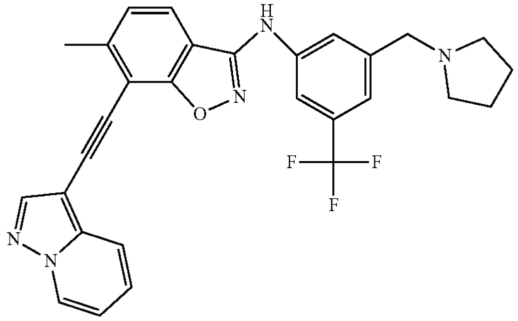

;

6-methyl-7-(pyrazolo[1,5-a]pyridin-3-ylethynyl)-N-(3-(pyrrolidin-1-ylmethyl)-5-(trifluoromethyl)phenyl)benzo[d]isoxazol-3-amine Compound 78

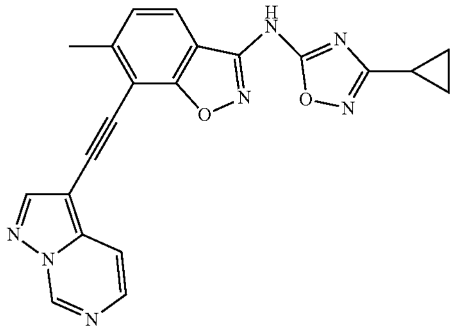

;

N-(3-cyclopropyl-1,2,4-oxadiazol-5-yl)-6-methyl-7-(pyrazolo[1,5-c]pyrimidin-3-ylethynyl)benzo[d]isoxazol-3-amine Compound 79

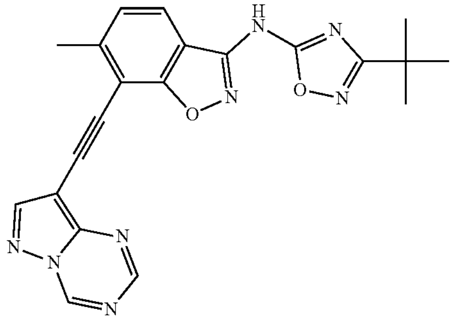

;

N-(3-(tert-butyl)-1,2,4-oxadiazol-5-yl)-6-methyl-7-(pyrazolo[1,5-a][1,3,5]triazin-8-ylethynyl)benzo[d]isoxazol-3-amine -continued Compound 80

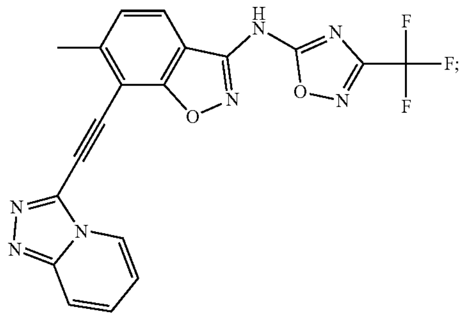

7-([1,2,4]triazolo[4,3-a]pyridin-3-ylethynyl)-6-methyl-N-(3-(trifluoromethyl)-1,2,4-oxadiazol-5-yl)benzo[d]isoxazol-3-amine Compound 81

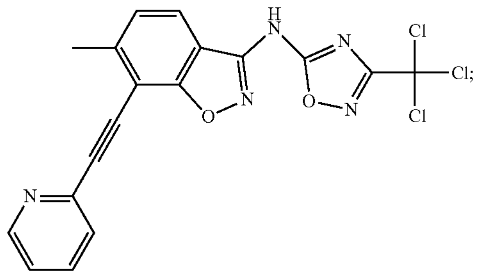

6-methyl-7-(pyridin-2-ylethynyl)-N-(3-(trichloromethyl)-1,2,4-oxadiazol-5-yl)benzo[d]isoxazol-3-amine Compound 82

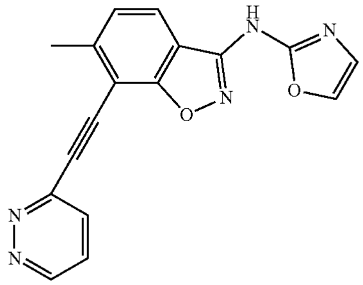

;

6-methyl-N-(oxazol-2-yl)-7-(pyridazin-3-ylethynyl)benzo[d]isoxazol-3-amine

Compounmd 83

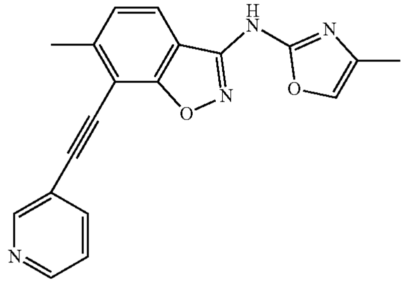

;

6-methyl-N-(4-methyloxazol-2-yl)-7-(pyridin-3-ylethynyl)benzo[d]isoxazol-3-amine -continued Compound 84

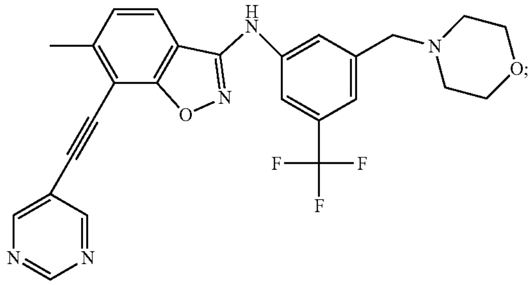

6-methyl-N-(3-morpholinomethyl)-5-(trifluoromethyl)phenyl)-7-(pyrimidin-5-ylethynyl)benzo[d]isoxazol-3-amine Compound 85

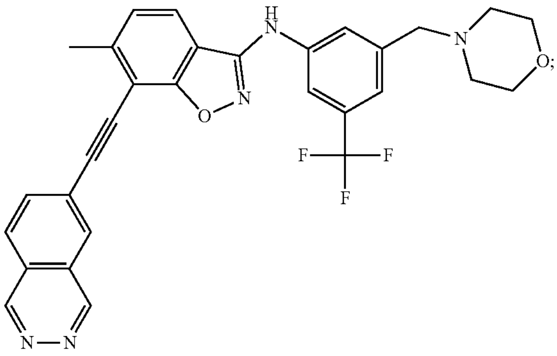

6-methyl-N-(3-morpholinomethyl)-5-(trifluoromethyl)phenyl)-7-(phthalazin-6-ylethynyl)benzo[d]isoxazol-3-amine Compound 86

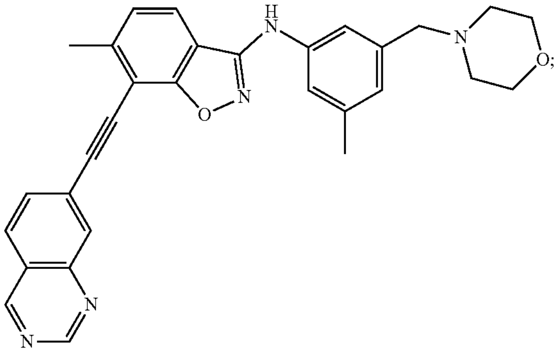

6-methyl-N-(3-methyl-5-(morpholinomethyl)phenyl)-7-(quinazolin-7-ylethynyl)benzo[d]isoxazol-3-amine -continued Compound 87

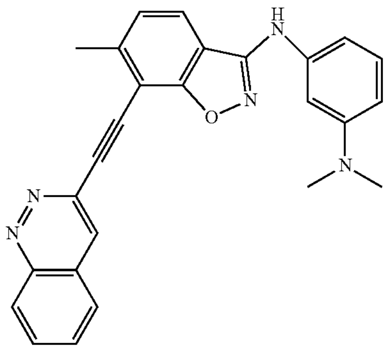

;

$N^1$-(7-(cinnolin-3-ylethynyl)-6-methylbenzo[d]isoxazol-3-yl)-$N^3$,$N^3$-dimethylbenzene-1,3-diamine Compound 88

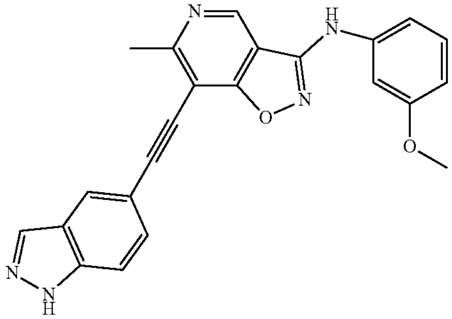

;

7-((1H-indazol-5-yl)ethynyl)-N-(3-methoxyphenyl)-6-methylisoxazolo[4,5-c]pyridin-3-amine Compound 89

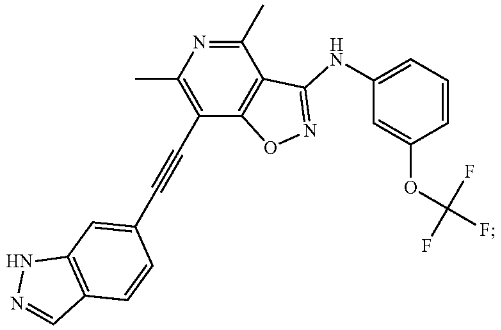

7-((1H-indazol-6-yl)ethynyl)-4,6-dimethyl-N-(3-(trifluoromethoxy)phenyl)isoxazolo[4,5-c]pyridin-3-amine -continued Compound 90

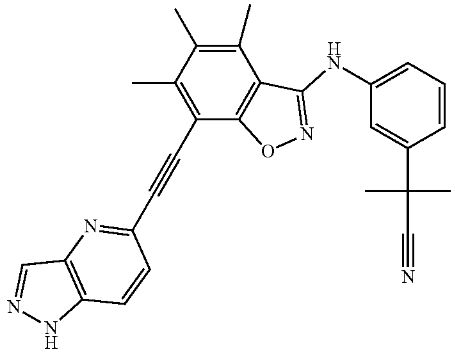

;

2-(3-((7-((1H-pyrazolo[4,3-b]pyridin-5-yl)ethynyl)-4,5,6-trimethylbenzofuran-3-yl)amino)phenyl)-2-methylpropanenitrile Compound 91

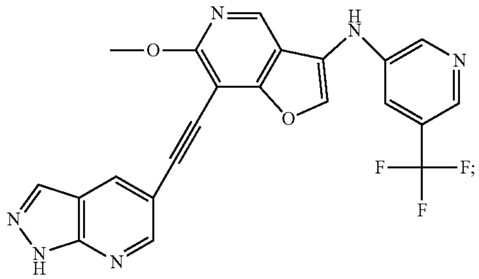

7-((1H-pyrazolo[3,4-b]pyridin-5-yl)ethynyl)-6-methoxy-N-(5-(trifluoromethyl)pyridin-3-yl)furo[3,2-c]pyridin-3-amine Compound 92

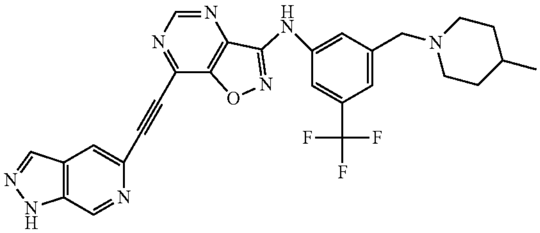

;

7-((1H-pyrazolo[3,4-c]pyridin-5-yl)ethynyl)-N-(3-((4-methylpiperazin-1-yl)methyl)-5-(trifluoromethyl)phenyl)isoxazolo[4,5-d]pyrimidin-3-amine Compound 93

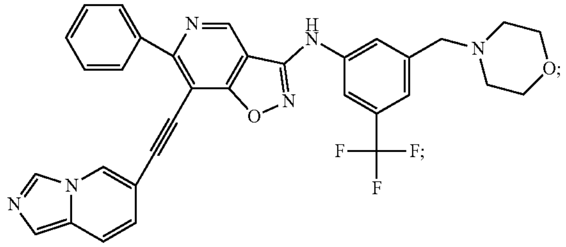

7-(imidazo[1,5-a]pyridin-6-ylethynyl)-N-(3-(morpholinomethyl)-5-(trifluoromethyl)phenyl)-6-phenylisoxazolo[4,5-c]pyridin-3-amine -continued Compound 94

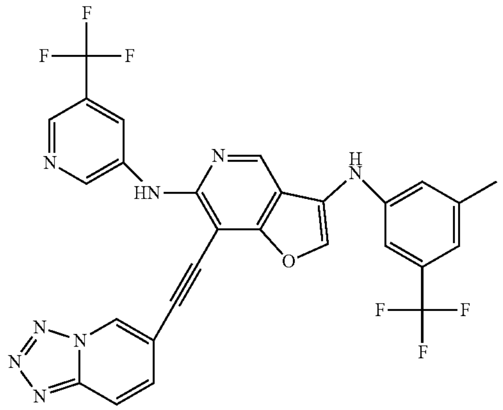

;

$N^3$-(3-methyl-5-(trifluoromethyl)phenyl)-7-(tetrazolo[1,5-a]pyridin-6-ylethynyl)-$N^6$-(5-(trifluoromethyl)pyridin-3-yl)isoxazolo[4,5-b]pyridine-3,6-diamine Compound 95

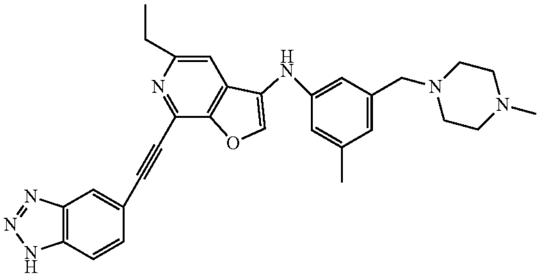

;

7-((1H-benzo[d][1,2,3]triazol-5-yl)ethynyl)-5-ethyl-N-(3-methyl-5-((4-methylpiperazin-1-yl)methyl)phenyl)furo[2,3-c]pyridin-3-amine Compound 96

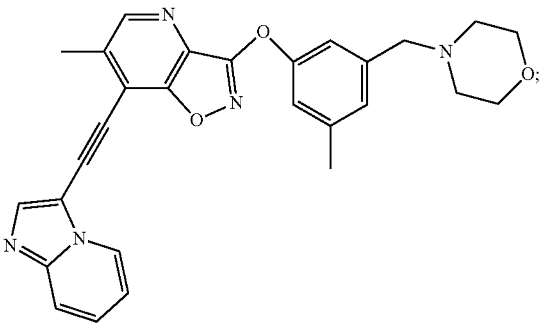

;

7-(imidazo[1,2-a]pyridin-3-ylethynyl)-6-methyl-3-(3-methyl-5-(morpholinomethyl)phenoxy)isoxazolo[4,5-b]pyridine -continued Compound 97

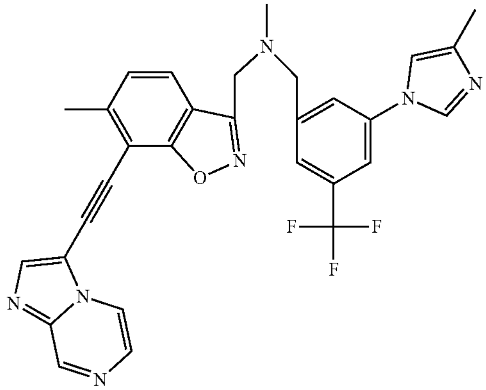

;

1-(7-(imidazo[1,2-a]pyrazin-3-ylethynyl)-6-methylbenzo[d]isoxazol-3-yl)-N-methyl-N-(3-(4-methyl-1H-imidazol-1-yl)-5-(trifluoromethyl)benzyl)methanamine Compound 98

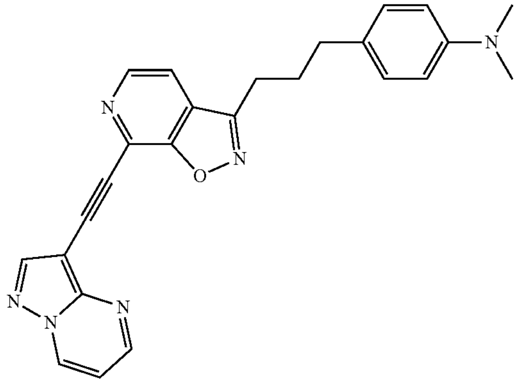

;

N,N-dimethyl-4-(3-(7-(pyrazolo[1,5-a]pyrimidin-3-ylethynyl)isoxazolo[5,4-c]pyridin-3-yl)propyl)aniline Compound 99

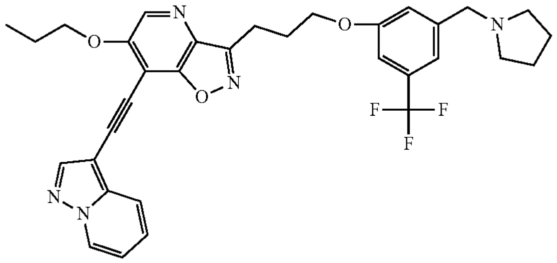

;

6-propoxy-7-(pyrazolo[1,5-a]pyridin-3-ylethynyl)-3-(3-(3-(pyrrolidin-1-ylmethyl)-5-(trifluoromethyl)phenoxy)propyl)isoxazolo[4,5-b]pyridine -continued Compound 100

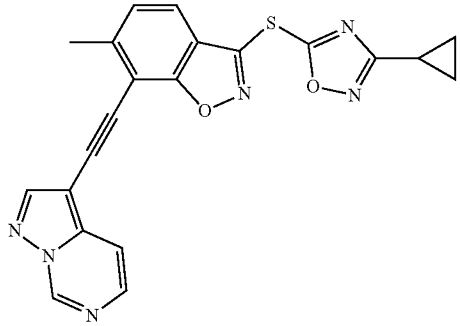

;

3-((3-cyclopropyl-1,2,4-oxadiazol-5-yl)thio)-6-methyl-7-(pyrazolo[1,5-c]pyrimidin-3-ylethynyl)benzo[d]isoxazole Compound 101

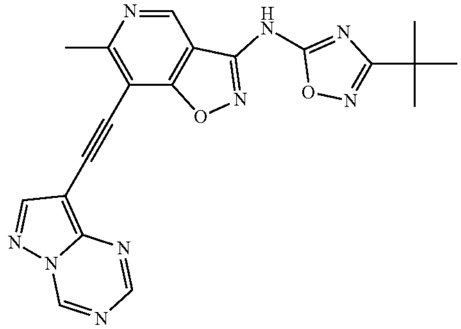

;

N-(3-(tert-butyl)-1,2,4-oxadiazol-5-yl)-6-methyl-7-(pyrazolo[1,5-a][1,3,5]triazin-8-ylethynyl)isoxazolo[4,5-c]pyridin-3-amine Compound 102

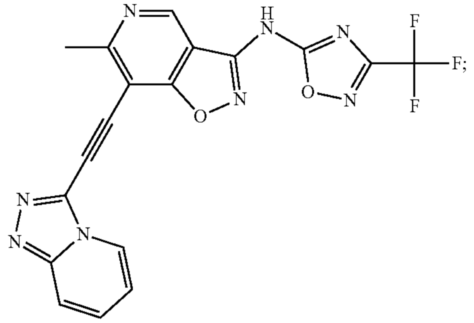

7-([1,2,4]triazolo[4,3-a]pyridin-3-ylethynyl)-6-methyl-N-(3-(trifluoromethyl)-1,2,4-oxadiazol-5-yl)isoxazolo[4,5-c]pyridin-3-amine -continued Compound 103

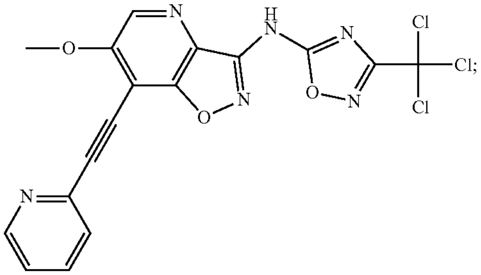

6-methoxy-7-(pyridin-2-ylethynyl)-N-(3-(trichloromethyl)-1,2,4-oxadiazol-5-yl)isoxazolo[4,5-b]pyridin-3-amine Compound 104

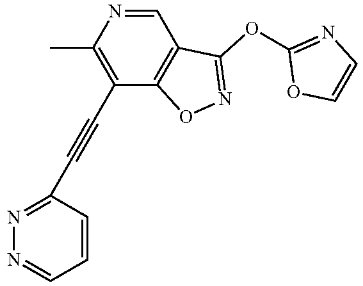

;

6-methyl-3-(oxazol-2-yloxy)-7-(pyridazin-3-ylethynyl)isoxazolo[4,5-c]pyridine

Compound 105

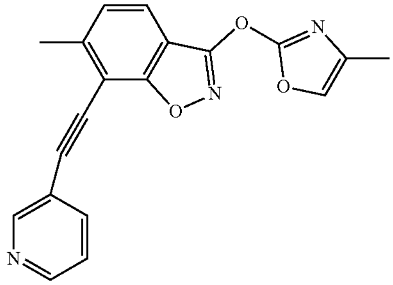

;

6-methyl-3-((4-methyloxazol-2-yl)oxy)-7-(pyridin-3-ylethynyl)benzo[d]isoxazole

Compound 106

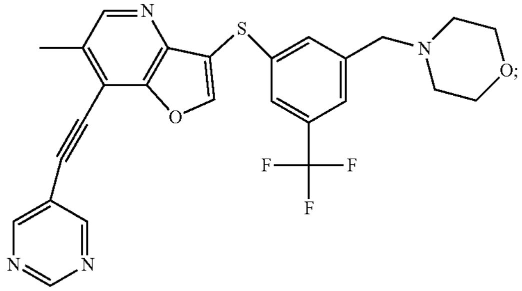

6-methyl-3-((3-(morpholinomethyl)-5-(trifluoromethyl)phenyl)thio)-7-(pyrimidin-5-ylethynyl)furo[3,2-b]pyridine -continued Compound 107

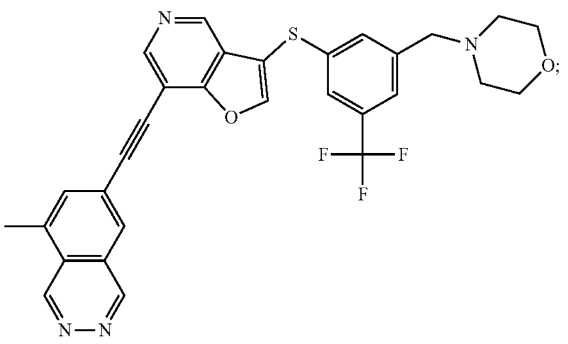

7-((8-methylphthalazin-6-yl)ethynyl)-3-((3-(morpholinomethyl)-5-(trifluoromethyl)phenyl)thio)furo[3,2-c]pyridine Compound 108

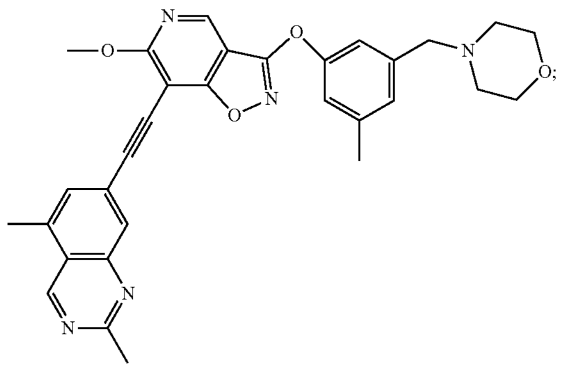

7-((2,5-dimethylquinazolin-7-yl)ethynyl)-6-methyloxy-3-(3-methyl-5-(morpholinomethyl)phenoxy)isoxazolo[4,5-c]pyridine Compound 109

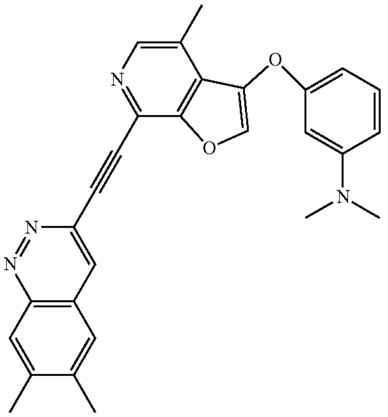

;

3-((7-((6,7-dimethylcinnolin-3-yl)ethynyl)-4-methylfuro[2,3-c]pyridin-3-yl)oxy)-N-N-dimethylaniline -continued Compound 110

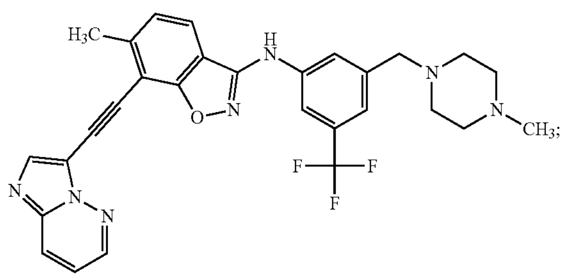

7-(imidazo[1,2-b]pyridazin-3-ylethynyl)-6-methyl-N-(3-((4-methylpiperazin-1-yl)methyl)-5-(trifluoromethyl)phenyl)benzo[d]isoxazol-3-amine Compound 111

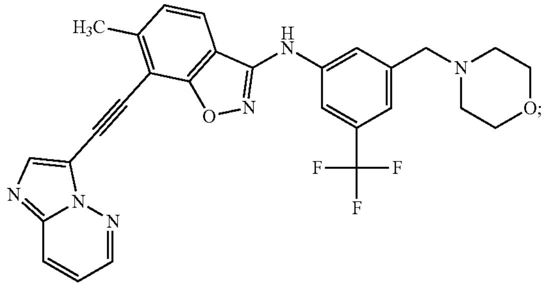

7-(imidazo[1,2-b]pyridazin-3-ylethynyl)-6-methyl-N-(3-(morpholinomethyl)-5-(trifluoromethyl)phenyl)benzo[d]isoxazol-3-amine Compound 112

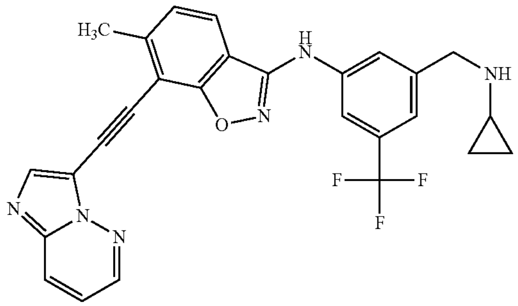

;

N-(3-((cyclopropylmino)methyl)-5-(trifluoromethyl)phenyl)-7-(imidazo[1,2-b]pyridazin-3-ylethynyl)-6-methylbenzo[d]isoxazol-3-amine Compound 113

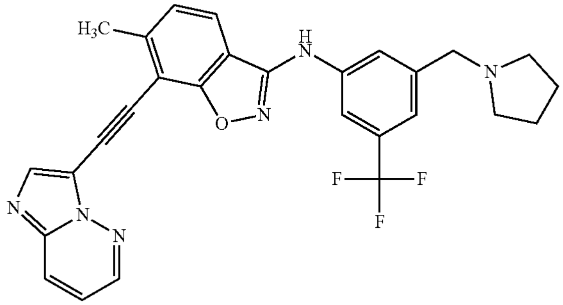

;

7-(imidazo[1,2-b]pyridazin-3-ylethynyl)-6-methyl-N-(3-(pyrrolidin-1-ylmethyl)-5-(trifluoromethyl)phenyl)-benzo[d]isoxazol-3-amine -continued Compound 114

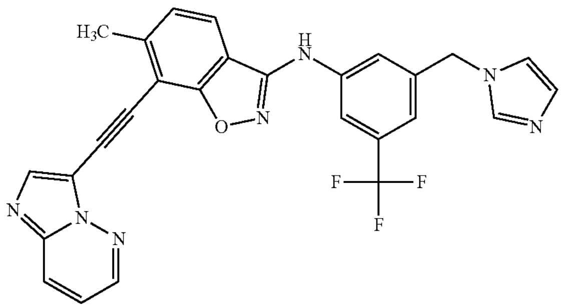

;

N-(3-((1H-(imidazol-1-yl)methyl)-5-(trifluoromethyl)phenyl)-7-(imidazo[1,2-b]pyridazin-3-ylethynyl)-6-methylbenzo[d]isoxazol-3-amine Compound 115

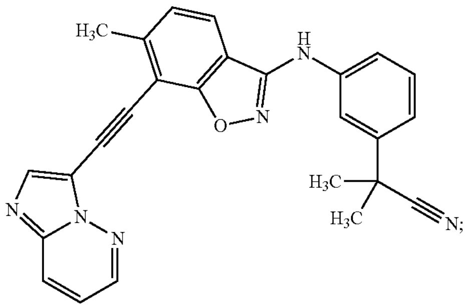

2-(3-((7-(imidazo[1,2-b]pyridazin-3-ylethynyl)-6-methylbenzo[d]isoxazol-3-yl)amino)phenyl)-2-methylpropanenitrile Compound 116

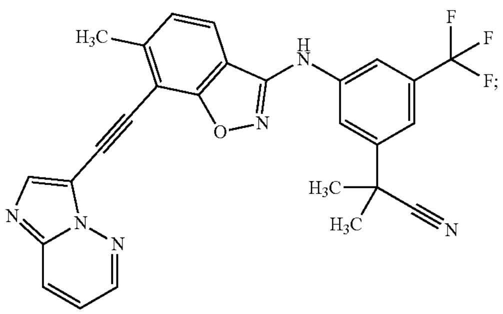

2-(3-((7-(imidazo[1,2-b]pyridazin-3-ylethynyl)-6-methylbenzo[d]isoxazol-3-yl)amino)-5-(trifluoromethyl)phenyl-2-methylpropanenitrile -continued Compound 117

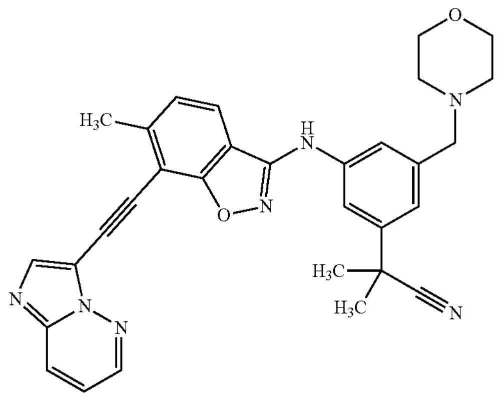

;

2-(3-((7-(imidazo[1,2-b]pyridazin-3-ylethynyl)-6-methylbenzo[d]isoxazol-3-yl)amino)-5-(morpholinomethyl)phenyl-2-methylpropanenitrile Compound 118

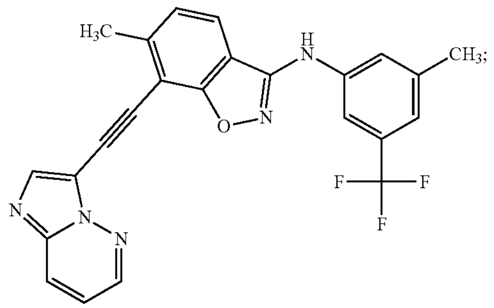

7-(imidazo[1,2-b]pyridazin-3-ylethynyl)-6-methyl-N-(3-methyl-5-(trifluoromethyl)phenyl)benzo[d]isoxazol-3-amine Compound 119

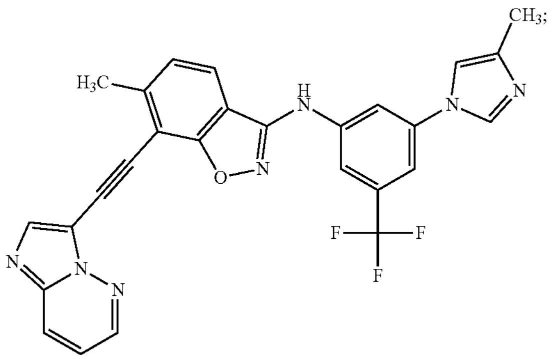

7-(imidazo[1,2-b]pyridazin-3-ylethynyl)-6-methyl-N-(3-(4-methyl-1H-imidazol-1-yl)-5-(trifluoromethyl)phenyl)benzo[d]isoxazol-3-amine -continued Compound 120

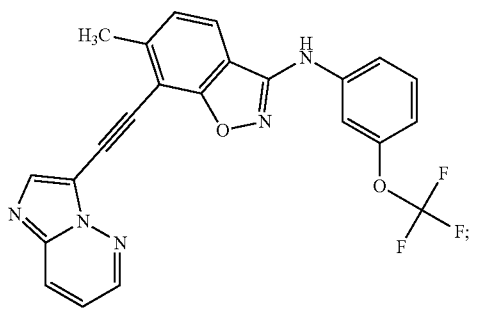

7-(imidazo[1,2-b]pyridazin-3-ylethynyl)-6-methyl-N-(3-(trifluoromethoxy)phenyl)benzo[d]isoxazol-3-amine Compound 121

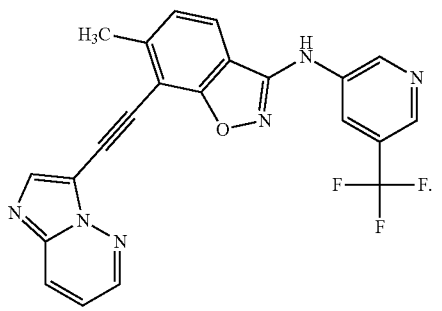

7-(imidazo[1,2-b]pyridazin-3-ylethynyl)-6-methyl-N-(5-(trifluoromethyl)pyridin-3-yl)benzo[d]isoxazol-3-amine Compounds 2-121 are examples of kinase (e.g., DDR1) inhibitors. Also, the Compounds 2-121 may represent other examples where the substituents are on other atoms from or on additional atoms than shown. The synthesis of the kinase (e.g., DDR1) inhibitor Compound 1 is shown in Scheme 1 herein. However, the illustrated synthesis can be modulated with different reagents or reagents having different functional groups in order to arrive at the Compounds 2-121 as well as others.

In some embodiments, the kinase (e.g., DDR1) inhibitor is one of Compounds 1 and 110-121.

In view of Formulae A-H and Formula 1-28, the features of the Compounds 1-121 can be rearranged and combined to form other examples of the kinase (e.g., DDR1) inhibitors. That is, the variables of one or more of Formulae A-H and Formula 1-28 can be selected from those in Compounds 1-121, and a molecule have different variables selected from the different Compounds 1-121. As such, the different rings, ring hetero atoms, linkers, and R group substituents may be rearranged and combined as described herein, such as selecting from the features of Compounds 1-121.

In some embodiments, a kit includes two or molecules of Compounds 1-121. In some aspects, the kit includes two or more of Compounds 1 and 110-121.

In some embodiments, the compounds can be devoid of a P, S, or Si atom.

The kinase (e.g., DDR1) inhibitors can be formulated for experiments or therapies. The formulations are prepared for storage and use by combining a purified kinase (e.g., DDR1) inhibitor of the present invention with a pharmaceutically acceptable vehicle (e.g., carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g., octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer, intratracheal, intranasal, epidermal and transdermal); oral; or parenteral including intravenous, intraarterial, subcutaneous, intraperitoneal or intramuscular injection or infusion; intratumoral, or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc. of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include kinase (e.g., DDR1) inhibitors of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The kinase (e.g., DDR1) inhibitor can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semi-permeable matrices of solid hydrophobic polymers containing the kinase (e.g., DDR1) inhibitor, which matrices are in the form of shaped articles (e.g. films or microcapsules). Examples of sustained-release matrices include polyesters, hydrogels such as poly(2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of a DDR1 inhibitor agent of the present invention and a chemotherapeutic agent or cocktail of multiple different chemotherapeutic agents. Combination therapy often uses agents that work by different mechanisms of action. Combination therapy using agents with different mechanisms of action often results in additive or synergetic effects. Combination therapy may allow for lower doses of each agent than is used in monotherapy thereby reducing toxic side effects. Combination therapy may decrease the likelihood that resistant cancer cells will develop. In some embodiments, the combination therapy comprises a kinase (e.g., DDR1) inhibitor that binds to kinase (e.g., DDR1) and a chemotherapeutic agent.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween®), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration. Common carriers or excipients can be used for preparing pharmaceutical compositions designed for such routes of administration.

For the treatment of the disease, the appropriate dosage of a kinase (e.g., DDR1) inhibitor of the present invention depends on the type of disease to be treated, the severity and course of the disease, the responsiveness of the disease, whether the kinase (e.g., DDR1) inhibitor is administered for therapeutic or preventative purposes, previous therapy, patient's clinical history, and so on, all at the discretion of the treating physician. The kinase (e.g., DDR1) inhibitor can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual kinase (e.g., DDR1) inhibitor. The administering physician can easily determine optimum dosages, dosing methodologies and repetition rates. In general, dosage is from 0.01 μg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the kinase (e.g., DDR1) inhibitor described herein and that can be used to perform the methods described herein. In certain embodiments, a kit comprises at least one purified kinase (e.g., DDR1) inhibitor in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed kinase (e.g., DDR1) inhibitors of the present invention can be readily incorporated into one of the established kit formats which are well known in the art.

In some embodiments, the compounds can have an inhibitory activity against a wild type or mutant (especially a clinically relevant mutant) kinase, especially a Src family kinase such as Src, Yes, Lyn or Lck; a VEGF-R such as VEGF-R1 (Flt-1), VEGF-R2 (kdr), or VEGF-R3; a PDGF-R; an Abl kinase; or DDR1 kinase; or another kinase of interest with an IC50 value of 1 μM or less (as determined using any scientifically acceptable kinase inhibition assay), preferably with an IC50 of 500 nM or better, and optimally with an IC50 value of 250 nM or better. In some aspects, the compounds can have an inhibitory activity against both Src and kdr with a 1 μM or better IC50 value against each. In some aspects, the compounds can have a cytotoxic or growth inhibitory effect on cancer cell lines maintained in vitro, or in animal studies using a scientifically acceptable cancer cell xenograft model, or against live tumors in an individual.

Also provided is a composition comprising at least one compound of the invention or a salt, hydrate or other solvate thereof, and at least one pharmaceutically acceptable excipient or additive. Such compositions can be administered to a subject in need thereof to inhibit the growth, development and/or metastasis of cancers, including solid tumors (e.g., breast, colon, pancreatic, CNS and head and neck cancers, among others) and various forms of leukemia, including leukemias and other cancers which are resistant to other treatment, including those which are resistant to treatment with Gleevec or another kinase inhibitor, and generally for the treatment and prophylaxis of diseases or undesirable conditions mediated by one or more kinases which are inhibited by a compound of this invention.

The cancer treatment method of this invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

One embodiment is a method for treating cancer in a subject in need thereof, which comprises administering to the subject a treatment effective amount of a composition containing a compound of this invention. Various cancers which may be thus treated are noted elsewhere herein and include, among others, cancers which are or have become resistant to another anticancer agent such as Gleevec, Iressa, Tarceva or one of the other agents noted herein. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of this invention.

In some embodiments, the invention includes the synthesis of one of the compounds of the invention.

The invention also comprises the use of a compound of the invention, or a pharmaceutically acceptable derivative thereof, in the manufacture of a medicament for the treatment either acutely or chronically of cancer (including leukemias and solid tumors, primary or metastatic, including cancers such as noted elsewhere herein and including cancers which are resistant or refractory to one or more other therapies). The compounds of this invention are useful in the manufacture of an anti-cancer medicament. The compounds of the present invention are also useful in the manufacture of a medicament to attenuate or prevent disorders through inhibition of one or more kinases such as Src, kdr, abl. etc.

Other disorders which may be treated with a compound of this invention include metabolic disorders, inflammatory disorders and osteoporosis and other bone disorders. In such cases the compound of this invention may be used as a monotherapy or may be administered in conjunction with administration of another drug for the disorder, e.g., a bisphosphonate in the case of osteoporosis or other bone-related illnesses.

Compounds of this invention are also useful as standards and reagents for characterizing various kinases, especially but not limited to kdr and Src family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

In some embodiments, a pharmaceutical composition can include the compound of one of the embodiments provided herein and a pharmaceutically acceptable carrier having the compound. In some aspects, the composition can include an additional therapeutic agent. In some aspects, the additional therapeutic agent is a chemotherapeutic agent. In some aspects, the additional therapeutic agent is gemcitabine. In some aspects, the additional therapeutic agent is dasatinib. In some aspects, the additional therapeutic agent is irinotecan. In some embodiments, the composition includes a plurality of the compounds of Formula A.

In some embodiments, the pharmaceutically acceptable carrier includes at least one of a buffer, organic acid, salt, antioxidant, preservative, polymer, carbohydrate, chelating agent, sugar, or surfactant. In some aspects, the pharmaceutically acceptable carrier is configured for an administration route selected from topical, transdermal, pulmonary, oral, intravenous, intraarterial, subcutaneous, intraperitoneal, intramuscular, intratumora, intranasal, intraorbital, ophthalmic, intraventricular, intracapsular, intraspinal, intracisternal, or intracranial. In some aspects, the pharmaceutically acceptable carrier is configured as a dosage form selected from, tablet, pill, capsule, powder, granule, solution, suspension, or suppository. In some aspects, the compound of Formula A is contained in a liposome, microsphere, microemulsion, nano-particle, nano-capsule, sustained release matrix, or combination thereof.

In some embodiments, a method of inhibiting a kinase can include providing the compound of one of the embodiments to the kinase such that the kinase is inhibited. In some aspects, the kinase is a receptor tyrosine kinase. In some aspects, the receptor tyrosine kinase is a discoidin domain receptor family member. In some aspects, the discoidin domain receptor family member is DDR1. In some aspects, the discoidin domain receptor family member is DDR2. In some aspects, the inhibition of the kinase inhibits transfer of a phosphate group from ATP to another molecule. In some aspects, the inhibition of the kinase inhibits a phosphorylation pathway. In some aspects, the inhibition of the receptor tyrosine kinase inhibits binding of the receptor tyrosine kinase with at least one of a growth factor, cytokine, or hormone. In some aspects, the inhibition of the discoidin domain receptor family member inhibits communication between cells. In some aspects, the inhibition of DDR1 inhibits binding of a substance to the DDR1. In some aspects, the inhibition of binding inhibits binding of the DDR1 with fibrillar collagen. In some aspects, the inhibition of binding of DDR1 with fibrillar collagen inhibits cellular attachment to an extracellular matrix or remodeling of the extracellular matrix.

In some embodiments, the inhibition of DDR1 results in at least one of: inhibiting cell growth; inhibiting cell migration; inhibiting cell proliferation; or inhibiting cell migration. In some aspects, the inhibited DDR1 is present on an epithelial cell. In some aspects, the epithelial cell is selected from cells of a kidney, lung, gastrointestinal tract, or brain. In some aspects, the inhibited DDR1 inhibits an SRC signaling pathway. In some aspects, the inhibited DDR1 inhibits activation of a MAP kinase. In some aspects, the receptor tyrosine kinase (RTK) is at least one of the classes recited herein.

In some embodiments, a method of inhibiting cellular communication can include providing the compound of one of the embodiments to a cell so as to inhibit communication of the cell with a surrounding environment of the cell. In some aspects, the cell is inhibited from interacting with a cell growth regulating substance. In some aspects, the cell is inhibited from interacting with a differentiation regulating substance. In some aspects, the cell is inhibited from interacting with a metabolism regulating substance. In some aspects, the compound binds with a discoidin domain receptor family member.

In some embodiments, a method of inhibiting a cell attachment to an extracellular matrix can include providing the compound of one of the embodiments to a DDR1 receptor of the cell to inhibit the DDR1 receptor from interacting with fibrillar collagen. In some aspects, the inhibition of DDR1 inhibits remodeling of an extracellular matrix around the cell. In some embodiments, a method of inhibiting cell activity can include providing the compound of one of the embodiments to a cell so as to inhibit at least one biological function of the cell. In some aspects, the biological function of the cell is at least one of: cell growth; differentiation; cell migration; cell proliferation; or cell metabolism. In some aspects, the compound inhibits a discoidin domain receptor family member of the cell. In some aspects, the discoidin domain receptor family member is DDR1 or DDR2. In some aspects, the discoidin domain receptor family member is DDR1. In some aspects, the cell is an epithelial cell. In some aspects, the epithelial cell is selected from a cell from a kidney, lung, gastrointestinal tract, or brain.

In some embodiments, a method of promoting remodeling of an extracellular matrix can include providing the compound of one of the embodiments to a DDR1 receptor so as to cause upregulation of a matrix metalloproteinase. In some aspects, the matrix metalloproteinase is selected from MMP2, MMP7 or MMP9. In some aspects, the upregulation of a matrix metalloproteinase causes cellular migration. In some aspects, the upregulation of a matrix metalloproteinase causes wound healing.

In some embodiments, a method of inhibiting blastocyte implantation, such as during pregnancy, can include providing the compound of one of the embodiments to a DDR1 receptor of an undifferentiated cell in a blastula stage of an embryo. In some embodiments, the embryo is in a pregnant female. In some aspects, the method includes administering a sufficient amount of the compound to the pregnant female so as to cause abortion of the embryo.

In some embodiments, a method of inhibiting mammary gland differentiation can include providing the compound of one of the embodiments to a DDR1 receptor of a mammary gland so as to inhibit differentiation of cells of the mammary gland. In some aspects, the mammary gland is in a pregnant female. In some aspects, the method can include administering a sufficient amount of the compound to the pregnant female to inhibit development of the mammary gland. In some aspects, the compound inhibits lactation from the mammary gland. In some aspects, the mammary gland is in a non-pregnant female. In some aspects, the method can include administering a sufficient amount of the compound to the non-pregnant female to inhibit development of breast cancer.

In some embodiments, a method of inhibiting activity of a cancer cell can include administering the compound of one of the embodiments to the cancer cell so as to inhibit a biological activity of the cancer cell. In some aspects, the administering includes a therapeutically effective amount of the compound sufficient to: inhibit cancer cell growth; inhibit cancer cell migration; inhibit cancer cell proliferation; inhibit cancer cell migration; or inhibit cancer cell metabolism. In some aspects, the cancer cell is in a subject that has been diagnosed with cancer prior to the administration of the compound. In some aspects, the cancer cell is in a subject that has not been diagnosed with cancer prior to the administration of the compound. In some aspects, the cancer cell is in a breast tumor, colorectal tumor, hepatic tumor, renal tumor, lung tumor, pancreatic tumor, gastrointestinal tumor, ovarian tumor, prostate tumor, skin tumor, bladder tumor, cervical tumor, or head and neck tumor. In some aspects, the method can include administering at least one additional chemotherapeutic agent to the cancer cell with the compound of Formula A.

In some embodiments, a method of treating cancer in a subject can include administering the compound of one of the embodiments to a subject that has cancer. In some aspects, the method can include administering a sufficient amount of the compound to inhibit a kinase of a cancer cell. In some aspects, the kinase is a receptor tyrosine kinase. In some aspects, the receptor tyrosine kinase is a discoidin domain receptor family member. In some aspects, the discoidin domain receptor family member is DDR1. In some aspects, the discoidin domain receptor family member is DDR2. In some aspects, the method can include administering a sufficient amount of the compound to inhibit a phosphorylation pathway of the cancer cell. In some aspects, the method can include administering a sufficient amount of the compound to inhibit binding of the receptor tyrosine kinase with at least one of a growth factor, cytokine, or hormone. In some aspects, the method can include administering a sufficient amount of the compound to inhibits chemical communication between cancer cells. In some aspects, the inhibition of DDR1 inhibits binding of a substance to the cancer cell. In some aspects, the inhibition of binding inhibits binding of the cancer cell with fibrillar collagen. In some aspects, the inhibition of binding of DDR1 with fibrillar collagen inhibits cellular attachment to an extracellular matrix or remodeling of the extracellular matrix. In some aspects, the inhibition of DDR1 results in at least one of: inhibiting cancer cell growth; inhibiting cancer cell migration; inhibiting cancer cell proliferation; inhibiting cancer cell metabolism; inhibiting cancer cell metastasis; or inhibiting cancer cell migration. In some aspects, the cancer cell is inhibited from interacting with a cell growth regulating substance. In some aspects, the cancer cell is inhibited from interacting with a differentiation regulating substance. In some aspects, the cancer cell is inhibited from interacting with a metabolism regulating substance. In some aspects, the cancer is in a subject that has been diagnosed with cancer prior to the administration of the compound. In some aspects, the cancer is in a subject that has not been diagnosed with cancer prior to the administration of the compound. In some aspects, the subject desires to avoid contracting cancer and takes the compound as a prophylactic. In some aspects, the cancer is a breast cancer, colorectal cancer, hepatic cancer, renal cancer, lung cancer, pancreatic cancer, gastrointestinal cancer, ovarian cancer, prostate cancer, skin cancer, bladder cancer, cervical cancer, or head and neck cancer. In some aspects, the method can include administering at least one additional chemotherapeutic agent to the subject with the compound of Formula A, which can provide a combination therapy. In some aspects, the method can include administering a sufficient amount of the compound to reduce a number of cancer cells in the cancer. In some aspects, the method can include administering a sufficient amount of the compound to reduce a number of cancer stem cells in the cancer.

In some embodiments, a method of synthesizing the compound of one of the embodiments described herein can be performed. Such a method can include performing at least one synthesis step with at least two reactants that react to form the compound having a structure of Formula A, derivative thereof, prodrug thereof, salt thereof, stereoisomer thereof, tautomer thereof, polymorph thereof, or solvate thereof, or having any chirality at any chiral center, wherein the Formula A is the same as provided herein with the same variables.

Formula A

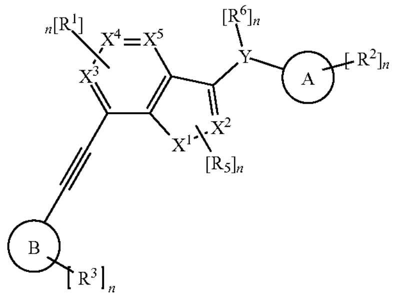

In Formula A, ring A is a ring structure; ring B is a ring structure; the $X^1$, $X^2$, $X^3$, $X^4$, and $X^5$ are each independently a carbon or a hetero atom with or without a substituent; the Y is a linker; and each $R^1$, $R^2$, $R^3$, $R^5$, and $R^6$ is independently a substituent, wherein $R^5$ and/or $R^6$ is optionally nothing, and each n is independently an integer that defines the number of R group substituents for each R as shown. The n can from 0 to the number of possible R group substituents for the linker or ring structure as shown.

The synthesis method can include obtaining a reactant A that includes the ring A, and obtaining a reactant B that includes the ring B. The synthesis method can also include obtaining a first reactant having a ring structure, and reacting a second reactant with the first reactant to form a polycyclic structure, the polycyclic structure having variables $X^1$, $X^2$, $X^3$, $X^4$, and $X^5$. In some aspects, the method can include: providing a reactant A that includes the ring A having at least one $R^2$ substituent and an amine; providing a first reactant with a ring structure with at last one $R^1$ substituent, at least one halogen substituent, and at least one carboxylic acid; and reacting the reactant A with the first reactant to form a first product having ring 1 and an amide linkage, wherein ring 1 is a ring structure. In some aspects, the reactant A and the first reactant have structures as follows:

reactant A

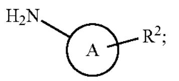

and

-continued

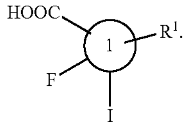

first reactant

In some aspects, the first product has a structure as follows:

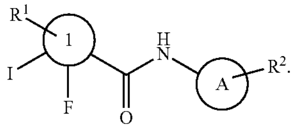

first product

In some aspects, the synthesis includes reacting the first product with Lawesson's reagent to convert the double bonded oxygen of the amide linkage to a double bonded sulfur to obtain product 2 having the double bonded sulfur. In some aspects, the synthesis includes reacting the first product with Lawesson's reagent to convert the double bonded oxygen of the amide linkage to a double bonded sulfur to obtain product 2 that has a structure as follows:

product 2

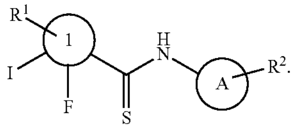

In some aspects, the method includes reacting the product 2 with a hydroxyl amine to replace the double bonded sulfur with a double bonded nitrogen to obtain product 3 having the double bonded nitrogen with a hydroxyl group linked to the double bonded nitrogen. In some aspects, the synthesis includes reacting the product 2 with a hydroxyl amine to replace the double bonded sulfur with a double bonded nitrogen that is linked to a hydroxyl group to obtain product 3 that has a structure as follows:

product 3

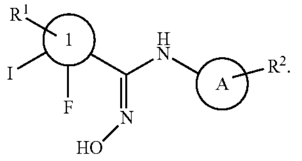

As shown in the synthesis steps, reactants, and products, the illustration of an R group, such as $R^1$, $R^2$, $R^3$, or other represents the presence of an optional substituent, where each ring or linker may include one or more of the R groups. As such, each R group represents from 0 to the maximum allowed number of substituents. For simplicity, each ring or linker is only shown with one R group, but it is understood that each shown R group can be from 0 or 1 to the maximum number of R groups allowed for the structure. Accordingly, each R group could be considered [R]n, wherein n is an integer as defined herein for the different formulae.

In some aspects, the synthesis includes reacting the product 3 with a reagent that causes the hydroxyl group to react with one halogen of the at least one halogens to form product 4 that includes a first hetero ring such that ring 1 and the first hetero ring form a polycycle.

In some aspects, the synthesis includes reacting the product 3 with a reagent that causes the hydroxyl group to react with one halogen of the at least one halogens to form a first hetero ring such that ring 1 and the first hetero ring form a polycycle in product 4 that has a structure as follows:

product 4

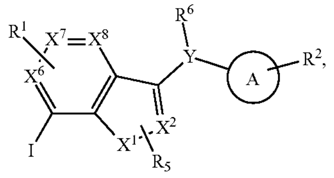

wherein Y is N, $R^6$ is hydrogen, $R^5$ is nothing, $X^1$ is O, and $X^2$ is N.

In some aspects, the synthesis includes reacting product 4 with reactant B that includes the ring B to form the compound of Formula A. In some aspects, the synthesis includes reacting product 4 with reactant B that includes the ring B to form the compound of Formula A, wherein reactant B has a structure as follows:

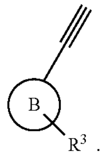

In some aspects, the synthesis includes reacting product 4 with reactant C that includes a polycycle having ring B fused with ring C to form a compound having a structure of Formula H, derivative thereof, prodrug thereof, salt thereof, stereoisomer thereof, tautomer thereof, polymorph thereof, or solvate thereof, or having any chirality at any chiral center, Formula H

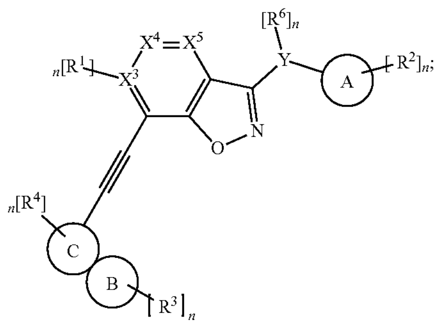

wherein: ring A is a ring structure; ring B is a ring structure; ring C is a ring structure fused with ring C; the $X^3$, $X^4$, and $X^5$ are each independently a carbon or a hetero atom; the Y is a linker; and each $R^1$, $R^2$, $R^3$, $R^4$, and $R^6$ is independently at least one substituent (e.g., each substituent on a ring or atom is at least one independent substituent and can be from zero to the maximum allowed substituents), wherein $R^6$ is optionally nothing. In some aspects, the method includes reacting product 4 with reactant C that includes ring B fused with ring C to form the compound of Formula H, wherein reactant C has a structure as follows:

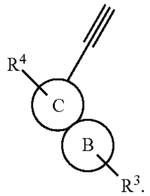

Figure 3A:
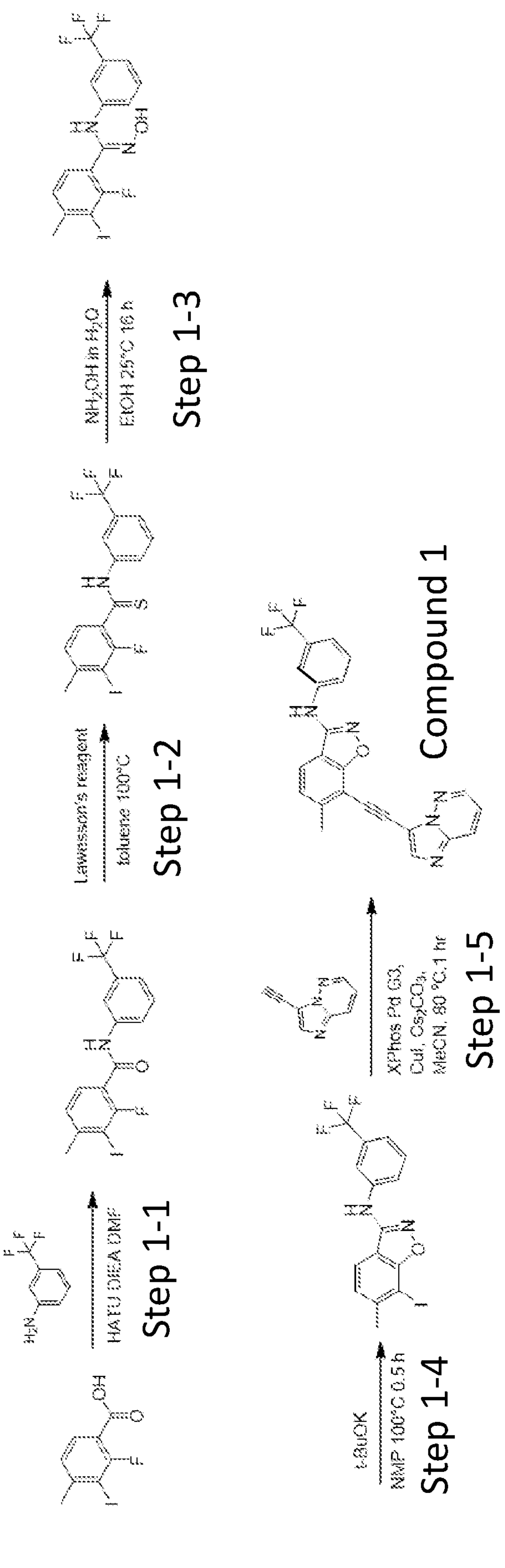
FIG. 3A shows Scheme 1 for the synthetic route to Compound 1.

In some embodiments, the synthesis can include performing a reaction protocol of Scheme 1 to form Compound 1, as shown in FIG. 3A.

Figure 3B:
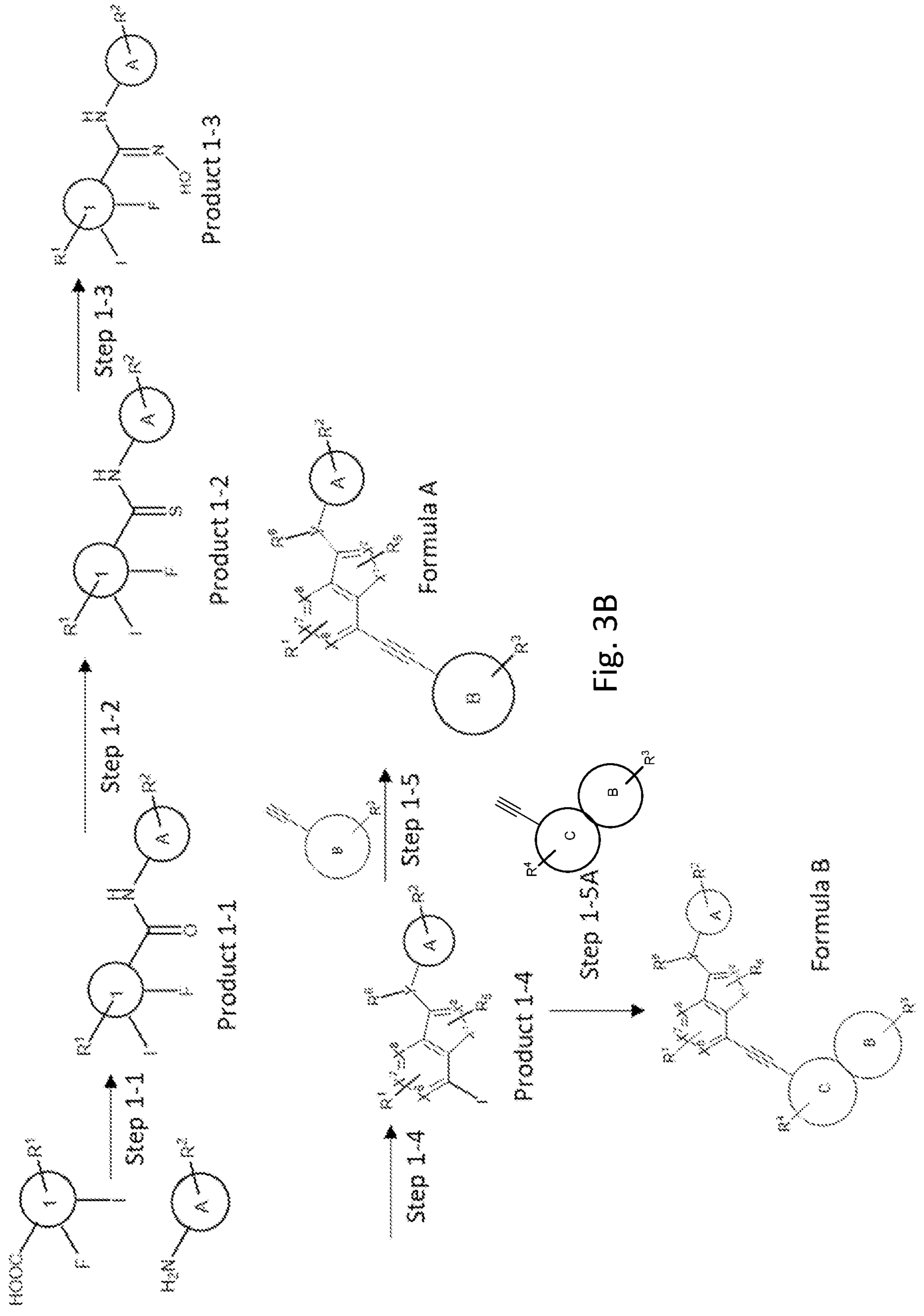
FIG. 3B shows a general reaction scheme based on Scheme 1 for the synthetic route to compounds under Formula A and/or Formula B.
Figure 3C:
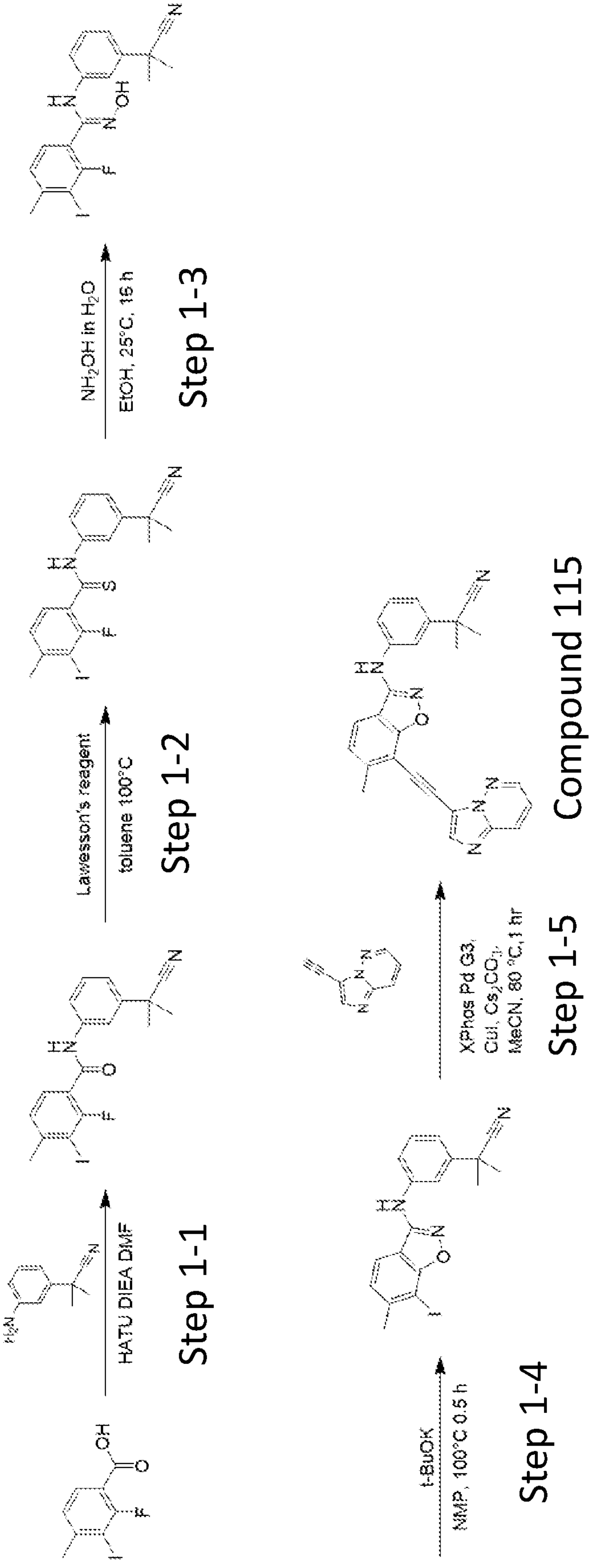
FIG. 3C shows a modification of Scheme 1 (e.g., Scheme 1A), which uses a different Ring A reactant that results in the Ring A of the product being in the structure of Compound 115.

In some embodiments, the synthesis can include performing a reaction protocol of Scheme 1A to form Compound 115, as shown in FIG. 3C.

Figure 3D:
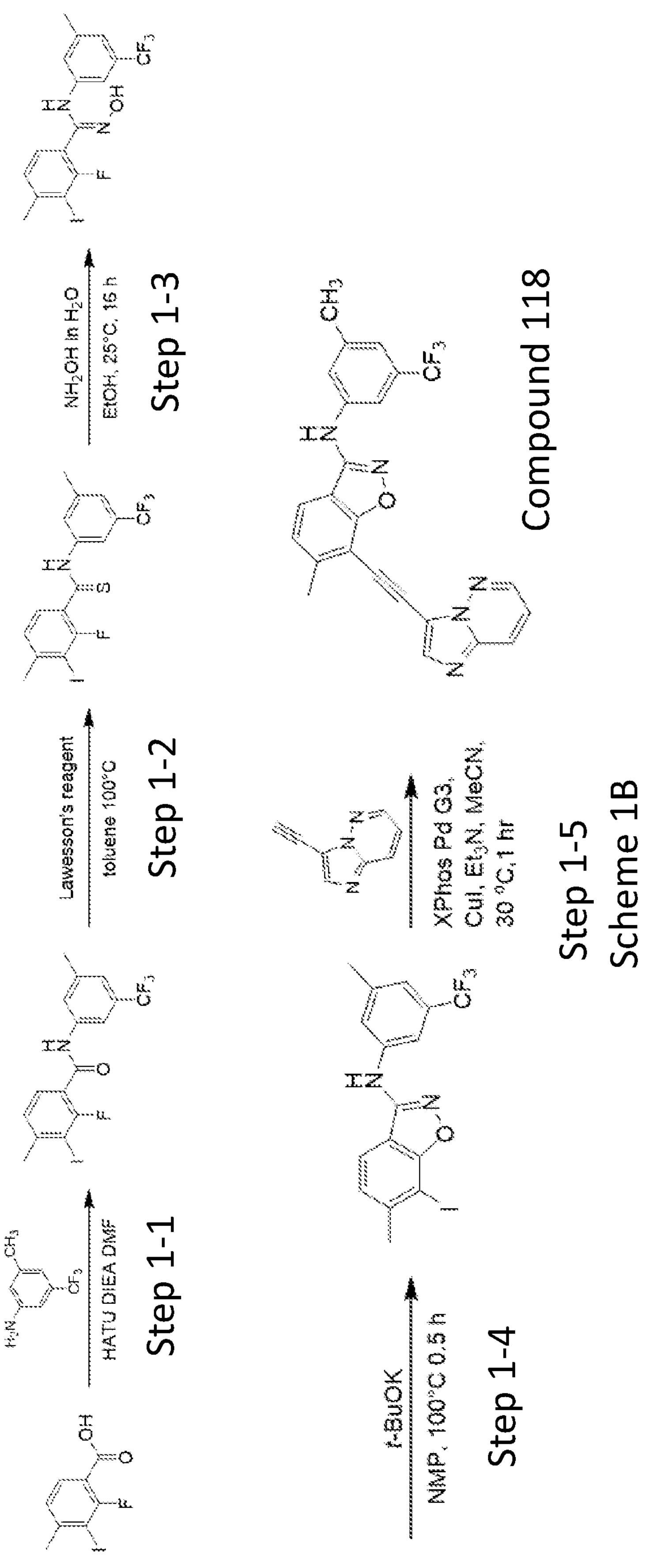
FIG. 3D shows a modification of Scheme 1 (e.g., Scheme 1B), which uses a different Ring A reactant that results in the Ring A of the product being in the structure of Compound 118.

In some embodiments, the synthesis can include performing a reaction protocol of Scheme 1B to form Compound 118, as shown in FIG. 3D.

Figure 3E:
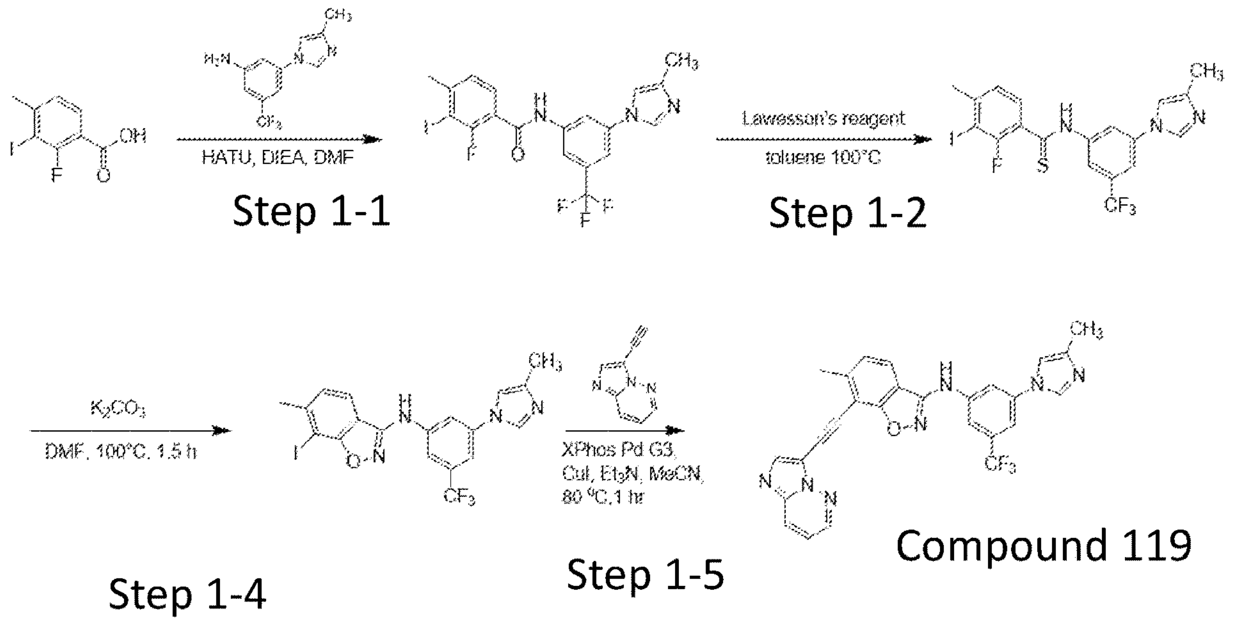
FIG. 3E shows a modification of Scheme 1 (e.g., Scheme 1C), which uses another Ring A reactant that results in the Ring A of the product being in the structure of Compound 119.

In some embodiments, the synthesis can include performing a reaction protocol of Scheme 1C to form Compound 119, as shown in FIG. 3E.

In some embodiments, the synthesis can include: obtaining a first reactant having a ring structure substituted with $R^1$, a fluorine group, and a cyano group; and reacting the first reactant with iodine to obtain a first product having the ring structure substituted with $R^1$, the fluorine group, an iodine group, and a cyano group. In some aspects, the first reactant and the first product each have a following structure:

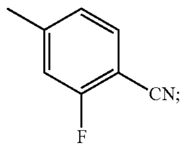

first reactant and

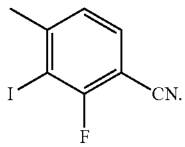

first product

In some embodiments, the synthesis can include reacting the first product with N-hydroxyacetamide to form product 2 with a polycycle having at least one hetero ring fused with the ring of the first product, the at least one hetero ring including an amine substituent and the polycycle having an iodine substituent.

In some aspects, product 2 has the following structure:

product 2

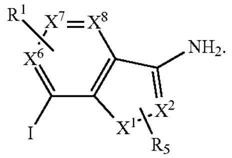

In some aspects, the product 2 has the following structure:

product 2

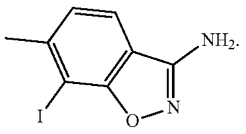

In some embodiments, the synthesis can include reacting product 2 with a reactant A having ring A with at least one $R^2$ substituent and a leaving group to form product 3 having the ring A linked through a linker to the hetero ring of the polycycle of product 2, and the polycycle having the iodine substituent. In some aspects, reactant A and product 3 each has a following structure:

reactant A

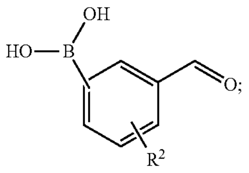

and product 3

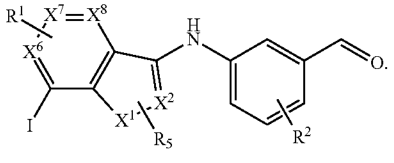

In some aspects, the synthesis can include: reacting product 3 with a reagent that has a second $R^2$ substituent to form product 4. In some aspects, the second $R^2$ substituent is different from the $R^2$ substituent on the ring A. In some aspects, product 4 has a structure of:

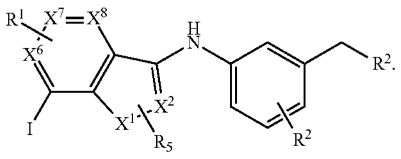

In some aspects, the synthesis can include reacting product 4 with reactant B that includes the ring B to form a compound of Formula 29A, derivative thereof, prodrug thereof, salt thereof, stereoisomer thereof, tautomer thereof, polymorph thereof, or solvate thereof, or having any chirality at any chiral center:

Formula 29A

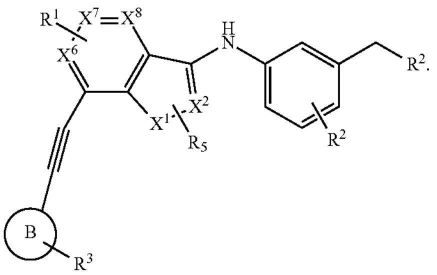

In some aspects, the synthesis can include reacting product 4 with reactant C that includes a polycycle having ring B fused with ring C to form a compound having a structure of Formula 29B, derivative thereof, prodrug thereof, salt thereof, stereoisomer thereof, tautomer thereof, polymorph thereof, or solvate thereof, or having any chirality at any chiral center:

Formula 29B

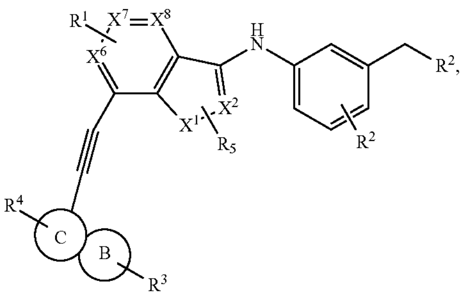

wherein: ring B is a ring structure; ring C is a ring structure fused with ring C; and each $R^2$ is independently a substituent.

In some aspects, reactant A and product 3 each has a following structure:

reactant A

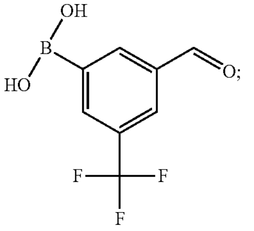

and product 3

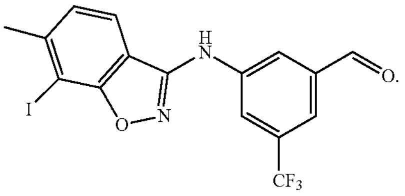

In some aspects, the synthesis includes reacting product 3 with 1-methylpiperazine to obtain product 4, which as a structure as follows:

Product 4

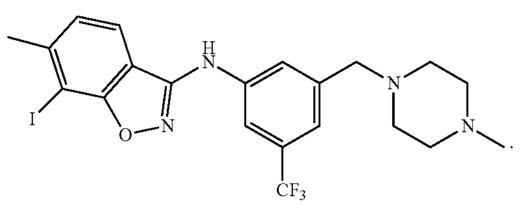

In some aspects, the synthesis can include reacting product 4 with reactant B that includes the ring B to form product 5 having the ring B linked through the carbon on product 4 having the iodine.

In some aspects, the synthesis includes reacting product 4 with reactant B that includes the ring B to form Compound 110:

Compound 110

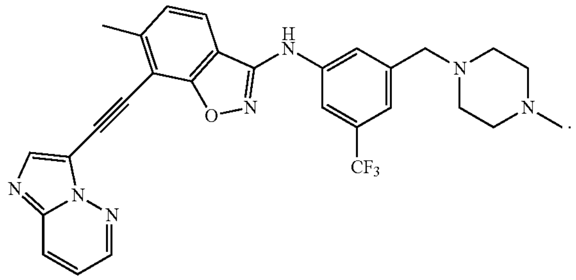

Figure 4A:
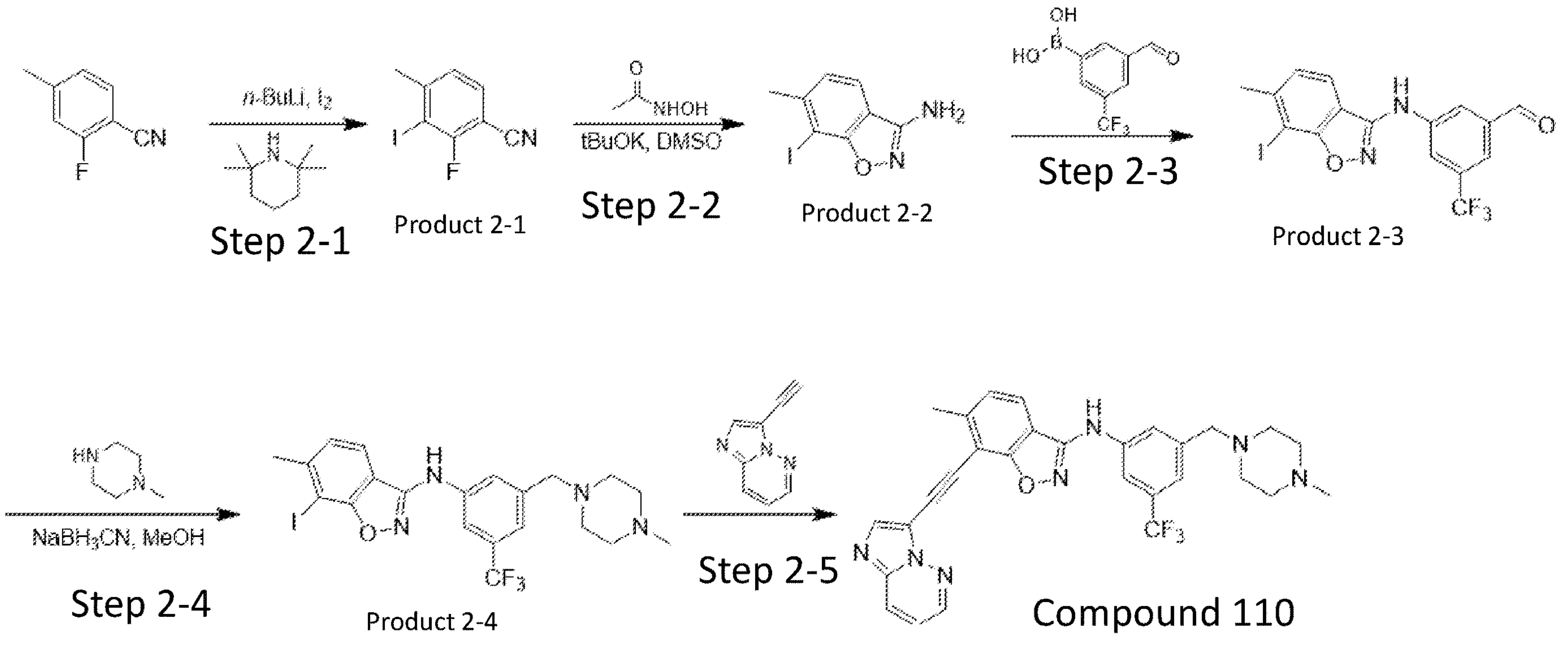
FIG. 4A shows reaction Scheme 2 for use in preparing Compound 110.

In some aspects, the synthesis can include performing a reaction protocol of Scheme 2 to form Compound 110, as shown in FIG. 4A.

Figure 4B:
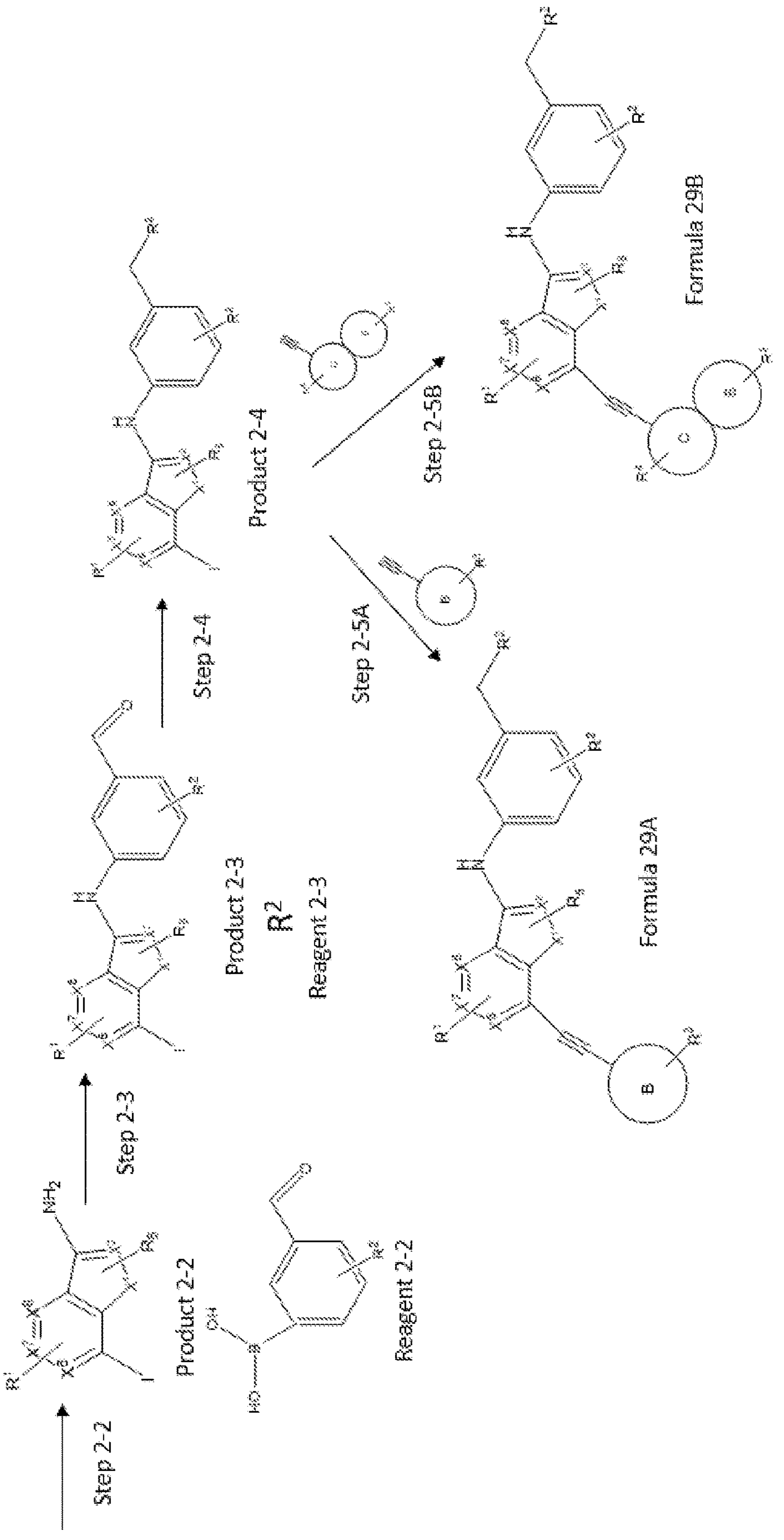
FIG. 4B shows the general reaction scheme based on Scheme 2 for preparing the compounds of Formula 29, which falls under the other general formulae provided herein, such as under Formula A, Formula B, or others.
Figure 4C:
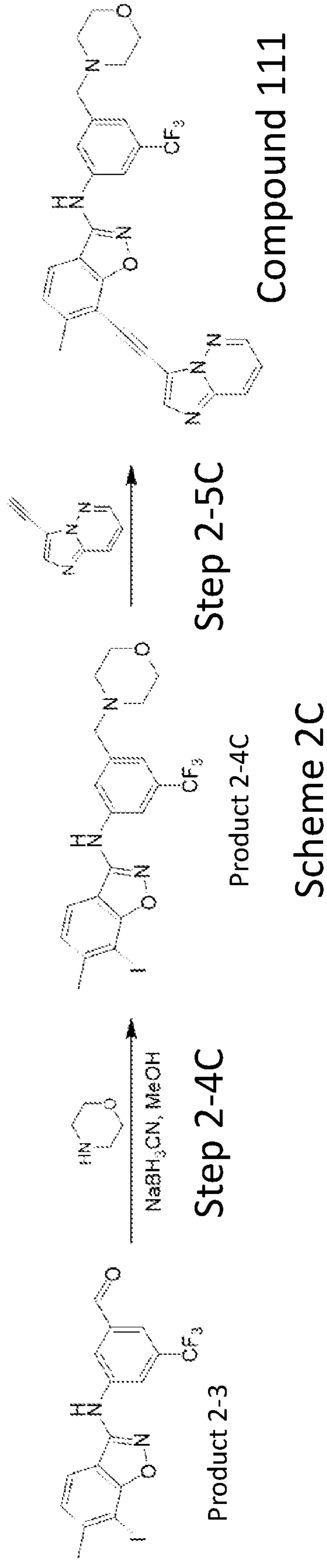
FIG. 4C shows Scheme 2C for the synthetic route to Compound 111.

In some aspects, the synthesis can include performing a reaction protocol of Scheme 2C to form Compound 111, as shown in FIG. 4C.

Figure 4D:
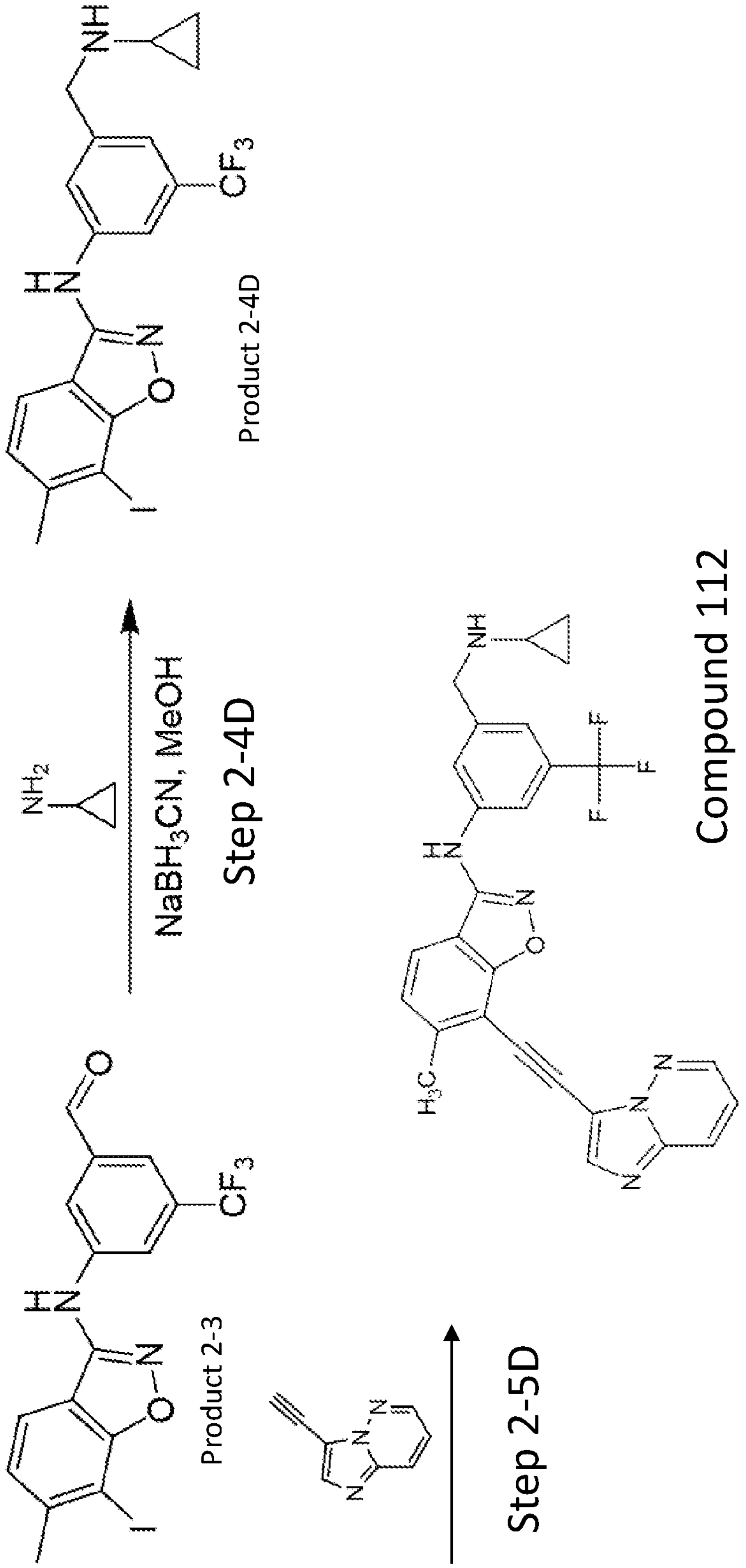
FIG. 4D shows Scheme 2D for the synthetic route to Compound 112.

In some aspects, the synthesis can include performing a reaction protocol of Scheme 2D to form Compound 112, as shown in FIG. 4D.

Figure 4E:
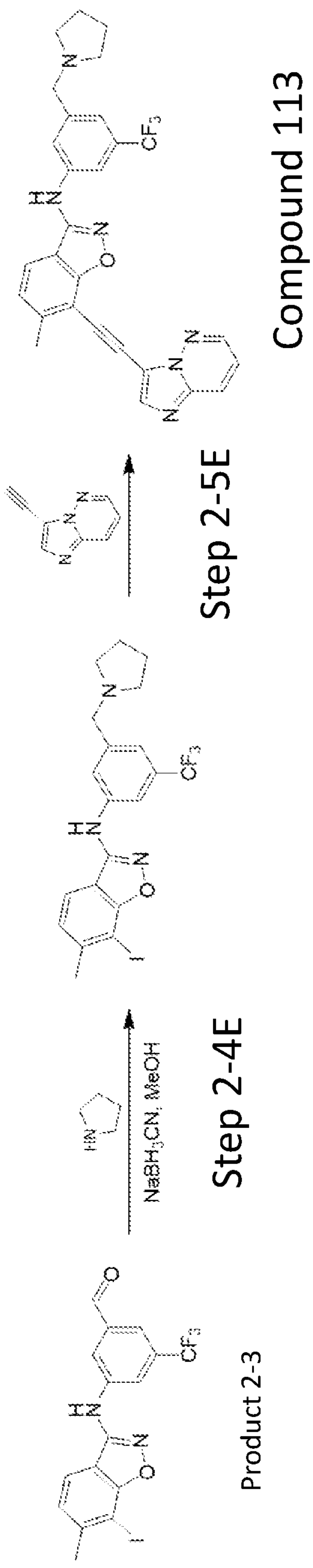
FIG. 4E shows Scheme 2E for the synthetic route to Compound 113.

In some aspects, the synthesis can include performing a reaction protocol of Scheme 2E to form Compound 113, as shown in FIG. 4E.

In some embodiments, the synthesis can include: obtaining a reactant A with ring A having at least two leaving groups and at least one $R^2$ substituent; and reacting reactant A with a first reactant that includes a second $R^2$ substituent to as to form product 1 with ring A having at least one leaving group, the at last one $R^2$ substituent and the second $R^2$ substituent.

In some aspects, reactant A and product 1 each has a following structure:

reactant A

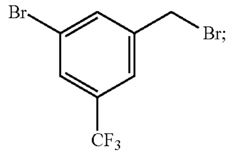

and

-continued product 1

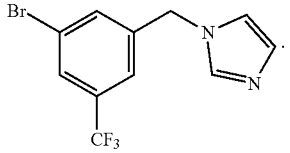

In some aspects, the synthesis can include reacting product 1 with a compound having a structure of Core A to obtain Compound 114, wherein the Core A and Compound 114 each have the following structure:

Core A

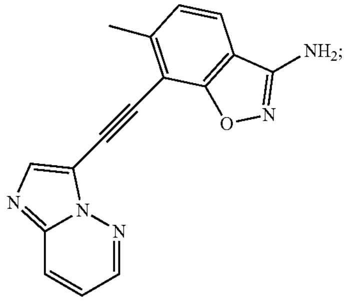

and

Compound 114

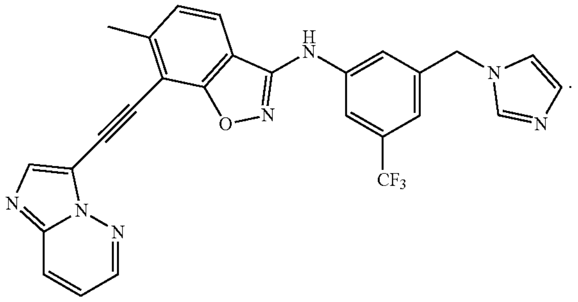

Figure 5A:
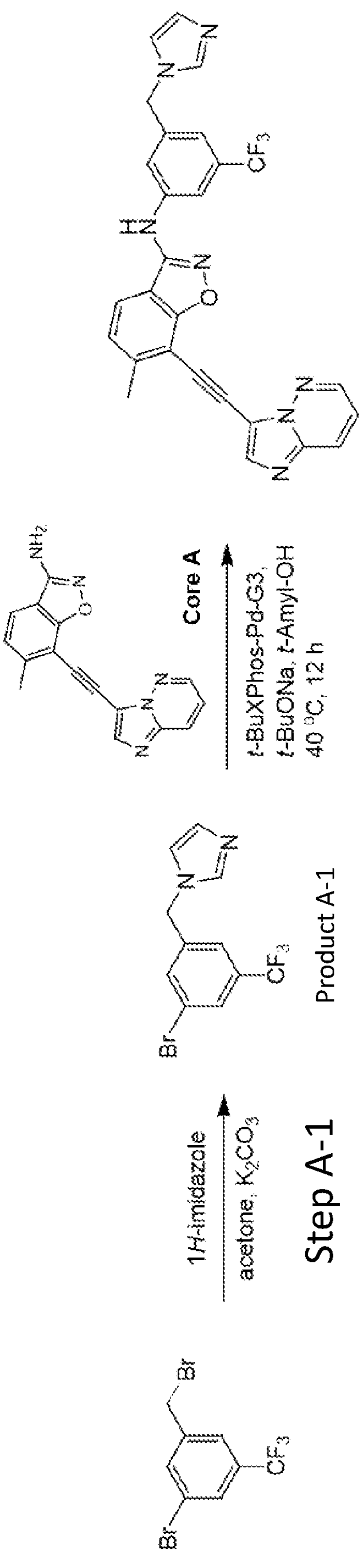
FIG. 5A shows Scheme A for the synthetic route to Compound 114.

In some aspects, the synthesis can include performing a reaction protocol of Scheme A to form Compound 114, as shown in FIG. 5A.

Figure 5B:
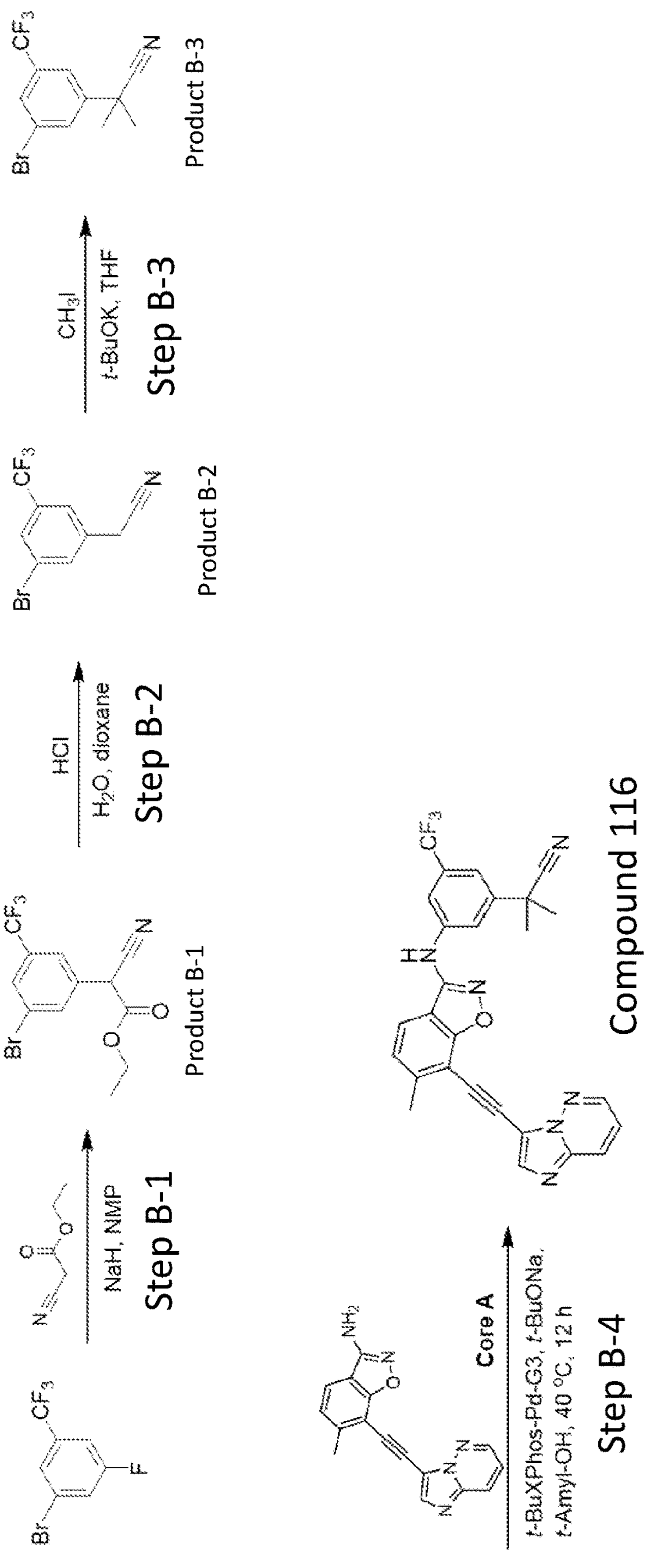
FIG. 5B shows Scheme B for the synthetic route to Compound 116.

In some aspects, the synthesis can include further comprising performing a reaction protocol of Scheme B to form Compound 116, as shown in FIG. 5B.

Figure 5C:
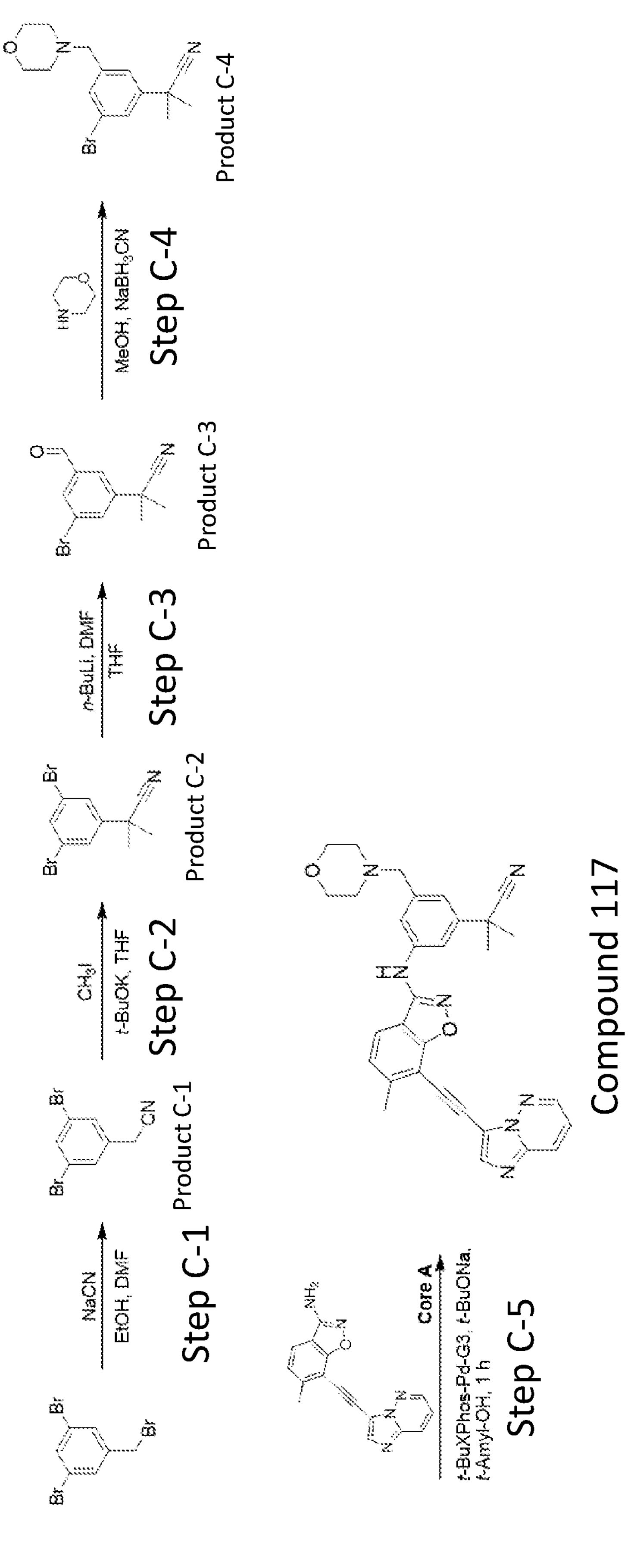
FIG. 5C shows Scheme C for the synthetic route to Compound 117.

In some aspects, the synthesis can include performing a reaction protocol of Scheme C to form Compound 117, as shown in FIG. 5C.

In some aspects, the synthesis can include: reacting the product 2 with a reactant A having a ring A with at least one $R^2$ substituent and a leaving group substituent to obtain product 3, wherein product 3 includes a nitrogen linker coupling product A to the ring A in place of the leaving group.

In some aspects, the synthesis can include reacting product 3 with a reactant B having ring B to obtain the compound of Formula A. In some aspects, the synthesis can include reacting product 3 with reactant B that includes the ring B to form the compound of Formula A, wherein reactant B has a structure as follows:

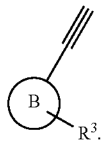

In some aspects, the synthesis can include reacting product 3 with reactant C that includes a polycycle having ring B fused with ring C to form a compound having a structure of Formula H, derivative thereof, prodrug thereof, salt thereof, stereoisomer thereof, tautomer thereof, polymorph thereof, or solvate thereof, or having any chirality at any chiral center, wherein Formula H is as defined herein with the defined variables thereof. In some aspects, the synthesis includes reacting product 3 with reactant C that includes ring B fused with ring C to form the compound of Formula H, wherein reactant C has a structure as defined herein.

Figure 6A:
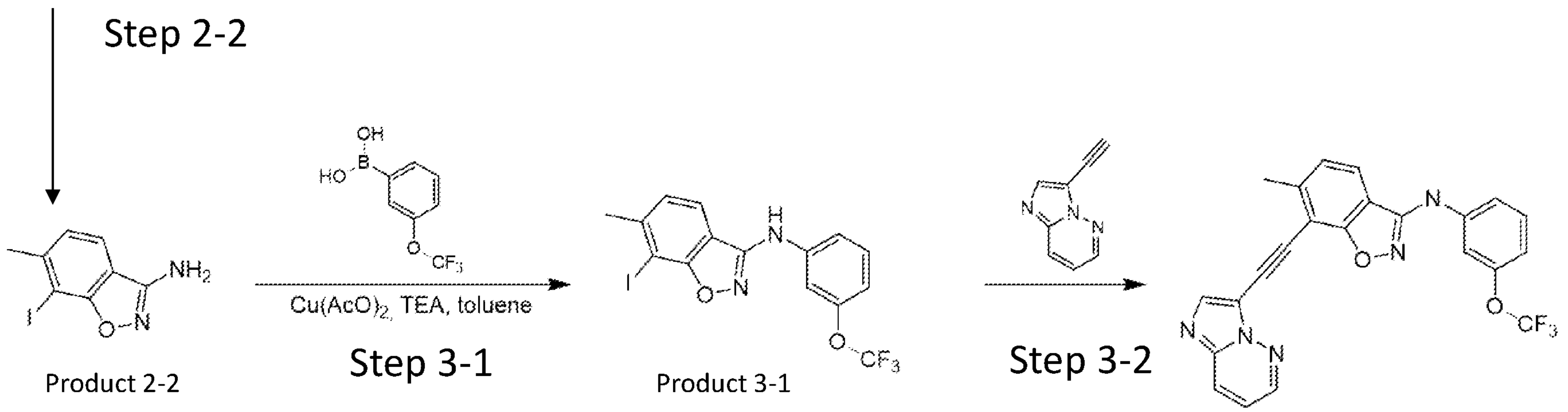
FIG. 6A shows Scheme 3 for the synthetic route to Compound 120.

In some aspects, the synthesis can include performing a reaction protocol of Scheme 3 to form Compound 120, as shown in FIG. 6A.

Figure 6B:
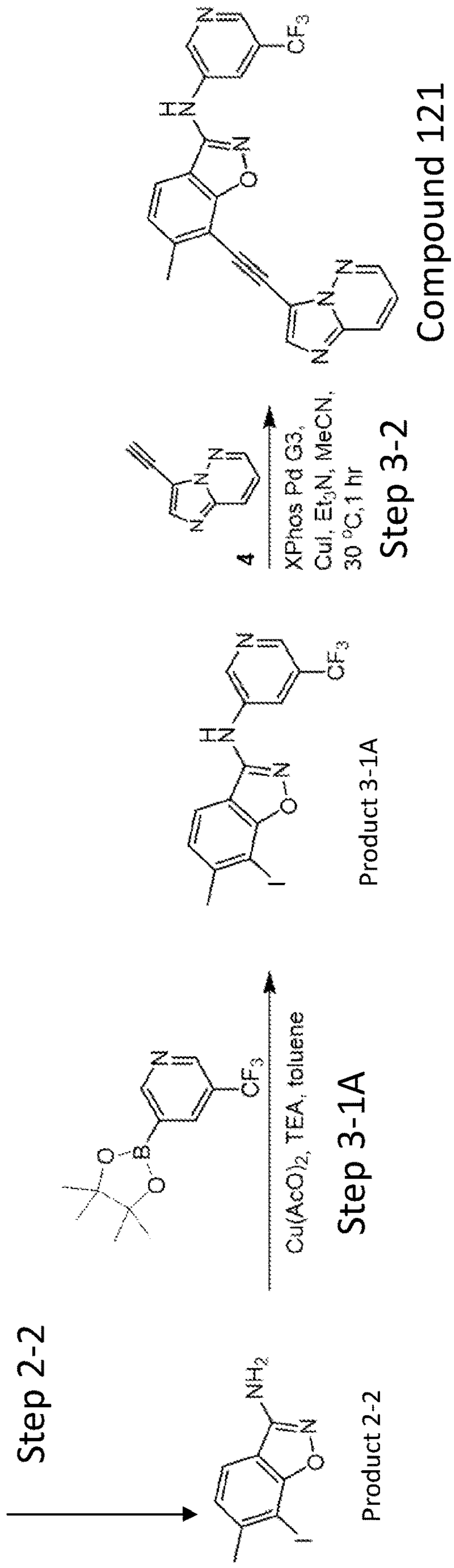
FIG. 6B shows Scheme 3A for the synthetic route to Compound 121.

In some aspects, the synthesis can include performing a reaction protocol of Scheme 3A to form Compound 121, as shown in FIG. 6B.

In view of the synthetic protocols described herein, it should be recognized that the reagents that are used can be modified in accordance with the structures of the compounds recited herein. As such, the reagents and reactants can be modified to include the features of reactants to result in the specific compounds provided herein. This includes the reactants having the R group substituents in order to arrive at the synthesized compounds having corresponding R group substituents, and thereby the defined compounds can be used as a roadmap for modifying the synthesis provided herein to arrive at the compounds defined herein and provided by the formulae.

EXAMPLES

Chemical Synthesis of Scheme 1

The first four synthesis steps for Compound 1 were performed by adapting synthetic methods from Hirst et al (Hirst, G.; Rafferty, P., Ritter, K., Calderwood, D., Wishart, N., Arnold. L. D., Frirdman, M. M. Pyrazolopyrimidines as therapeutic agents. US2002156081 (A1).). FIG. 3A shows Scheme 1 for the synthetic route to Compound 1.

Step 1-1 includes the synthesis of 2-Fluoro-3-iodo-4-methyl-N-(3-(trifluoromethyl)phenyl)benzamide.

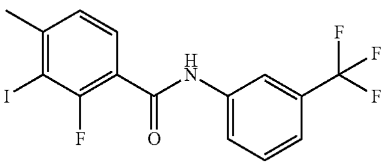 [SMILES: Cc1ccc(C(=O)Nc2cccc(C(F)(F)F)c2)c(F)c1I]

2-Fluoro-3-iodo-4-methyl-N-(3-(trifluoromethyl) phenyl)benzamide (Intermediate 1)

To a solution of 2-fluoro-3-iodo-4-methylbenzoic acid (500 mg, 1.79 mmol, 1 eq) in DMF (6 mL) was added HATU (814.68 mg, 2.14 mmol, 1.2 eq) and DIEA (692.29 mg, 5.36 mmol, 933.00 uL, 3 eq). The mixture was stirred at 25° C. for 30 min. Then 3-(trifluoromethyl)aniline (316.46 mg, 1.96 mmol, 245.31 uL, 1.1 eq) was added to the mixture. The mixture was stirred at 25° C. for 16 h. TLC (PE:EA=5:1, Rf=0.8) and LCMS showed a major peak with desired mass was detected. To the mixture was added water (10 mL) and stirred for 5 min. The aqueous phase was extracted with ethyl acetate (10 mL*3). The combined organic phase was washed with brine (10 mL), dried with anhydrous $Na_2SO_4$, filtered and concentrated in vacuum. The residue was purified by flash silica gel chromatography (ISCO®; 80 g SepaFlash® Silica Flash Column, Eluent of 0-30% Ethyl acetate/Petroleum) to afford 2-fluoro-3-iodo-4-methyl-N-(3-(trifluoromethyl)phenyl)benzamide (500 mg, 1.18 mmol, 66.18% yield) as a white solid. (LCMS: Retention time: 1.085 min, $[M+H]^+$ calcd. for $C_{15}H_{10}F_4INO$ 424.0; found 424.0.)

Step 1-2 includes the synthesis of 2-Fluoro-3-iodo-4-methyl-N-(3-(trifluoromethyl)phenyl)benzothioamide.

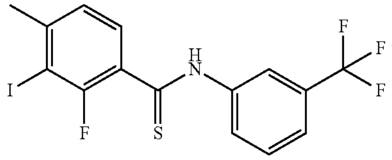 [SMILES: Cc1ccc(C(=S)Nc2cccc(C(F)(F)F)c2)c(F)c1I]

2-Fluoro-3-iodo-4-methyl-N-(3-(trifluoromethyl) phenyl)benzothioamide (Intermediate 2)

A solution of 2-fluoro-3-iodo-4-methyl-N-(3-(trifluoromethyl)phenyl)benzamide (500 mg, 1.18 mmol, 1 eq) in toluene (6 mL) was added LAWESSON'S REAGENT (477.93 mg, 1.18 mmol, 1 eq). The mixture was stirred at 100° C. for 16 h. LCMS (the mixture was stirred at 100° C. for 3 h) showed most of starting material was consumed and desired mass was detected. The reaction mixture was concentrated under reduced pressure to remove toluene. The residue was diluted with DCM 3 mL. The solution was purified by flash silica gel chromatography (ISCO®; 40 g SepaFlash® Silica Flash Column, Eluent of 0-40% Ethyl acetate/Petroleum ether gradient @ 40 mL/min) to afford 2-fluoro-3 odo-4-methyl-N-(3-(trifluoromethyl)phenyl)benzothioamide (400 mg, 901.62 umol, 76.30% yield, 99% purity) as a yellow solid. 1H-NMR (400 MHz, DMSO-d6) ppm=12.30 (s, 1H), 8.45 (s, 1H), 8.16 (d, J=8.0 Hz, 1H), 7.74-7.63 (m, 2H), 7.52 (t, J=7.6 Hz, 1H), 7.27 (d, J=7.6 Hz, 1H), 2.48 (s, 3H). LCMS: Retention time: 1.134 min, [M+H]+ calcd. for C15H10F4INS 440.0; found 440.0.

Step 1-3 includes the synthesis of 2-Fluoro-N'-hydroxy-3-iodo-4-methyl-N-(3-(trifluoromethyl)phenyl)benzimidamide.

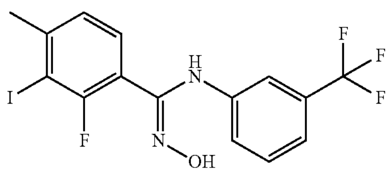 [SMILES: Cc1ccc(/C(=N/O)Nc2cccc(C(F)(F)F)c2)c(F)c1I]

2-Fluoro-N'-hydroxy-3 odo-4-methyl-N-(3-(trifluoromethyl)phenyl)benzimidamide (Intermediate 3)

To a solution of 2-fluoro-3-iodo-4-methyl-N-(3-(trifluoromethyl)phenyl)benzothioamide (400 mg, 910.73 umol, 1 eq) in EtOH (5 mL) was added $NH_2OH$.HCl (2.53 g, 18.21 mmol, 50% purity, 20 eq). The mixture was stirred at 25° C. for 2 h. LCMS showed a major peak with desired mass was detected. The mixture was diluted with ACN (1 mL). The solution was purified by reversed-phase column (0.1% $NH_3$—$H_2O$) to give 2-fluoro-N'-hydroxy-3 odo-4-methyl-N-(3-(trifluoromethyl)phenyl)benzimidamide (350 mg, 772.44 umol, 84.82% yield, 96.7% purity) as a yellow solid. 1H-NMR (400 MHz, DMSO-d6) ppm=10.75 (s, 1H), 8.90 (s, 1H), 7.38 (t, J=7.6 Hz, 1H), 7.30-7.20 (m, 2H), 7.11 (br d, J=8.0 Hz, 1H), 6.96-6.86 (m, 2H), 2.42 (s, 3H). LCMS: Retention time: 1.010 min, [M+H]+ calcd. for C15H11F4IN2O 439.0; found 439.0.

Step 1-4 includes the synthesis of 7-Iodo-6-methyl-N-(3-(trifluoromethyl)phenyl)benzo[d]isoxazol-3-amine.

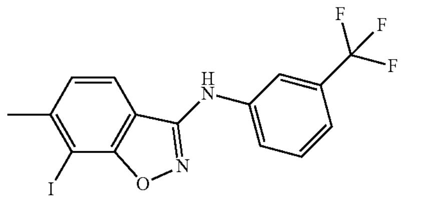 [SMILES: Cc1ccc2c(Nc3cccc(C(F)(F)F)c3)noc2c1I]

7-Iodo-6-methyl-N-(3-(trifluoromethyl)phenyl)benzo[d]isoxazol-3-amine (Intermediate 3)

To a solution of 2-fluoro-N'-hydroxy-3-iodo-4-methyl-N-(3-(trifluoromethyl)phenyl)benzimidamide (160 mg, 365.17 umol, 1 eq) in NMP (5 mL) was added t-BuOK (45.07 mg, 401.68 umol, 1.1 eq). The mixture was stirred at 100° C. for 0.5 h. LCMS showed a major peak with desired mass. The reaction mixture was poured into water (20 mL) and extracted with ethyl acetate (8 mL*3). The combined organic phase was concentrated in vacuum to give a residue. The residue was purified by flash silica gel chromatography (ISCO®; 40 g SepaFlash® Silica Flash Column, Eluent of 0-40% Ethyl acetate/Petroleum ether gradient @ 40 mL/min) to afford 7-iodo-6-methyl-N-(3-(trifluoromethyl)phenyl)benzo[d]isoxazol-3-amine (130 mg, 301.57 umol, 82.58% yield, 97% purity) as a yellow solid. 1H-NMR (400 MHz, DMSO-d6) ppm=9.96 (s, 1H), 8.09 (s, 1H), 7.98 (d, J=8.0 Hz, 1H), 7.90 (br d, J=8.4 Hz, 1H), 7.62 (t, J=7.6 Hz, 1H), 7.38-7.31 (m, 2H), 2.55 (s, 3H). LCMS: Retention time: 1.144 min, [M+H]+ calcd. for C15H10F3IN2O 419.0; found 419.0.

Step 1-5 includes the synthesis of 7-(Imidazo[1,2-b]pyridazin-3-ylethynyl)-6-methyl-N-(3-(trifluoromethyl)phenyl)benzo[d]isoxazol-3-amine (Compound 1).

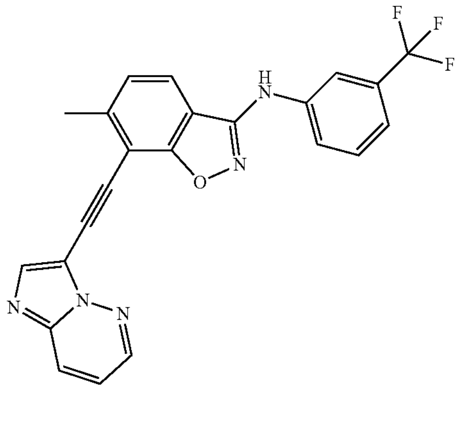 [SMILES: Cc1ccc2c(Nc3cccc(C(F)(F)F)c3)noc2c1C#Cc1cnc2cccnn12]

7-(Imidazo[1,2-b]pyridazin-3-ylethynyl)-6-methyl-N-(3-(trifluoromethyl)phenyl)benzo[d]isoxazol-3-amine (Compound 1)

A mixture of 7-iodo-6-methyl-N-(3-(trifluoromethyl)phenyl)benzo[d]isoxazol-3-amine (101 mg, 241.54 umol, 1 eq), XPhos Pd G3 (122.67 mg, 144.92 umol, 0.6 eq), Cs2CO3 (204.62 mg, 628.00 umol, 2.6 eq) and CuI (23.00 mg, 120.77 umol, 0.5 eq) in anhydrous ACN (2.5 mL). 3-Ethynylimidazo[1,2-b]pyridazine (55.32 mg, 386.46 umol, 1.6 eq) was then added and the reaction mixture was stirred for 2 h at 80° C. under nitrogen atmosphere. LCMS showed desired mass. Reaction mixture was poured into water (20 mL), extracted with ethyl acetate (8 mL*3). The combined organic phase was concentrated in vacuum to give a residue. The residue was purified by flash silica gel chromatography (ISCO®; 24 g SepaFlash® Silica Flash Column, Eluent of 0-100% Ethyl acetate/Petroleum ether gradient @ 40 mL/min). LCMS and HPLC showed the purity is about 75%. After concentration, the residue was purified by prep-HPLC (neutral condition) and lyophilization to afford 7-(Imidazo[1,2-b]pyridazin-3-ylethynyl)-6-methyl-N-(3-(trifluoromethyl)phenyl)benzo[d]isoxazol-3-amine (14.11 mg, 32.56 umol, 13.48% yield, 100% purity) as yellow solid. 1H-NMR (400 MHz, DMSO-d6) ppm=10.04 (s, 1H), 8.79-8.71 (m, 1H), 8.31-8.26 (m, 2H), 8.12 (s, 1H), 8.07 (d, J=8.4 Hz, 1H), 7.92 (br d, J=8.4 Hz, 1H), 7.63 (t, J=8.0 Hz, 1H), 7.46-7.39 (m, 2H), 7.35 (br d, J=7.6 Hz, 1H), 2.70 (s, 3H). LCMS: Retention time: 1.051 min, [M+H]+ calcd. for C23H14F3N5O 434.1; found 434.2. FIG. 1 shows the spectra for 7-(Imidazo[1,2-b]pyridazin-3-ylethynyl)-6-methyl-N-(3-(trifluoromethyl)phenyl)benzo[d]isoxazol-3-amine (Compound 1). F-NMR and LCMS (not shown) confirmed the presence of Compound 1.

FIG. 3B shows a general reaction scheme of Scheme 1 for the synthetic route to the compounds of Formula A and/or Formula B. As shown, the steps are similar to Scheme 1 of FIG. 3A. Step 1-1 includes the Ring 1 reagent and the Ring A reagent being reacted to form Product 1-1 Here, Ring 1 is a ring as defined herein, and Ring A is the Ring A defined herein, along with the R1 and R2 being the substituents as defined herein. As such, the Ring 1 and Ring A reagents can be modified in order to change the specific compound obtained by the synthesis.

The Product 1-1 is then reacted through Step 1-2 with the Lawesson's reagent to obtain Product 1-2. Step 1-3 includes reacting Product 1-2 as shown in FIG. 3A to obtain Product 1-3. Product 1-3 is then reacted through Step 1-4 (see FIG. 3A) to obtain Product 1-4. Product 1-4 is then reacted through Step 1-5 or Step 1-5A with a reagent to obtain the product of Formula A or Formula B. In this example, the $X^1$ is oxygen and the $X^2$ is nitrogen. The $X^6$, $X^7$, and $X^8$ are carbon. However, it should be recognized that the reagents and reactants can be modified in order to introduce one or more hetero atoms into Ring 1.

FIG. 3C shows a modification of Scheme 1 (e.g., Scheme 1A), which uses a different Ring A reactant that results in the Ring A of the product being the structure of Compound 115. Accordingly, variations of Scheme 1 can be implemented to generate the other compounds that fall under Formula A and/or Formula B.

Compound 115 is confirmed by the following spectral data: the yellow solid of Compound 115 (37.82 mg, 83.63 u mol, 34.89% yield, 95.630% purity) was confirmed by 1HNMR (EW13467-173-P1A), CNMR (EW13467-173-P1B), LCMS (EW13467-173-P1B) and HPLC (EW13467-173-P1B); LCMS: Retention time: 1.021 min, (M+H)=433.3, 5-95AB_R_220&254.lcm. EW13467-173-P1B; HPLC: Retention time: 2.403 min, 10-80AB_4 min.lcm. EW13467-173-P1B; NMR: 1H NMR (400 MHz, DMSO-d6) ppm=9.79 (s, 1H), 8.75 (br d, J=4.0 Hz, 1H), 8.28 (br d, J=8.9 Hz, 2H), 8.09 (d, J=8.1 Hz, 1H), 7.88 (s, 1H), 7.76-7.67 (m, 1H), 7.48-7.34 (m, 3H), 7.13 (br d, J=7.7 Hz, 1H), 2.69 (s, 3H), 1.72 (s, 6H).

FIG. 3D shows yet another modification of Scheme 1 (e.g., Scheme 1B), which uses a different Ring A reactant that results in the Ring A of the product being the structure of Compound 118. Accordingly, variations of Scheme 1 can be implemented to generate the other compounds that fall under Formula A and/or Formula B.

Compound 118 is confirmed by the following spectral data: (82.80 mg, 179.74 umol, 51.79% yield, 97.124% purity) was obtained as a yellow solid; LCMS: Retention time: 1.065 min, (M+H)=448.1, 5-95AB_R_220&254.lcm, EW13570-149-P1H; HPLC: Retention time: 2.644 min, 10-80AB_4 min.lcm. EW13570-149-P1E1; NMR: $^{1}$H NMR (400 MHz, DMSO-d6) δ=9.95 (s, 1H), 8.76 (dd, J=1.2, 4.4 Hz, 1H), 8.36-8.26 (m, 2H), 8.07 (d, J=8.2 Hz, 1H), 7.92 (s, 1H), 7.75 (s, 1H), 7.47-7.40 (m, 2H), 7.18 (s, 1H), 2.70 (s, 3H), 2.44 (s, 3H). EW13570-149-PIN; $^{19}$F NMR (400 MHz, DMSO-d6) δ=61.295. EW13570-149-P1N; $^{13}$C NMR (400 MHz, DMSO-d6) δ=161.563, 155.628, 145.641, 143.644, 141.638, 140.513, 130.380, 130.070, 126.654, 125.757, 122.203, 121.934, 119.724, 118.624, 115.265, 111.507, 104.748, 91.117, 86.381, 40.629, 40.425, 40.262, 40.213, 40.010, 39.798, 39.586, 39.382, 21.618, 20.658. EW13570-149-P1N1.

FIG. 3E shows still yet another modification of Scheme 1 (e.g., Scheme 1C), which uses yet another Ring A reactant that results in the Ring A of the product being the structure of Compound 119. Accordingly, variations of Scheme 1 can be implemented to generate the other compounds that fall under Formula A and/or Formula B.

Compound 119 is confirmed by the following spectral data: (16.52 mg, 30.46 umol, 25.29% yield, 94.663% purity) was obtained as a off-white solid; LCMS: Retention time: 0.879 min, (M+H)=514.2, 5-95AB_R_220&254.lcm, EW13570-167-P1H1; HPLC: Retention time: 2.630 min, 10-80CD_4 min.lcm. EW13570-167-P1F1; NMR: $^{1}$H NMR (400 MHz, DMSO-d6) δ=10.29 (s, 1H), 8.77 (d, J=2.8 Hz, 1H), 8.34-8.27 (m, 2H), 8.23 (d, J=1.3 Hz, 1H), 8.12 (s, 1H), 8.06 (d, J=8.1 Hz, 1H), 7.98 (s, 1H), 7.63 (s, 1H), 7.50 (s, 1H), 7.47 (d, J=8.3 Hz, 1H), 7.43 (dd, J=4.5, 9.2 Hz, 1H), 2.71 (s, 3H), 2.21 (s, 3H). EW13570-167-P1M; $^{19}$F NMR (400 MHz, DMSO-d6) δ=61.429. EW13570-167-P1M.

Chemical Synthesis of Scheme 2

FIG. 4A shows reaction Scheme 2 for use in preparing Compound 110. FIG. 4B shows the general reaction scheme based on Scheme 2 for preparing the compounds of Formula 29, which falls under the other general formulae provided herein (e.g., such as also under Formula A, Formula B, etc.).

In Scheme 2, 2-fluoro-4-methylbenzonitrile is reacted with n-BuLi and 12 in the presence of 2,2,6,6-tetramethylpiperidine to form 2-fluoro-3-iodo-4-methylbenzonitrile (Product 2-1). Product 2-1 is reacted through Step 2-2 as shown to obtain 7-iodo-6-methylbenzo[d]isoxazol-3-amine (Product 2-2). Product 2-2 is reacted through Step 2-3 with (3-formyl-5-(trifluoromethyl)phenyl)boronic acid (e.g., variation of Ring A) to obtain 3-((7-iodo-6-methylbenzo[d]isoxazol-3-yl)amino)-5-(trifluoromethyl)benzaldehyde (Product 2-3). Product 2-3 is then reacted through Step 2-4 with 1-methylpiperazine (e.g., an embodiment of R2) to obtain 7-iodo-6-methyl-N-(3-((4-methylpiperazin-1-yl)methyl)-5-(trifluoromethyl)phenyl)benzo[d]isoxazol-3-amine (Product 2-4). Product 2-4 is reacted with 3-ethynylimidazo[1,2-b]pyridazine (e.g., embodiment of Ring B or Ring B/C polycycle through Step 2-5 to obtain Compound 110.

Compound 110 is confirmed by the following spectral data: (11.01 mg, 19.22 umol, 12.74% yield, 95.249% purity) confirmed by LCMS (EW13564-254-P1D), HPLC (EW13564-254-P1J1), HNMR (EW13564-254-P1E1), FNMR (EW13564-254-P1E1), 1HNMR (EW13564-254-P1G) as yellow solid; and LCMS: Retention time: 0.875 min, (M+H)=546.3, 5-95AB_R_220&254_50.lcm; NMR: 1H NMR (400 MHz, DMSO-d6) ppm=10.11 (s, 1H), 9.49 (br s, 1H), 8.76 (dd, J=1.4, 4.4 Hz, 1H), 8.36-8.26 (m, 2H), 8.10 (d, J=8.0 Hz, 1H), 8.02 (s, 1H), 7.95 (s, 1H), 7.48-7.40 (m, 2H), 7.31 (s, 1H), 3.69 (s, 2H), 3.03 (br s, 4H), 2.77 (br s, 3H), 2.70 (s, 3H).

FIG. 4B shows a general reaction scheme of Scheme 2 for the synthetic route to the compounds of Formula 29, and which also falls under Formula A and/or Formula B. The steps and conditions are similar to Scheme 2, but where the substituents on the reactants may be varied to arrive at the different compounds under the formulae provided herein. Steps 2-1 and 22 can be identical, but may include modification to the reactants, to obtain Product 2-2 as shown with the variables being as defined herein. Product 2-2 is reacted with Reagent 2-2 through Step 2-3 to obtain Product 2-3, which includes the variables as defined herein. Product 2-3 is reacted with Reagent 2-3 (e.g., embodiment of R2) to form Product 2-4. The Product 2-4 is reacted with reacted with a reactant (e.g., Ring B reagent or Ring B/C reagent) through Step 2-5 (e.g., Step 2-5A or Step 2-5B) to obtain a compound of Formula 29A and/or Formula 29B.

The Scheme 2 can be further modified as shown in FIG. 4C, Scheme 2C, to obtain Compound 111. As shown in FIG. 4C, Product 2-3 of Scheme 1 is reacted through Step 2-4A with morpholine to obtain 7-iodo-6-methyl-N-(3-(morpholinomethyl)-5-(trifluoromethyl)phenyl)benzo[d]isoxazol-3-amine (Product 2-4C). Product 2-4C is then reacted as shown to obtain Compound 111.

Compound 111 is confirmed by the following spectral data: (7.11 mg, 12.80 umol, 22.07% yield, 95.881% purity) as yellow solid confirmed by LCMS (EW13564-234-P1F3), HPLC (EW13564-234-PIJ2), HNMR (EW13564-234-P1E1), FNMR (EW13564-234-P1F); LCMS: Retention time: 0.863 min, (M+H)=533.3, 5-95AB_R_220&254_50.1 cm, EW13564-234-P1F3; NMR: 1H NMR (400 MHz, CHLOROFORM-d) ppm=8.55-8.50 (m, 1H), 8.15 (s, 1H), 8.06-7.99 (m, 1H), 7.80 (s, 2H), 7.46 (d, J=8.1 Hz, 1H), 7.30

(s, 1H), 7.17 (dd, J=4.4, 9.0 Hz, 1H), 6.57 (s, 1H), 3.79-3.70 (m, 4H), 3.58 (s, 2H), 2.76 (s, 3H), 2.54-2.44 (m, 4H).

FIG. 4D shows another example of Scheme 2, Scheme 2D, that produces Compound 112. Product 2-3 of Scheme 1 is reacted with cyclopropanamine (e.g., embodiment of $R^2$ through Step 2-4D as shown to obtain N-(3-((cyclopropylamino)methyl)-5-(trifluoromethyl)phenyl)-7-iodo-6-methylbenzo[d]isoxazol-3-amine (Product 2-4D). Product 2-4D is then reacted through Step 2-5D as shown to obtain Compound 112.

Compound 112 is confirmed by the following spectral data: (15.58 mg, 29.49 u mol, 41.05% yield, 95.098% purity) as a yellow solid was obtained by 1HNMR (EW13467-171-P1A1), FNMR (EW13467-171-PIA), LCMS (EW13467-171-P1C) and HPLC (EW13467-171-P1A1); LCMS: Retention time: 0.868 min, (M+H)=503.3, 5-95AB_R_220&254.lcm. EW13467-171-P1C; HPLC: Retention time: 1.909 min, 10-80AB_4 min.lcm. EW13467-171-P1A1; NMR: 1H NMR (400 MHz, DMSO-d6) ppm=10.05 (s, 1H), 8.75 (br d, J=3.8 Hz, 1H), 8.36-8.20 (m, 2H), 8.14-8.01 (m, 2H), 7.86 (s, 1H), 7.48-7.36 (m, 2H), 7.30 (s, 1H), 3.84 (br s, 2H), 2.68 (s, 3H), 2.09 (br s, 1H), 0.50-0.13 (m, 4H). EW13467-171-P1A1.

FIG. 4E shows another example of Scheme 2, Scheme 2E, that produces Compound 113. Product 2-3 of Scheme 1 is reacted with a reactant pyrrolidine (e.g., embodiment of $R^2$) through Step 2-4E to obtain 7-iodo-6-methyl-N-(3-(pyrrolidin-1-ylmethyl)-5-(trifluoromethyl)phenyl)benzo[d]isoxazol-3-amine (Product 2-4E). Product 2-4E is then reacted as shown through Step 2-5E to obtain Compound 113.

Compound 113 is confirmed by the following spectral data: (5.01 mg, 7.85 umol, 7.87% yield, 98.825% purity, TFA) as yellow solid confirmed by LCMS (EW13564-255-P1C), HPLC (EW13564-255-P1L), HNMR (EW13564-255-P1H), FNMR (EW13564-255-P1H); LCMS: Retention time: 0.878 min, (M+H)=517.3, 5-95AB_R_220&254_50.lcm, EW13564-255-P1C; NMR: 1H NMR (400 MHz, METHANOL-d4) ppm=9.81 (s, 1H), 8.68 (d, 1=4.4 Hz, 1H), 8.34 (s, 1H), 8.19-8.11 (m, 2H), 7.99 (s, 1H), 7.94 (d, J=8.1 Hz, 1H), 7.50 (s, 1H), 7.46-7.35 (m, 2H), 4.53 (s, 2H), 3.60 (br s, 2H), 3.31-3.23 (m, 2H), 2.77 (s, 3H), 2.25 (brs, 2H), 2.05 (br d, 1=16.6 Hz, 2H).

FIGS. 4A and 4C-4E provide examples of the general scheme of FIG. 4B, which shows that the compounds described herein can be prepared by making modifications to the reactants in order to achieve the different rings and substituents of the recited compounds.

Chemical Synthesis of Schemes A, B, and C

FIG. 5A shows reaction Scheme A for use in preparing an embodiment of Ring A that can be reacted with the compound of Core A to arrive at Compound 114. FIG. 5B shows reaction Scheme B for use in preparing a different embodiment of Ring A, which also can be reacted with the compound of Core A to arrive at Compound 116. FIG. 5C shows reaction Scheme C for use in preparing yet a different embodiment of Ring A, which can be reacted with the compound of Core A to arrive at Compound 117. Accordingly, various reaction schemes can be used to prepare an embodiment of Ring A, which then can be reacted with the compound of Core A to form an inhibitor compound as described herein.

FIG. 5A shows that 1-bromo-3-(bromomethyl)-5-(trifluoromethyl)benzene can be reacted with 1H-imidazole in the presence of acetone and K2CO3 to arrive at 1-(3-bromo-5-(trifluoromethyl)benzyl)-1H-imidazole (Product A1). Product A1 is then reacted with 7-(imidazo[1,2-b]pyridazin-3-ylethynyl)-6-methylbenzo[d]isoxazol-3-amine (i.e., Core A) through step A2 to arrive at Compound 114.

Compound 114 is confirmed by the following spectral data: (9.45 mg, 14.67 umol, 8.49% yield, 97.391% purity, TFA) as yellow solid was confirmed by LCMS (EW13564-273-P1J2), HPLC (EW13564-273-P1J1) and 1 HNMR (EW13564-273-P1E), FNMR (EW13564-273-P1E); LCMS: Retention time: 0.870 min, (M+H)=514.3, 5-95AB_R_220&254_50.lcm, EW13564-273-P1J2; NMR: 1H NMR (400 MHz, METHANOL-d4) ppm=9.17 (s, 1H), 8.67 (dd, J=1.4, 4.4 Hz, 1H), 8.21-8.07 (m, 3H), 7.98-7.85 (m, 2H), 7.74 (t, J=1.6 Hz, 1H), 7.65 (s, 1H), 7.41 (dd, J=4.4, 9.2 Hz, 1H), 7.38-7.32 (m, 2H), 5.60 (s, 2H), 2.74 (s, 3H).

FIG. 5B shows 1-bromo-3-fluoro-5-(trifluoromethyl)benzene is reacted with ethyl 2-cyanoacetate in the presence of NaH, NMP to obtain ethyl 2-(3-bromo-5-(trifluoromethyl)phenyl)-2-cyanoacetate (Product B-1). Product B-1 is reacted with HCl with water and dioxane to obtain 2-(3-bromo-5-(trifluoromethyl)phenyl)acetonitrile (Product B-2). Product B-2 is reacted with $CH_3I$ and t-BuOK in THF to obtain 2-(3-bromo-5-(trifluoromethyl)phenyl)-2-methylpropanenitrile (Product B-3). Product B-3 is reacted with Core A in the identified conditions to obtain Compound 116.

Compound 116 is confirmed by the following spectral data: (2.69 mg, 4.91 umol, 2.84% yield, 99.690% purity, FA) as yellow solid confirmed by LCMS (EW13564-275-P1J2), HPLC (EW13564-275-P1J1) and 1 HNMR (EW13564-275-P1F), F HNMR (EW13564-275-P1F); LCMS: Retention time: 1.051 min, (M+H)=501.2, EW13564-275-P1J2; NMR: 1H NMR (400 MHz, DMSO-d6) ppm=10.29 (s, 1H), 8.77 (dd, J=1.5, 4.4 Hz, 1H), 8.42 (br s, 1H), 8.33-8.27 (m, 2H), 8.14 (br d, J=5.6 Hz, 2H), 8.08 (d, 0.1=8.1 Hz, 1H), 7.48-7.38 (m, 3H), 2.71 (s, 3H), 1.78 (s, 6H).

FIG. 5C shows 1,3-dibromo-5-(bromomethyl)benzene being reacted with NaCN in ethanol and DMF in Step C-1 to obtain 2-(3,5-dibromophenyl)acetonitrile (Product C-1). Product C-1 is reacted with $CH_3I$ and t-BuOK in THF to obtain 2-(3,5-dibromophenyl)-2-methylpropanenitrile (Product C-2). Product C-2 is reacted with N-BuLi in DMF and THF through Step C-3 to obtain 2-(3-bromo-5-formylphenyl)-2-methylpropanenitrile (Product C-3). Product C-3 is reacted with morpholine in methanol and with $NaBH_3CN$ through Step C-4 to obtain 2-(3-bromo-5-(morpholinomethyl)phenyl)-2-methylpropanenitrile (Product C-4). Product C-4 is then reacted with Core A as shown in Step C-4 to obtain Compound 117.

Compound 117 is confirmed by the following spectral data: (2.53 mg, 3.92 u mol, 2.27% yield, 100.000% purity, TFA) as a yellow solid was confirmed by 1HNMR (EW13467-191-P1A1), LCMS (EW13467-191-P1C1) and HPLC (EW13467-191-P1A1); LCMS: Retention time: 0.837 min, (M+H)=532.1, 5-95AB_R_220&254.lcm EW13467-191-P1C1; HPLC: Retention time: 1.828 min, 10-80AB_4 min.lcm. EW13467-191-P1A1; NMR: 1H NMR (400 MHz, DMSO-d6) ppm=10.03 (s, 1H), 8.75 (dd, J=1.5, 4.4 Hz, 1H), 8.32-8.25 (m, 2H), 8.09 (d, J=8.1 Hz, 1H), 7.94-7.84 (m, 2H), 7.47-7.40 (m, 2H), 7.30 (s, 1H), 4.41 (br s, 2H), 3.97 (br s, 2H), 3.66 (br s, 1H), 3.19 (br s, 4H), 2.70 (s, 3H), 1.75 (s, 6H).

Chemical Synthesis of Scheme 3

Figure 6C:
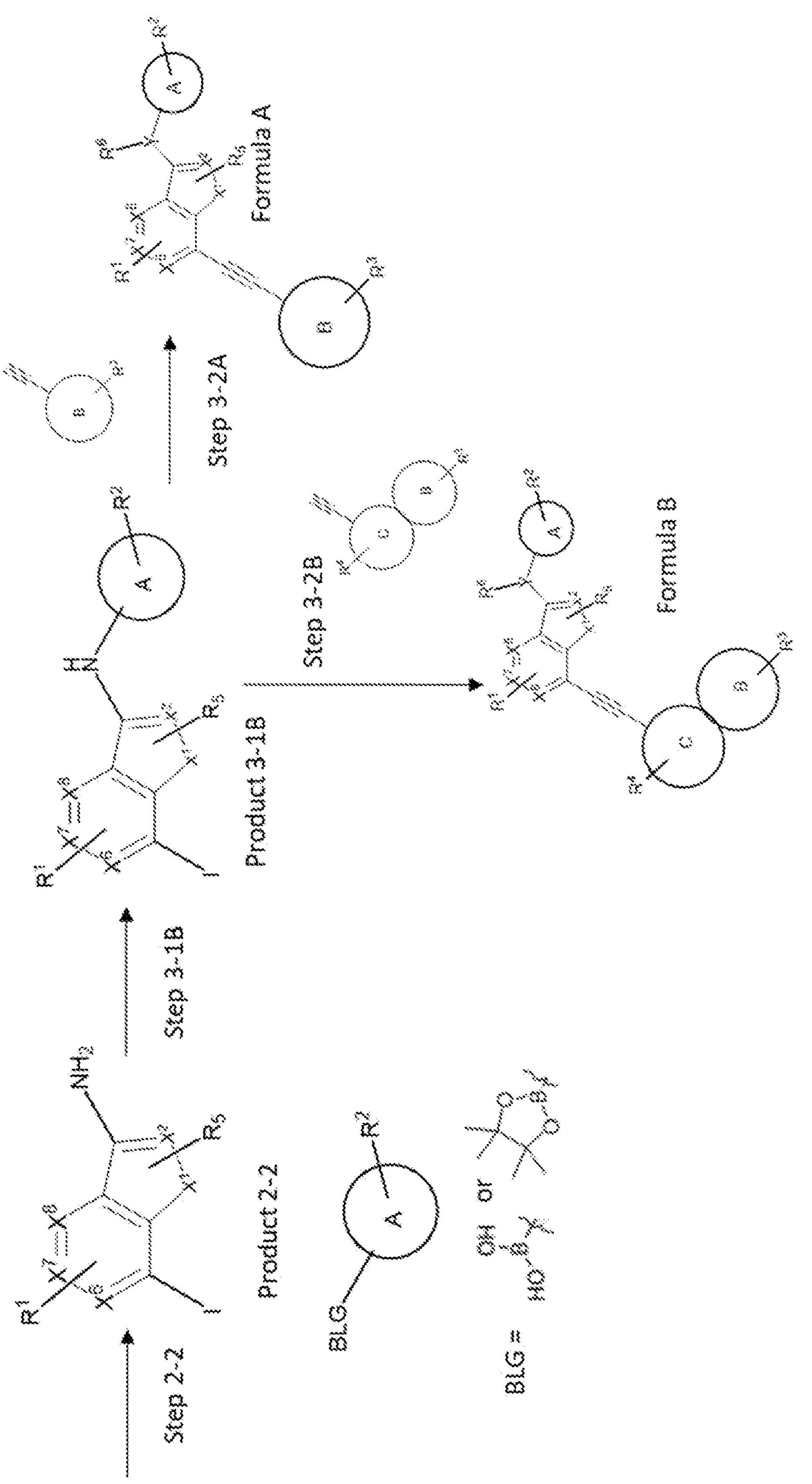
FIG. 6C shows a general reaction scheme based on Scheme 3 for the synthetic route to compounds under Formula A and/or Formula B.

FIG. 6A shows reaction Scheme 3 for use in preparing Compound 120. FIG. 6B shows the reaction Scheme 3A for use in preparing Compound 121. FIG. 6C shows a general reaction scheme based on Schemes 3A and 3B for preparing the compounds of Formula A and Formula B, as well as others.

FIG. 6A shows that the Product 2-2 from Step 2-2 can be used in a different reaction pathway to generate the compounds described herein. Product 2-2 is reacted through Step 3-1 with (3-(trifluoromethoxy)phenyl)boronic acid as shown to obtain 7-iodo-6-methyl-N-(3-(trifluoromethoxy)phenyl) benzo[d]isoxazol-3-amine (Product 3-1). Product 3-1 is reacted with 3-ethynylimidazo[1,2-b]pyridazine as shown in Step 3-2 to obtain Compound 120.

Compound 120 is confirmed by the following spectral data: (60.68 mg, 133.24 umol, 57.85% yield, 98.676% purity) as yellow solid confirmed by LCMS (EW13564-237-P1E1), HPLC (EW13564-237-P1J), HNMR (EW13564-234-P1E1), FNMR (EW13564-234-P1F), CNMR (EW13564-237-PIG); LCMS: Retention time: 1.049 min, (M+H)=450.2, 5-95AB_R_220&254_50.lcm, EW13564-237-P1E1; NMR: 1H NMR (400 MHz, DMSO-$d_6$) ppm=9.98 (s, 1H), 8.75 (dd, J=1.2, 4.4 Hz, 1H), 8.37-8.24 (m, 2H), 8.06 (d, 1=8.1 Hz, 1H), 7.80 (br s, 1H), 7.64 (br d, J=8.3 Hz, 1H), 7.51 (t, J=8.2 Hz, 1H), 7.47-7.36 (m, 2H), 6.98 (br d, J=7.8 Hz, 1H), 2.69 (s, 3H).

FIG. 6B shows that the Product 2-2 from Step 2-2 can be used in a different reaction pathway to generate the compounds described herein. Product 2-2 is reacted through Step 3-1A with 3-(4,4,5,5-tetramethyl-1,3,2-dioxaborolan-2-yl)-5-(trifluoromethyl)pyridine as shown to obtain 7-iodo-6-methyl-N-(5-(trifluoromethyl)pyridin-3-yl)benzo[d]isoxazol-3-amine (Product 3-1A). Product 3-1A is reacted with 3-ethynylimidazo[1,2-b]pyridazine as shown in Step 3-2 to obtain Compound 121.

Compound 121 is confirmed by the following spectral data: (77.80 mg, 170.11 umol, 35.65% yield, 94.975% purity) was obtained as a yellow solid; LCMS: Retention time: 0.973 min, (M+H)=435.2, 5-95AB_R_220&254.lcm, EW13570-150-P1H2; HPLC: Retention time: 2.360 min, 10-80AB_4 min.lcm. EW13570-150-P1E2; NMR: NMR (400 MHz, DMSO-d6) δ=10.42-10.30 (m, 1H), 9.21-8.99 (m, 1H), 8.83-8.73 (m, 1H), 8.70-8.55 (m, 1H), 8.52 (br s, 1H), 8.29 (br d, J=9.2 Hz, 2H), 8.05 (d, J=8.2 Hz, 1H), 7.51-7.38 (m, 2H), 3.18 (d, J=5.3 Hz, 1H), 2.70 (s, 3H). EW13570-150-P1N; $^{19}$F NMR (400 MHz, DMSO-d6) δ=61.193. EW13570-150-P1N; $^{32}$C NMR (400 MHz, DMSO-d6) δ=161.734, 155.563, 145.666, 143.970, 143.538, 138.467, 126.662, 126.059, 122.129, 120.523, 120.442, 119.757, 114.955, 104.895, 90.954, 86.552, 49.075, 40.817, 40.686, 40.474, 40.262, 40.010, 39.798, 39.594, 39.382, 33.520, 20.688, 161.60, 142.23, 139.27, 138.30, 138.21, 135.91, 134.62, 134.22, 133.69, 130.07, 129.81, 129.73, 128.77, 128.36, 125.94, 124.57, 124.53, 122.99, 120.26, 115.53, 115.31, 113.28, 113.06, 109.24, 42.50, 42.13, 42.11, 18.95. EW13570-150-P1N1.

FIG. 6C shows a general reaction scheme of Scheme 2 for the synthetic route to the compounds that fall under Formula A and/or Formula B, as well as others. Here, a generic version of the reaction in Step 2-2 with an appropriate compound with the appropriate substituents is performed to obtain Product 2-2 as per FIG. 4B, where the variables are as defined herein. Step 3-1B includes reacting Product 2-2 under the conditions of FIGS. 6A-6B with the embodiment of the boron leaving group (BLG) substituted Ring A to obtain Product 3-1B as shown with the variables as defined herein. Product 3-1B can be reacted through either Step 3-2A to obtain compounds of Formula A or reacted through Step 3-2B to obtain compounds of Formula B.

Chemical Synthesis of Scheme 4

Figure 7:
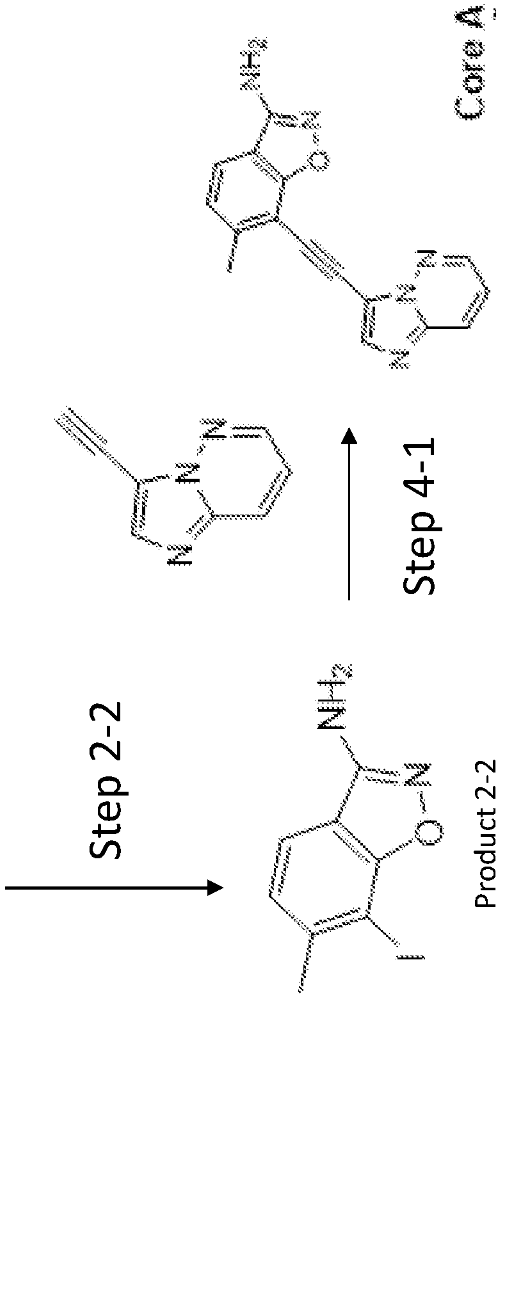
FIG. 7 shows Scheme 4 for the synthetic route to the compound Core A, which can then be further reacted to obtain the compounds described herein.

FIG. 7 shows that the Product 2-2 from Step 2-2 can be used in a different reaction pathway under Scheme 4 to generate the compounds described herein. Product 2-2 is reacted through Step 4-1 with 3-ethynylimidazo[1,2-b] pyridazine as shown to obtain Core A.

The foregoing synthetic routes show that a number of synthetic pathways and protocols can be used to prepare the compounds described herein.

DDR1 Human TK Kinase Enzymatic Radiometric Assay 110 μM ATP1, KinaseProfiler

The obtained 7-(Imidazo[1,2-b]pyridazin-3-ylethynyl)-6-methyl-N-(3-(trifluoromethyl)phenyl)benzo[d]isoxazol-3-amine (Compound 1) was tested for activity as a DDR1 antagonist to show the function as a DDR1 inhibitor. DDR1 (h) is incubated with 8 mM MOPS pH 7.0, 0.2 mM EDTA, 250 uM IGF 1Rtide protein kinase substrate (e.g., derived from human IRS-1, and is a substrate for TRK1, JAK2, and RET Kinases—enzolifesciences.com/BML-P257/igf-1rtide/), 10 mM Magnesium acetate and [gamma-33P]-ATP (specific activity and concentration as required). The reaction is initiated by the addition of the Mg/ATP mix. After incubation for 40 minutes at room temperature, the reaction is stopped by the addition of phosphoric acid to a concentration of 0.5%. 10 uL of the reaction is then spotted onto a P30 filtermat and washed four times for 4 minutes in 0.425% phosphoric acid and once in methanol prior to drying and scintillation counting. A control inhibitor was staurosporine.

Figure 2:
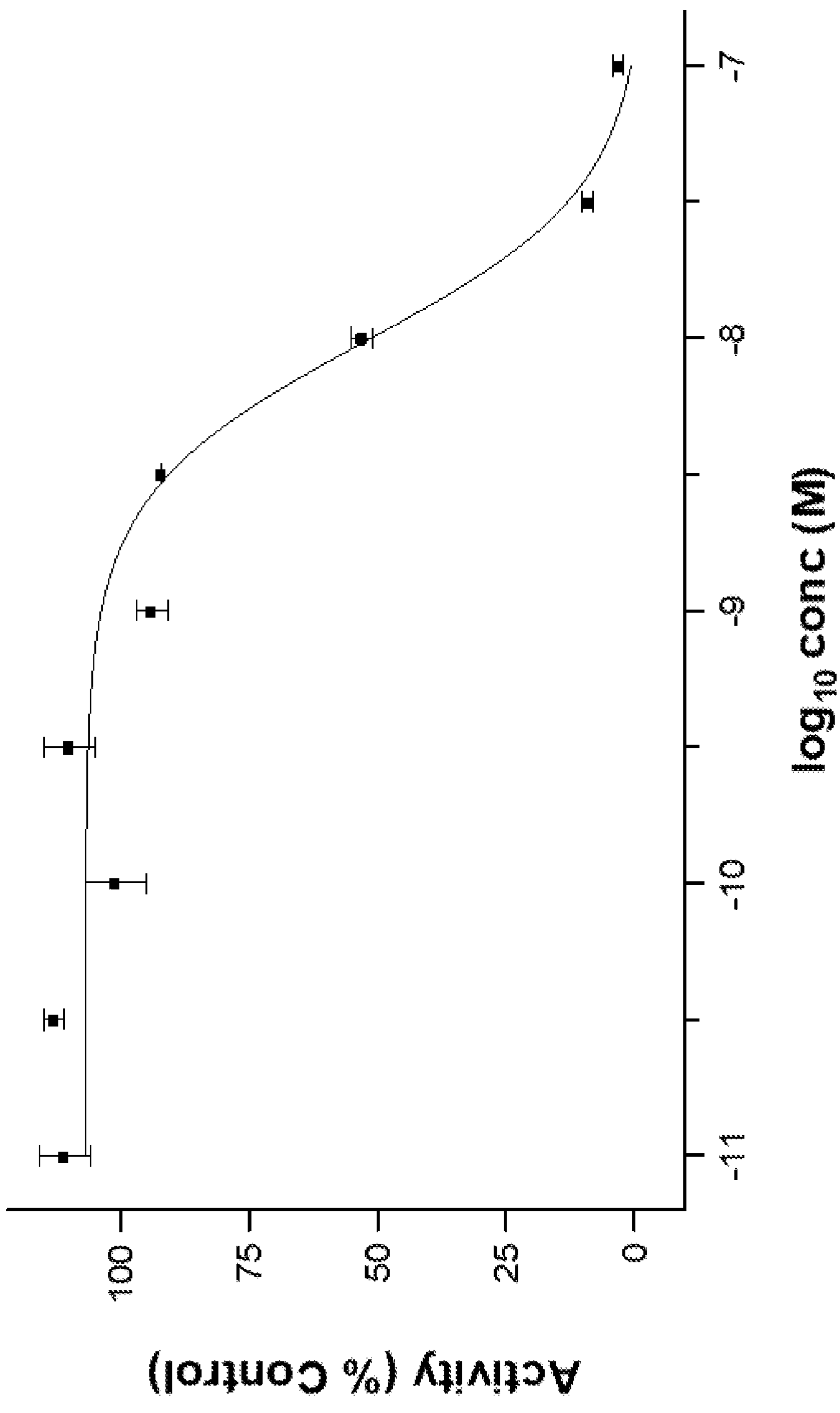
FIG. 2 shows DDR1 inhibitor activity versus the $\log_{10}$ concentration (M).

The activity versus the log 10 concentration (M) is shown in FIG. 2 for Compound 1. It was determined that Compound 1 has an IC50 of 10 nM for human DDR1. Therefore, Compound 1 is a DDR1 Inhibitor and Antagonist.

Biochemical Assay

The activity of the inhibitor compounds against DDR1 and DDR2 was tested using KinaseProfiler (Eurofins). Human DDR1/DDR2 kinase was incubated with 8 mM MOPS buffer (pH=7.0), 0.2 mM EDTA, 250 μM IGF 1Rtide protein kinase substrate (e.g., derived from human IRS-1, and is a substrate for TRK1, JAK2, and RET Kinases—enzolifesciences.com/BML-P257/igf-1rtide/), 10 mM Magnesium acetate/Manganese chloride, respectively, and [γ-$^{33}$P]-ATP. The enzymatic reaction processed in the presence of $Mg^{2+}$ cations and ATP at room temperature for 40 minutes and terminated by addition of phosphoric acid. The reaction mixture (10 μL) was spotted onto a P30 filtermat and washed four times using 0.425% phosphoric acid and once with methanol. All the compounds were prepared in 100% DMSO. Staurosporine was used as a reference inhibitor and was added to each plate at an estimated concentration resulted in complete inhibition. The results for some of the compounds are listed in Table 1, which shows the ability to inhibit DDR1 and DDR2. As such, these compounds be used as inhibitors of the discoidin domain receptor family, such as for DDR1 and DDR2. However, these compounds may also inhibit other DDR family receptors.

TABLE 1

DDR1/DDR2 Enzymatic Assay (IC50, nM).

| Compound ID | DDR1 Enzymatic Assay IC50(nM) |
|---|---|
| Compound 110 | 17.29 |
| Compound 119 | 105.93 |
| Compound 120 | 14.61 |
| Compound 121 | 7.36 |
| Compound 111 | 24.50 |
| Compound 112 | 11.48 |
| Compound 113 | 12.06 |
| Compound 114 | 13.96 |
| Compound 115 | 19.34 |

TABLE 1-continued

DDR1/DDR2 Enzymatic Assay (IC50, nM).

| Compound ID | DDR1 Enzymatic Assay IC50(nM) |
| --- | --- |
| Compound 116 | 25.80 |
| Compound 117 | 29.06 |
| Compound 118 | 13.65 |
| Compound 1 | 9.72 |

Auto-Phosphorylation

Human DDR1b gene with HA-tag was cloned into pCMV Tet-On vector (Clontech) and stable inducible cell lines established in U2OS were used for the IC50 test. The cells were seeded in 12-well plates and DDR1b expression was induced with 10 ug/ml doxycycline (Selleckchem #54163) for 48 hrs at 37° C. in a humidity controlled incubator with 5% CO2 prior to DDR1 activation by rat tail collagen I (sigma #11179179001). The cells were detached with trypsinization and transferred to a 15-ml tube. Then, after being pre-treated with compound for 0.5 hr, the cells were treated with compounds in the presence of 10 ug/ml rat tail collagen I for 1.5 hrs at 37° C. At the end of the treatment, each sample was washed with cold PBS one time and lysed in R1PA buffer with protease and phosphatase inhibitors (Sigma #0278, Sigma #P5726 and Sigma #P0044) for 20 min at 4° C. The lysates were cleared by centrifugation and the supernatants were subject to Western blot analysis for the activated human DDR1b (Y513) (Cell Signaling #14531S), total DDR1b (HA-tag, sigma #H9658) after stripping, and GAPDH. The integrated intensity of each band was quantified and the $IC_{50}$ of test compounds were calculated on a 10-point 3-fold dilution series. The results for some of the compounds are listed in Table 2, which shows the ability to inhibit phosphorylation of DDR1b (Y513). As such, these compounds be used as inhibitors of phosphorylation the discoidin domain receptor family, such as for DDR1. However, these compounds may also inhibit phosphorylation of other DDR family receptors.

TABLE 2

Inhibition of Auto-Phosphorylation of DDR1b Assay (IC50, nM).

| Compound ID | Y513 Auto-phosphorylation Inhibition IC50(nM) |
| --- | --- |
| Compound 110 | 5.10 |
| Compound 119 | 5.50 |
| Compound 120 | 3.70 |
| Compound 121 | 4.10 |
| Compound 111 | 5.60 |
| Compound 112 | 4.40 |
| Compound 113 | 2.80 |
| Compound 114 | 15.00 |
| Compound 115 | 2.40 |
| Compound 116 | 40.00 |
| Compound 117 | 4.70 |
| Compound 118 | 8.60 |
| Compound 1 | 9.70 |

LX-2 Fibrosis Assay

Human hepatic stellate cell LX-2 were grown in DMEM (Invitrogen, 11960) supplied with 1% MEM Non-Essential Amino Acids (Invitrogen, 11140-050), 2% fetal bovine serum (Hyclone, SV30087.03), Penicillin (100 U/mL)-streptomycin (100 μg/mL) (Millipore, TMS-AB2-C) and 2 mM L-Glutamine (Invitrogen, 25030-001). After the cells grew in 12-well plates for 24 hours, the cell culture medium was changed to the same as above except using 0.4% fetal bovine serum. After 20 hour growth in the reduced serum medium, the cells were treated with indicated doses of compounds for 30 minutes. Subsequently, the cells were stimulated with 4 ng/mL TGF-b (R&D Systems, 240-B-002) for 48 hours. The cells were rinsed twice with DPBS before being harvested with 100 μL RIPA buffer (Sigma, R0278) supplemented with protease inhibitor cocktail (Roche, 04693132001) at 4° C. The total protein in each sample was quantified using BCA Protein Assay Kit (Pierce™, 23227) and equal amount of total protein of each sample was subject to Western blot analysis. Antibodies used were mouse anti-α-Actin (SPM332) (sc-365970), mouse anti-CTGF (E5) (sc-365970), and mouse anti-collagen α1 (3G3) (sc-293182), from Santa Cruz Biotechnologies; and mouse anti-GAPDH (6C5) (EMD Millipore, MAB374). The results for some of the compounds are listed in Table 3, which shows the ability to inhibit collagen production, which thereby indicates inhibition of fibrosis. Accordingly, by inhibiting collagen production, the compounds inhibit the underlying mechanism of diseases related to over production of collagen, such as fibrosis. As such, these compounds be used as inhibitors of fibrosis by inhibiting function of the discoidin domain receptor family.

TABLE 3

Inhibition of Collagen Production (IC50, nM).

| Compound ID | Inhibition of Collagen Production in LX-2 Cells IC50(nM) |
| --- | --- |
| Compound 110 | ND |
| Compound 119 | ND |
| Compound 120 | 2947 |
| Compound 121 | 62 |
| Compound 111 | 1951 |
| Compound 112 | 1662 |
| Compound 113 | 2576 |
| Compound 114 | ND |
| Compound 115 | 502 |
| Compound 116 | ND |
| Compound 117 | 160 |
| Compound 118 | ND |
| Compound 1 | 13 |

Cytotoxicity

LX-2 cells were seeded into 96 well plates in the presence of compounds and allowed to grow for 72 hours before CellTiter-Glo® Luminescent Cell Viability Assay was carried out according the manufacturer's instruction. $CC_{50}$ was calculated on a 10 dose 3-fold compound dilution series using GraphPad Prism software. The results for some of the compounds are listed in Table 4, which shows the CC50 (μM), which is the concentration of the compound that kills half of the cells in the cell culture. The higher the value, the more toxic the compound.

Toxicity of Compounds (CC50, μM).

| Compound ID | LX-2 Cells Cytotoxicity CC50(uM) |
| --- | --- |
| Compound 110 | ND |
| Compound 119 | ND |

-continued

| Toxicity of Compounds (CC50, μM). | |
|---|---|
| Compound ID | LX-2 Cells Cytotoxicity CC50(uM) |
| Compound 120 | 2.414 |
| Compound 121 | >40.0 |
| Compound 111 | >42.335 |
| Compound 112 | 1.363 |
| Compound 113 | 4.252 |
| Compound 114 | ND |
| Compound 115 | 1.901 |
| Compound 116 | ND |
| Compound 117 | >57.2 |
| Compound 118 | ND |
| Compound 1 | 3 |

Cholangiocarcinoma (Bile Duct Cancer)

Three compounds (e.g., two test compounds—Compound 1 and Compound 121, compared to control Dasatinib) were studied in primary tumor cells freshly isolated from patient derived xenograft tumor model using tumor chemosensitivity assay (TCA). All the compounds were tested starting from 30 μM, 3-fold serial dilution.

Add 195 μL of assay medium into each well of the V-bottom plate; then transfer 5 μL of the stock compound solution of each concentration from the stock plate (400× stock). Add 5 μL of DMSO into the Blank and Control wells. Pipette up and down to mix well. This V-plate is designated as the 10× concentrate compound plate.

For cell viability test, add compounds as below. Then incubate the plates at 37° C., 5% CO2, 95% air and 100% relative humidity for 3 days or 6 days. For day 0 plate, add 15 μL of the DMSO-medium into the Control wells. The final DMSO concentration was 0.25%. Proceed to cell viability assay. For TCA plates, add 15 μL of the compound-medium from the 10× concentrate compound plate into the cells in 96-well assay plate according to the plate map. Add 15 μL of the DMSO-medium into the Blank and Control wells. The final DMSO concentration was 0.25%.

The procedures were performed according to the Promega CellTiter-Glo Luminescent Cell Viability Assay Kit (Promega-G7573): Thaw the CellTiter-Glo buffer and equilibrate to room temperature prior to use; Equilibrate the lyophilized CellTiter-Glo Substrate to room temperature prior to use; Transfer the entire liquid volume of CellTiter-Glo Buffer into the amber bottle containing CellTiter-Glo Substrate to reconstitute the lyophilized enzyme/substrate mixture. This forms the CellTiter-Glo Reagent; Mix by gently vortexing to obtain a homogeneous solution; Equilibrate the plate and its contents to room temperature for approximately 30 minutes; Add 75 μL (equal to the half volume of culture medium present in each well) CellTiter-Glo Reagent in each well. Cover plates with aluminum foil to protect from light; Mix contents for 2 minutes on an orbital shaker to induce cell lysis; Allow the plate to incubate at room temperature for 10 minutes to stabilize luminescent signal; and Transfer the mixture of cell and CTG buffer to the detection 96 well plate and record luminescence on the 2104 EnVision plate reader. An ATP standard curve at the same time points is prepared.

Inhibition rate (IR) of the tested compounds was determined by the following formula: IR (%)=(1−(RLU compound−RLU blank)/(RLU control−RLU blank))*100%. The inhibitions of different dose of compound were calculated in Excel file, and then were used to plot inhibition curve and evaluate related parameters, such as Min, Max and IC50. The data were interpreted by GraphPad Prism software. Table 5 shows the summary of the antiproliferation results of the cell viability assay. The data shows that Compound 1 and Compound 121 have an effectiveness similar to Dasatinib, which is an accepted and widely used as a treatment of cancers.

TABLE 5

The compound IC50 values in Anti-proliferation assay.

| | Time point | | | | | |
|---|---|---|---|---|---|---|
| | Day 3 | | | Day 6 | | |
| Compound ID | Compound 1 | Compound 121 | Dasatinib | Compound 1 | Compound 121 | Dasatinib |
| Min (%) | −8.75 | −11.42 | 8.00 | −27.04 | −18.96 | 14.03 |
| Max (%) | 2.56 | 49.93 | 66.18 | 2.88 | 51.14 | 89.06 |
| IC50 (μM) | >30 | >30 | 22.35 | >30 | 29.12 | 15.15 |

Pancreatic Cancer

Compound 1 is compared to Gemcitabine, which is a chemotherapy drug used in various types of cancers (e.g., breast cancer, ovarian cancer, non-small cell lung cancer, pancreatic cancer, and bladder cancer). The compounds, at 30 μM, 3 fold serial dilution, are tested in primary tumor cells freshly isolated from PC-07-0024 and LU-01-0523 patient derived xenograft (PDX) tumor model using tumor chemosensitivity assay (TCA).

The study was performed as follows. Add 195 μL of assay medium into each well of the V-bottom plate; then transfer 5 μL of the stock compound solution of each concentration from the stock plate (400× stock). Add 5 μL of DMSO into the Blank and Control wells. Pipette up and down to mix well. This V-plate is designated as the 10× concentrate compound plate.

For cell viability test, add compounds as below. Then incubate the plates at 37° C., 5% CO2, 95% air and 100% relative humidity for 3 days or 6 days. For day 0 plate, add 15 μL of the DMSO-medium into the Control wells. The final DMSO concentration was 0.25%. Proceed to cell viability assay. For TCA plates, add 15 μL of the compound-medium from the 10× concentrate compound plate into the cells in 96-well assay plate according to the plate map. Add 15 μL of the DMSO-medium into the Blank and Control wells. The final DMSO concentration was 0.25%. The assay is performed similar to the protocol of the bile duct cancer study provided above.

Table 6 shows the summary of the antiproliferation results of the cell viability assay. The data shows that Compound 1 has an effectiveness similar to Gemcitabine, which is an accepted and widely used as a treatment of cancers.

TABLE 6

The compound IC50 values in Anti-proliferation assay.

| | Cell Line | | | | | | | | |
|---|---|---|---|---|---|---|---|---|---|
| | PC-07-0024 | | | | | LU-01-0523 | | | |
| | Day 3 | | Day 6 | | | Day 3 | | Day 6 | |
| | Compound ID | | | | | | | | |
| | Cmpnd 1 | Gemcitabine | Cmpnd 1 | Gemcitabine | Gemcitabine (data exclsn) | Cmpnd 1 | Gemcitabine | Cmpnd 1 | Gemcitabine |
| Bottom (%) | −11.36 | 10.21 | −26.68 | 23.38 | 0.00 | −5.49 | 4.79 | −16.14 | 0.00 |
| Top (%) | 42.29 | 46.53 | 37.60 | 72.30 | 30.34 | 100.00 | 100.00 | 0.00 | 100.00 |
| Relative IC50 (μM) | 5.70 | 4.00 | 2.65 | 5.93 | 0.009 | >30 | >30 | >30 | 1.34 |

Expected Results

Based on information obtained from Compound 1 and Compound 121 and on reasonably expected results in further experiments, the inventors believe that the compounds recited herein, such as Compounds 2-220 will have a prophetic activity of IC50<10 μM against relevant kinases, such as the receptor tyrosine kinases (RTK) recited herein (e.g., DDR1), and potentially other kinases. Thus, it is expected that the compounds of the formulae presented herein, such as the specific examples of Compounds 2-220 can be active in modulating kinases, such as RTK (e.g., DDR1).

ABBREVIATIONS

DMF dimethylformamide.

DMSO dimethylsulphoxide.

HPLC high performance liquid chromatography.

THF tetrahydrofuran.

TFA trifluoroacetic acid.

TLC thin layer chromatography.

TFA trifluoroacetic acid.

HATU 1-[Bis(dimethylamino)methylene]-1H-1,2,3-triazolo[4,5-b]pyridinium 3-oxid hexafluorophosphate.

DIEA diisopropylethylamine.

NMP N-Methyl-2-pyrrolidone.

XPhos Pd G3 (2-Dicyclohexylphosphino-2',4',6'-triisopropyl-1,1'-biphenyl)[2-(2'-amino-1,1'-biphenyl)]palladium (II) methanesulfonate.

CDI 1,1'-Carbonyldiimidazole.

Definitions

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like.

Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The term "boron compound" can include any compound having boron or radical thereof, or chemical having a boron substituent. Examples of boron compounds that can be included as the R groups defined herein are boron tri alkyl or radical thereof, boron di-alkyl radical, hydrogen boron di-alkyl, hydrogen boron alkyl radical, boric acid (e.g., H3BO3 or H2BO3 radical), borax (e.g., B4Na2O7.10H2O or radical thereof), boron sodium oxide (e.g., B4Na2O7 or radical thereof), boron oxide (e.g. B2O3 or radical thereof), boron acid zinc salt, cobalt borate neodecanoate complexes, boron zinc oxide (e.g., B6Zn2O11 or radical thereof), boric acid sodium salt, perboric acid sodium salt, boron lithium oxide, ammonium boron oxide, boron silver oxide, boric acid lithium salt, boron trifluoride, boron difluoride radical, boron dihydroxy, potassium boron trifluoride, 4,4,5,5-tetramethyl-3,2-dioxaboralane, and radicals thereof. The radicals can be the R group and conjugated to the chemical scaffolds described herein.

An example boron compound includes the radical of (lose hydrogen):

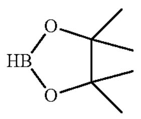

4,4,5,5-tetramethyl-1,3,2-dioxaborolane

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

All other chemistry terms are defined as known in the art.

The term "discoidin domain receptor 1" or "DDR1" as used herein refers to all isoforms and variants of the DDR1 protein, including DDR1a, DDR1b, DDR1c, DDR1d and DDR1e.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" as used herein refer to any mass of tissue that results from excessive cell growth or proliferation, either benign (noncancerous) or malignant (cancerous), including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell", "tumor stem cell", or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

As used herein "tumorigenic" refers to the functional features of a solid tumor stein cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised mouse compared to non-tumorigenic tumor cells, which are unable to form tumors upon serial transplantation. It has been observed that non-tumorigenic tumor cells may form a tumor upon primary transplantation into an immunocompromised mouse after obtaining the tumor cells from a solid tumor, but those non-tumorigenic tumor cells do not give rise to a tumor upon serial transplantation.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" and "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one DDR1 inhibitor of the present disclosure, and which does not destroy the pharmacological activity thereof and is nontoxic when administered in doses sufficient to deliver a therapeutic amount of the DDR1 inhibitor.

"Pharmaceutically acceptable vehicle" refers to a diluent, adjuvant, excipient, or carrier with which at least one DDR1 inhibitor of the present disclosure is administered.

The term "effective amount," "therapeutically effective amount" or "therapeutic effect" refers to an amount of a DDR1 inhibitor, polypeptide, polynucleotide, small organic molecule, or other drug effective to "treat" a disease or disorder in a subject or mammal. In the case of cancer, the therapeutically effective amount of the drug has a therapeutic effect and as such can reduce the number of cancer cells; decrease tumorigenicity, tumorigenic frequency or tumorigenic capacity; reduce the number or frequency of cancer stem cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; or a combination of such effects. Methods to determine tumorigenicity or tumorigenic frequency or capacity are demonstrated in copending application U.S. Ser. No. 11/776,935, incorporated by reference herein in its entirety. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder, and those in whom the disorder is to be prevented. In certain embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity; reduction in the number or frequency of cancer stem cells; or some combination of effects.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety for all that they teach. U.S. Pat. No. 8,114,874 is specifically incorporated herein for examples of substituents, treatment, and definitions.

The invention claimed is:

1. A compound having a structure of Formula A, or a salt or solvate thereof,

Formula A

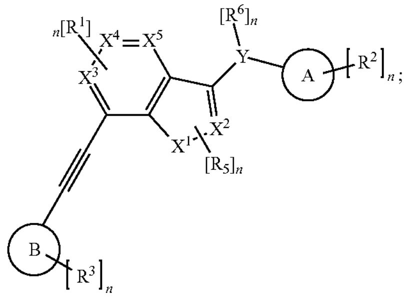

ring A is an aryl with 5-24 ring atoms, hetero aryl with 5-24 ring atoms, polyaryl with 5-24 ring atoms, or poly hetero aryl with 5-24 ring atoms;

ring B is a hetero aryl with 5-24 ring atoms, polyaryl with 5-24 ring atoms or poly hetero aryl with 5-24 ring atoms, wherein the polyaryl or poly heteroaryl comprises two or more fused aromatic or heteroaromatic rings;

$X^1$ is O or S;

$X^2$, $X^3$, $X^4$, and $X^5$ are each independently a carbon atom with or without a substituent or N;

Y is an N, S, or O linker;

each $R^1$, $R^2$, $R^3$, $R^5$, and $R^6$ is independently selected from the group of hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, thiocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, or phosphino, any with or without hetero atoms, and any substituted or unsubstituted; and each n is independently an integer, wherein $R^5$ and/or $R^6$ is optionally nothing.

2. The compound of claim 1, or a salt or solvate thereof, wherein:

ring A is a aryl with 5-12 ring atoms, hetero aryl with 5-12 ring atoms, polyaryl with 5-12 ring atoms, or poly hetero aryl with 5-12 ring atoms;

ring B is a hetero aryl with 5-12 ring atoms, polyaryl with 5-12 ring atoms, or poly hetero aryl with 5-12 ring atoms;

$X^1$ is O;

$X^2$ is N;

$X^3$, $X^4$, and $X^5$ are each independently CH or N;

Y is an O, or N linker; and $R^1$, $R^2$, $R^3$, $R^5$, and $R^6$ are each independently selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino, any with or without hetero atoms, and any substituted or unsubstituted, wherein $R^5$ and/or $R^6$ is optionally nothing.

3. The compound of claim 1, or a salt or solvate thereof, wherein:

ring A is Formula Ring A, where each X ring atom is a carbon atom with or without a substituent or N; and m is an integer, and n is an integer, Formula Ring A

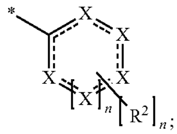

ring B is Formula Fused Ring B1, Formula Fused Ring B2, Formula Ring B3, or Formula Fused Ring B4, wherein each X ring atom is a carbon atom with or without a substituent or N, wherein each X ring atom is optionally substituted with a substituent defined by $R^3$, Formula Fused Ring B1

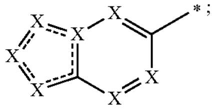

Formula Fused Ring B2

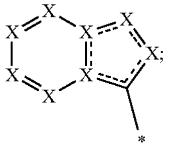

Formula Ring B3

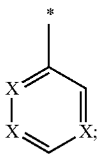

Formula Fused Ring B4

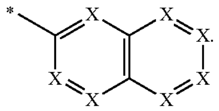

4. The compound of claim 3, or a salt or solvate thereof, wherein Formula Ring A is one of the following structures:

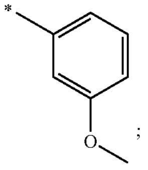

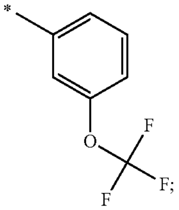

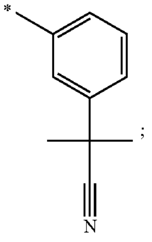

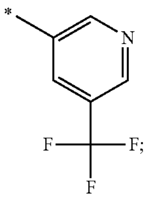

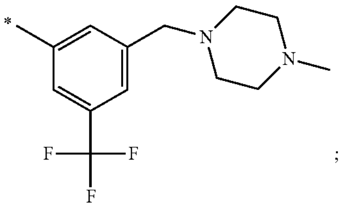

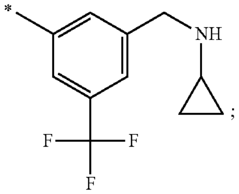

-continued

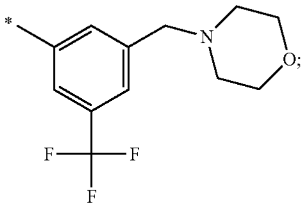

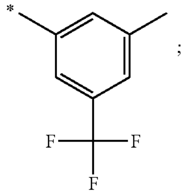

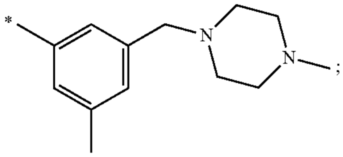

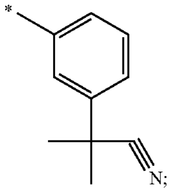

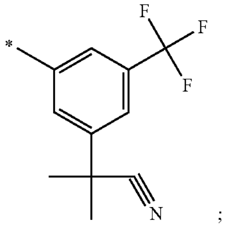

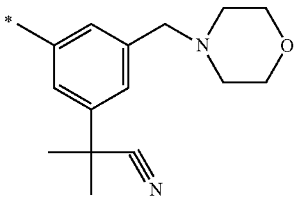

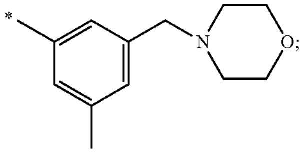

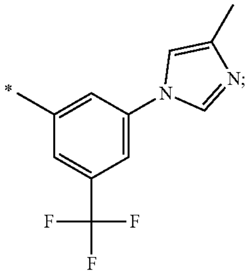

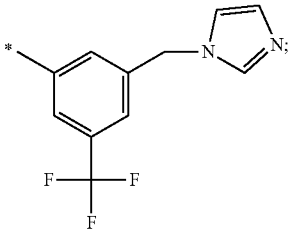

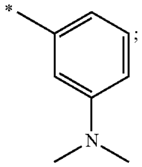

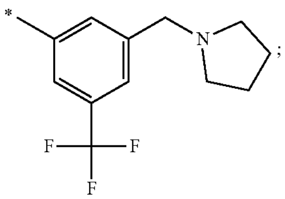

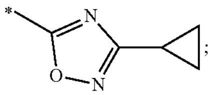

-continued

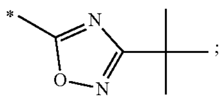

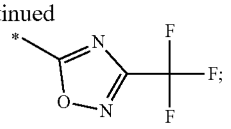

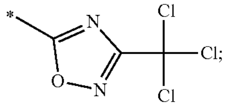

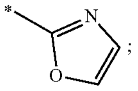

or

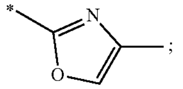

wherein Formula Fused Ring B1 is one of the following structures:

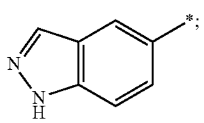

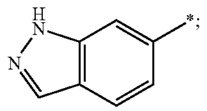

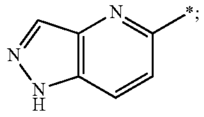

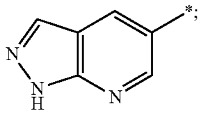

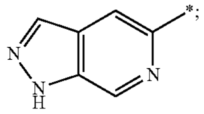

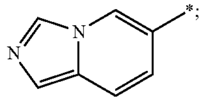

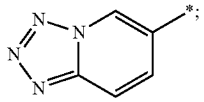

or

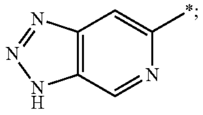

wherein Formula Fused Ring B2 is one of the following structures:

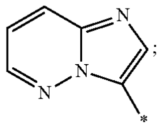

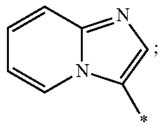

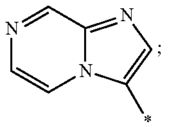

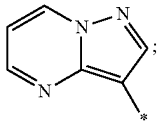

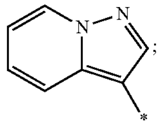

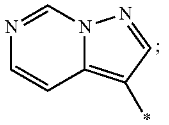

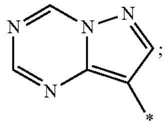

or

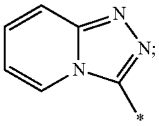

wherein Formula Ring B3 is one of the following structures:

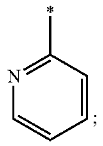

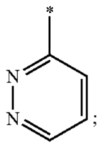

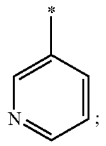

or

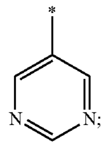

and wherein Formula Fused Ring B4 is one of the following structures:

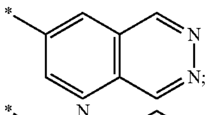

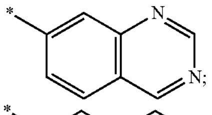

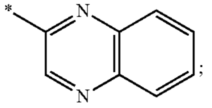

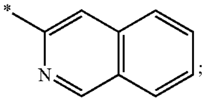

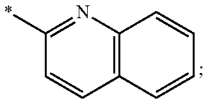

or

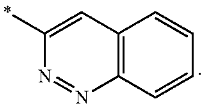

5. A compound having the structure of Formula H, or a salt or solvate thereof,

Formula H

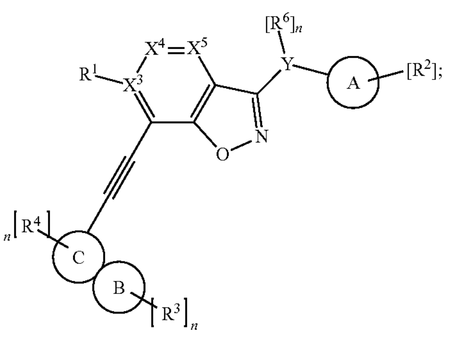

ring A is an aryl with 5-24 ring atoms, hetero aryl with 5-24 ring atoms, polyaryl with 5-24 ring atoms, or poly hetero aryl with 5-24 ring atoms;

ring B is an aryl with 5-12 ring atoms, or hetero aryl with 5-12 ring atoms;

ring C is a ring structure fused with ring B;

$X^3$ is a carbon atom;

$X^4$ and $X^5$ are each independently CH or N;

Y is an O, S, or N linker; and each $R^1$, $R^2$, $R^3$, $R^4$, and $R^6$ is independently selected from the group of hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, thiocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, or phosphino, any with or without hetero atoms, and any substituted or unsubstituted, and each n is independently an integer, wherein $R^6$ is optionally nothing.

6. The compound of claim 5, or a salt or solvate thereof, wherein:

ring A is an aryl with 5-12 ring atoms, hetero aryl with 5-12 ring atoms, polyaryl with 5-12 ring atoms, or poly hetero aryl with 5-12 ring atoms;

ring B is an aryl with 5-12 ring atoms, or hetero aryl with 5-12 ring atoms;

ring C is an aryl with 5-12 ring atoms, or hetero aryl with 5-12 ring atoms;

$X^3$ is a carbon atom;

$X^4$ and $X^5$ are each independently CH or N;

Y is a O, S, or N linker; and $R^1$, $R^2$, $R^3$, $R^4$, and $R^6$ are each independently selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, any with or without hetero atoms, and any substituted or unsubstituted, wherein $R^6$ is optionally nothing.

7. The compound of claim 5, or a salt or solvate thereof, wherein:

ring A is Formula Ring A, where each X ring atom is a carbon atom with or without a substituent or N; m is an integer and n is an integer, Formula Ring A

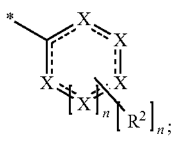

the combination of ring B fused with ring C is Formula Fused Ring B1, Formula Fused Ring B2 or Formula Fused Ring B4, wherein each X ring atom is a carbon atom with or without a substituent or N, wherein each X ring atom is optionally substituted with a substituent defined by $R^3$, Formula Fused Ring B1

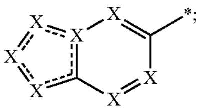

Formula Fused Ring B2

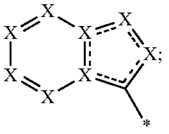

Formula Fused Ring B4

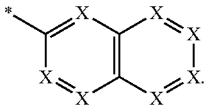

8. The compound of claim 7, or a pharmaceutically acceptable salt or solvate thereof, wherein Formula Ring A is one of the following structures:

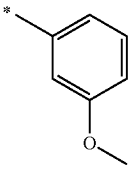
;
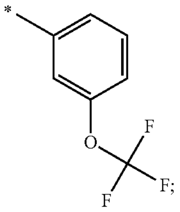
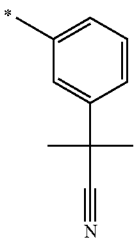
;
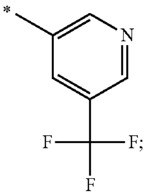
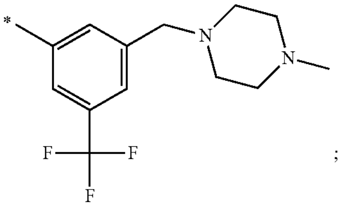
;
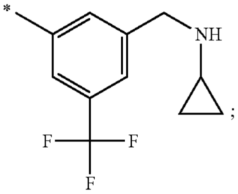
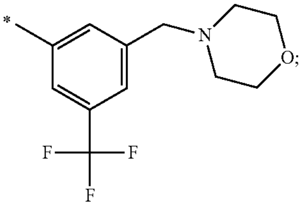
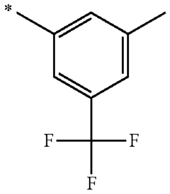
;
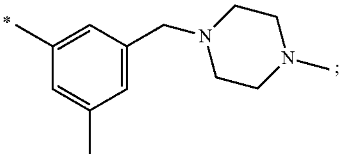

-continued

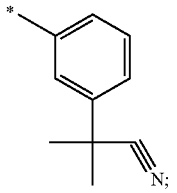
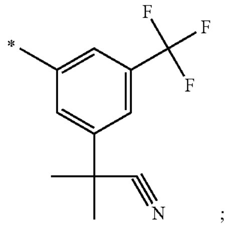
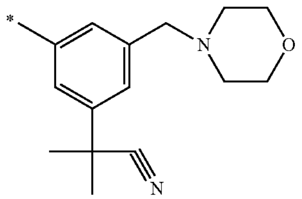
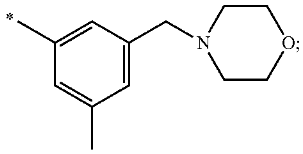
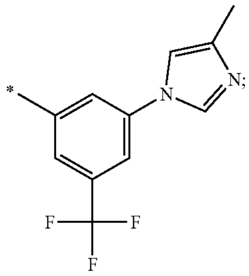
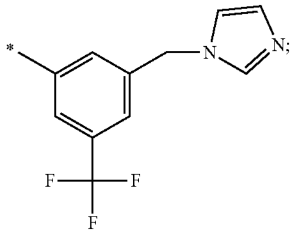
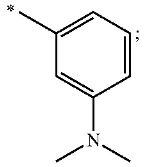
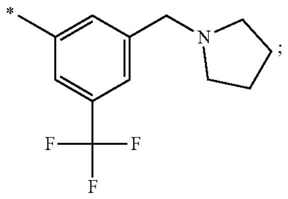
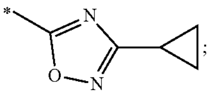
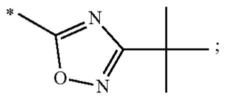
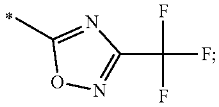
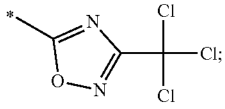
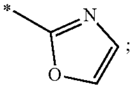
or
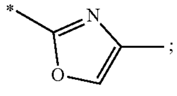

wherein Formula Fused Ring B1 is one of the following structures:

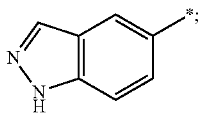
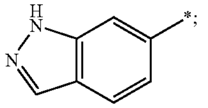
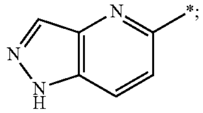
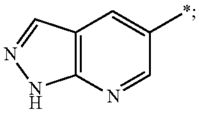
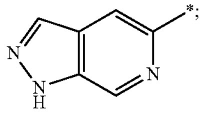
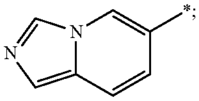
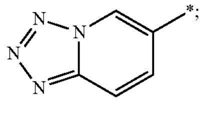
or
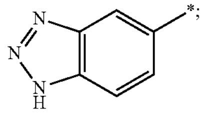

wherein Formula Fused Ring B2 is one of the following structures:

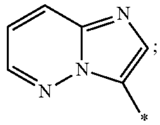
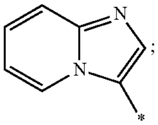
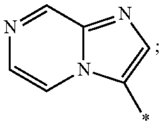
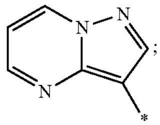
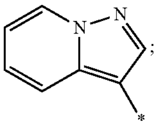
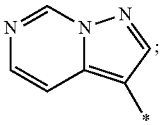
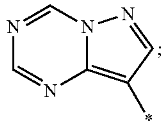
or
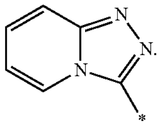

wherein Formula Fused Ring B4 is one of the following structures:

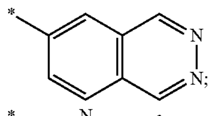
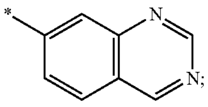
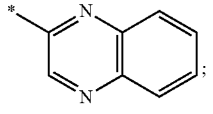
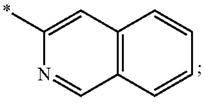
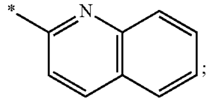
or
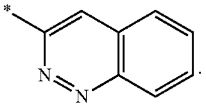

9. The compound of claim 1, wherein the compound has a structure selected from the group consisting of Formula 1, Formula 2, Formula 4, Formula 5, Formula 6, or Formula 8, or a salt or solvate thereof, Formula 1

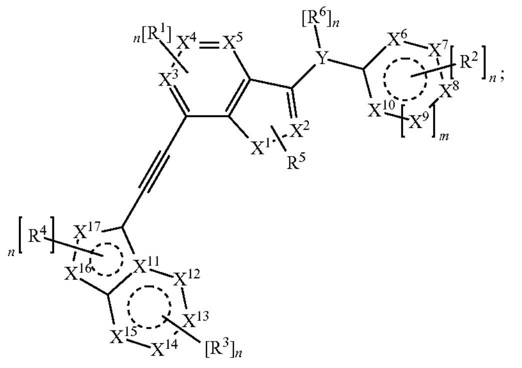

Formula 2

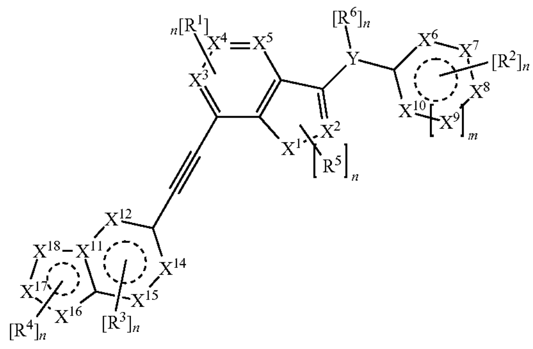

Formula 4

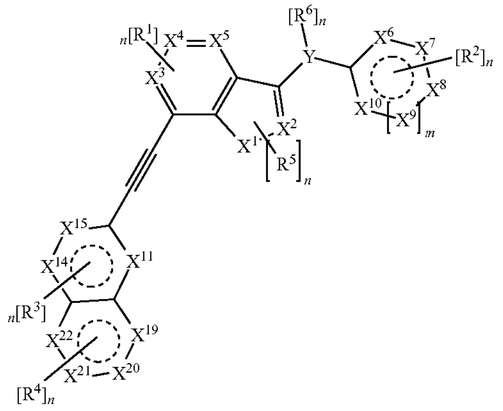

Formula 5

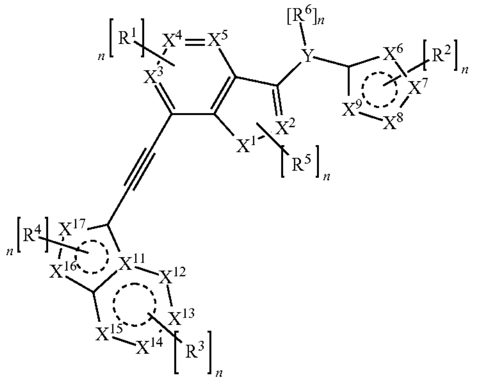

-continued

Formula 6

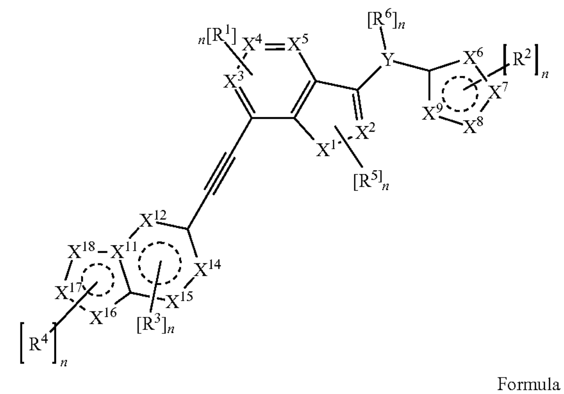

Formula 8

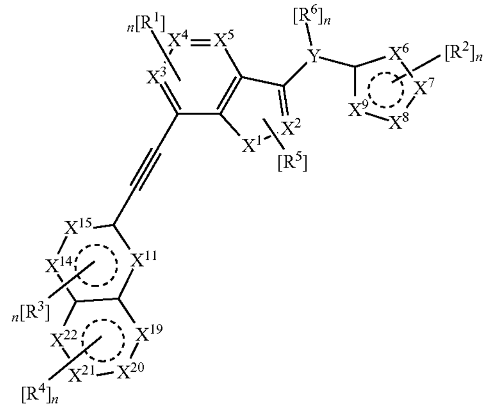

$X^1$ is O or S;

$X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ are each independently a carbon atom with or without a substituent or N;

Y is an O, S, or N linker;

n is an integer;

m is an integer; and each $R^1$, $R^2$, $R^3$, $R^4$, $R^5$, and $R^6$ is independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, thiocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, or phosphino, any with or without hetero atoms, and any substituted or unsubstituted, wherein $R^5$ and/or $R^6$ is optionally nothing.

10. The compound of claim 9, or a salt or solvate thereof, wherein:

$X^1$ is O;

$X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ are each independently CH or N;

Y is an O or N linker; and $R^1$, $R^2$, $R^3$, $R^4$, $R^5$, and $R^6$ are each independently selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, and phosphino, and any with or without hetero atoms, wherein $R^5$ and/or $R^6$ is optionally nothing.

11. The compound of claim 1 having the structure of one of compounds:

7-(imidazo[1,2-b]pyridazin-3-ylethynyl)-6-methyl-N-(3-(trifluoromethyl)phenyl)benzo[d]isoxazol-3-amine (Compound 1);

7-(imidazo[1,2-b]pyridazin-3-ylethynyl)-6-methyl-N-(3-(tribromomethyl)phenyl)benzo[d]isoxazol-3-amine (Compound 2);

6-ethyl-7-(imidazo[1,2-b]pyridazin-3-ylethynyl)-N-(3-(trifluoromethyl)phenyl)benzo[d]isoxazol-3-amine (Compound 3);

7-(imidazo[1,2-b]pyridazin-3-ylethynyl)-6-methoxy-N-(3-(trifluoromethyl)phenyl)benzo[d]isoxazol-3-amine (Compound 4);

7-(imidazo[1,2-b]pyridazin-3-ylethynyl)-6-methoxy-N-(3-(trichloromethyl)phenyl)benzo[d]isoxazol-3-amine (Compound 5);

7-(imidazo[1,2-b]pyridazin-3-ylethynyl)-6-methyl-N-(3-(trichloromethyl)phenyl)benzo[d]isoxazol-3-amine (Compound 6);

7-(imidazo[1,2-b]pyridazin-3-ylethynyl)-N-(3-(trifluoromethyl)phenyl)benzo[d]isoxazol-3-amine (Compound 7);

7-(imidazo[1,2-b]pyridazin-3-ylethynyl)-6-methyl-N-(3-(2,2,2-trifluoroethyl)phenyl)benzo[d]isoxazol-3-amine (Compound 8);

7-(imidazo[1,2-b]pyridazin-3-ylethynyl)-5-methyl-N-(3-(trifluoromethyl)phenyl)benzo[d]isoxazol-3-amine (Compound 9);

7-(imidazo[1,2-b]pyridazin-3-ylethynyl)-4-methyl-N-(3-(trifluoromethyl)phenyl)benzo[d]isoxazol-3-amine (Compound 10);

7-(imidazo[1,2-b]pyridazin-3-ylethynyl)-4,6-dimethyl-N-(3-(trifluoromethyl)phenyl)benzo[d]isoxazol-3-amine (Compound 11);

7-(imidazo[1,2-b]pyridazin-3-ylethynyl)-4,5-dimethyl-N-(3-(trifluoromethyl)phenyl)benzo[d]isoxazol-3-amine (Compound 12);

7-(imidazo[1,2-b]pyridazin-3-ylethynyl)-6-methyl-N-(2-(trifluoromethyl)phenyl)benzo[d]isoxazol-3-amine (Compound 13);

7-(imidazo[1,2-b]pyridazin-3-ylethynyl)-6-methyl-N-(4-(trifluoromethyl)phenyl)benzo[d]isoxazol-3-amine (Compound 14);

7-(imidazo[1,2-b]pyridazin-3-ylethynyl)-4,5,6-trimethyl-N-(3-(trifluoromethyl)phenyl)benzo[d]isoxazol-3-amine (Compound 15);

6-(tert-butyl)-7-(imidazo[1,2-b]pyridazin-3-ylethynyl)-N-(3-(trifluoromethyl)phenyl)benzo[d]isoxazol-3-amine (Compound 16);

5-ethyl-7-(imidazo[1,2-b]pyridazin-3-ylethynyl)-N-(3-(trifluoromethyl)phenyl)benzo[d]isoxazol-3-amine (Compound 17);

7-(imidazo[1,2-b]pyridazin-3-ylethynyl)-N3-(3-(trifluoromethyl)phenyl)benzo[d]isoxazole-3,6-diamine (Compound 18);

7-(imidazo[1,2-b]pyridazin-3-ylethynyl)-N6,N6-dimethyl-N3-(3-(trifluoromethyl)phenyl)benzo[d]isoxazole-3,6-diamine (Compound 19);

7-(imidazo[1,2-b]pyridazin-3-ylethynyl)-6-phenyl-N-(3-(trifluoromethyl)phenyl)benzo[d]isoxazol-3-amine (Compound 20);

N-([1,1'-biphenyl]-3-yl)-7-(imidazo[1,2-b]pyridazin-3-ylethynyl)-6-methylbenzo[d]isoxazol-3-amine (Compound 21);

7-((1H-indazol-5-yl)ethynyl)-6-methyl-N-(3-(trifluoromethyl)phenyl)benzo[d]isoxazol-3-amine (Compound 22);

7-((1H-indazol-6-yl)ethynyl)-6-methyl-N-(3-(trifluoromethyl)phenyl)benzo[d]isoxazol-3-amine (Compound 23);

7-((1H-pyrazolo[4,3-b]pyridin-5-yl)ethynyl)-6-methyl-N-(3-(trifluoromethyl)phenyl)benzo[d]isoxazol-3-amine (Compound 24);

7-((1H-pyrazolo[3,4-b]pyridin-5-yl)ethynyl)-6-methyl-N-(3-(trifluoromethyl)phenyl)benzo[d]isoxazol-3-amine (Compound 25);

7-((1H-pyrazolo[3,4-c]pyridin-5-yl)ethynyl)-6-methyl-N-(3-(trifluoromethyl)phenyl)benzo[d]isoxazol-3-amine (Compound 26);

7-(imidazo[1,5-a]pyridin-6-ylethynyl)-6-methyl-N-(3-(trifluoromethyl)phenyl)benzo[d]isoxazol-3-amine (Compound 27);

6-methyl-7-(tetrazolo[1,5-a]pyridin-6-ylethynyl)-N-(3-(trifluoromethyl)phenyl)benzo[d]isoxazol-3-amine (Compound 28);

7-((1H-benzo[d][1,2,3]triazol-5-yl)ethynyl)-6-methyl-N-(3-(trifluoromethyl)phenyl)benzo[d]isoxazol-3-amine (Compound 29);

7-(imidazo[1,2-a]pyridin-3-ylethynyl)-6-methyl-N-(3-(trifluoromethyl)phenyl)benzo[d]isoxazol-3-amine (Compound 30);

7-(imidazo[1,2-a]pyrazin-3-ylethynyl)-6-methyl-N-(3-(trifluoromethyl)phenyl)benzo[d]isoxazol-3-amine (Compound 31);

6-methyl-7-(pyrazolo[1,5-a]pyrimidin-3-ylethynyl)-N-(3-(trifluoromethyl)phenyl)benzo[d]isoxazol-3-amine (Compound 32);

6-methyl-7-(pyrazolo[1,5-a]pyridin-3-ylethynyl)-N-(3-(trifluoromethyl)phenyl)benzo[d]isoxazol-3-amine (Compound 33);

6-methyl-7-(pyrazolo[1,5-c]pyrimidin-3-ylethynyl)-N-(3-(trifluoromethyl)phenyl)benzo[d]isoxazol-3-amine (Compound 34);

6-methyl-7-(pyrazolo[1,5-a][1,3,5]triazin-8-ylethynyl)-N-(3-(trifluoromethyl)phenyl)benzo[d]isoxazol-3-amine (Compound 35);

7-([1,2,4]triazolo[4,3-a]pyridin-3-ylethynyl)-6-methyl-N-(3-(trifluoromethyl)phenyl)benzo[d]isoxazol-3-amine (Compound 36);

6-methyl-7-(pyridin-2-ylethynyl)-N-(3-(trifluoromethyl)phenyl)benzo[d]isoxazol-3-amine (Compound 37);

6-methyl-7-(pyridazin-3-ylethynyl)-N-(3-(trifluoromethyl)phenyl)benzo[d]isoxazol-3-amine (Compound 38);

6-methyl-7-(pyridin-3-ylethynyl)-N-(3-(trifluoromethyl)phenyl)benzo[d]isoxazol-3-amine (Compound 39);

6-methyl-7-(pyrimidin-5-ylethynyl)-N-(3-(trifluoromethyl)phenyl)benzo[d]isoxazol-3-amine (Compound 40);

6-methyl-7-(phthalazin-6-ylethynyl)-N-(3-(trifluoromethyl)phenyl)benzo[d]isoxazol-3-amine (Compound 41);

6-methyl-7-(quinazolin-7-ylethynyl)-N-(3-(trifluoromethyl)phenyl)benzo[d]isoxazol-3-amine (Compound 42);

7-(cinnolin-3-ylethynyl)-6-methyl-N-(3-(trifluoromethyl)phenyl)benzo[d]isoxazol-3-amine (Compound 43);

7-((1H-indazol-5-yl)ethynyl)-N-(3-methoxyphenyl)-6-methylbenzo[d]isoxazol-3-amine (Compound 44);

7-((1H-indazol-6-yl)ethynyl)-6-methyl-N-(3-(trifluoromethoxy)phenyl)benzo[d]isoxazol-3-amine (Compound 45);

2-(3-((7-((1H-pyrazolo[4,3-b]pyridin-5-yl)ethynyl)-6-methylbenzo[d]isoxazol-3-yl)amino)phenyl)-2-methylpropanenitrile (Compound 46);

7-((1H-pyrazolo[3,4-b]pyridin-5-yl)ethynyl)-6-methyl-N-(5-(trifluoromethyl)pyridin-3-yl)benzo[d]isoxazol-3-amine (Compound 47);

7-((1H-pyrazolo[3,4-c]pyridin-5-yl)ethynyl)-6-methyl-N-(3-((4-methylpiperazin-1-yl)methyl)-5-(trifluoromethyl)phenyl)benzo[d]isoxazol-3-amine (Compound 48);

7-(imidazo[1,5-a]pyridin-6-ylethynyl)-6-methyl-N-(3-(morpholinomethyl)-5-(trifluoromethyl)phenyl)benzo[d]isoxazol-3-amine (Compound 49);

6-methyl-N-(3-methyl-5-(trifluoromethyl)phenyl)-7-(tetrazolo[1,5-a]pyridin-6-ylethynyl)benzo[d]isoxazol-3-amine (Compound 50);

7-((1H-benzo[d][1,2,3]triazol-5-yl)ethynyl)-6-methyl-N-(3-methyl-5-(4-methylpiperazin-1-yl)methyl)phenyl)benzo[d]isoxazol-3-amine (Compound 51);

7-(imidazo[1,2-a]pyridin-3-ylethynyl)-6-methyl-N-(3-methyl-5-(morpholinomethyl)phenyl)benzo[d]isoxazol-3-amine (Compound 52);

7-(imidazo[1,2-a]pyrazin-3-ylethynyl)-6-methyl-N-(3-(4-methyl-1H-imidazol-1-yl)-5 (trifluoromethyl)phenyl)benzo[d]isoxazol-3-amine (Compound 53);

$N^1$,$N^1$-dimethyl-$N^3$-(6-methyl-7-(pyrazolo[1,5-a]pyrimidin-3-ylethynyl)benzo[d]isoxazol-3-yl)benzene-1,3-diamine (Compound 54);

6-methyl-7-(pyrazolo[1,5-a]pyridin-3-ylethynyl)-N-(3-(pyrrolidin-1-ylmethyl)-5-(trifluoromethyl)phenyl)benzo[d]isoxazol-3-amine (Compound 55);

N-(3-cyclopropyl-1,2,4-oxadiazol-5-yl)-6-methyl-7-(pyrazolo[1,5-c]pyrimidin-3-ylethynyl)benzo[d]isoxazol-3-amine (Compound 56);

N-(3-(tert-butyl)-1,2,4-oxadiazol-5-yl)-6-methyl-7-(pyrazolo[1,5-a][1,3,5]triazin-8-ylethynyl)benzo[d]isoxazol-3-amine (Compound 57);

7-([1,2,4]triazolo[4,3-a]pyridin-3-ylethynyl)-6-methyl-N-(3-(trifluoromethyl)-1,2,4-oxadiazol-5-yl)benzo[d]isoxazol-3-amine (Compound 58);

6-methyl-7-(pyridin-2-ylethynyl)-N-(3-(trichloromethyl)-1,2,4-oxadiazol-5-yl)benzo[d]isoxazol-3-amine (Compound 59);

6-methyl-N-(oxazol-2-yl)-7-(pyridazin-3-ylethynyl)benzo[d]isoxazol-3-amine (Compound 60);

6-methyl-N-(4-methyloxazol-2-yl)-7-(pyridin-3-ylethynyl)benzo[d]isoxazol-3-amine (Compound 61);

6-methyl-N-(3-(morpholinomethyl)-5-(trifluoromethyl)phenyl)-7-(pyrimidin-5-ylethynyl)benzo[d]isoxazol-3-amine (Compound 62);

6-methyl-N-(3-(morpholinomethyl)-5-(trifluoromethyl)phenyl)-7-(phthalazin-6-ylethynyl)benzo[d]isoxazol-3-amine (Compound 63);

6-methyl-N-(3-methyl-5-(morpholinomethyl)phenyl)-7-(quinazolin-7-ylethynyl)benzo[d]isoxazol-3-amine (Compound 64);

$N^1$-(7-(cinnolin-3-ylethynyl)-6-methylbenzo[d]isoxazol-3-yl)-$N^3$,$N^3$-dimethylbenzene-1,3-diamine (Compound 65);

7-((1H-indazol-5-yl)ethynyl)-N-(3-methoxyphenyl)-6-methylbenzo[d]isoxazol-3-amine (Compound 66);

7-((1H-indazol-6-yl)ethynyl)-6-methyl-N-(3-(trifluoromethoxy)phenyl)benzo[d]isoxazol-3-amine (Compound 67);

2-(3-((7-((1H-pyrazolo[4,3-b]pyridin-5-yl)ethynyl)-6-methylbenzo[d]isoxazol-3-yl)amino)phenyl)-2-methylpropanenitrile (Compound 68);

7-((1H-pyrazolo[3,4-b]pyridin-5-yl)ethynyl)-6-methyl-N-(5-(trifluoromethyl)pyridin-3-yl)benzo[d]isoxazol-3-amine (Compound 69)

7-((1H-pyrazolo[3,4-c]pyridin-5-yl)ethynyl)-6-methyl-N-(3-((4-methylpiperazin-1-yl)methyl)-5-(trifluoromethyl)phenyl)benzo[d]isoxazol-3-amine (Compound 70);

7-(imidazo[1,5-a]pyridin-6-ylethynyl)-6-methyl-N-(3-(morpholinomethyl)-5-(trifluoromethyl)phenyl)benzo[d]isoxazol-3-amine (Compound 71);

6-methyl-N-(3-methyl-5-(trifluoromethyl)phenyl)-7-(tetrazolo[1,5-a]pyridin-6-ylethynyl)benzo[d]isoxazol-3-amine (Compound 72);

7-((1H-benzo[d][1,2,3]triazol-5-yl)ethynyl)-6-methyl-N-(3-methyl-5-(4-methylpiperazin-1-yl)methyl)phenyl)benzo[d]isoxazol-3-amine (Compound 73);

7-(imidazo[1,2-a]pyridin-3-ylethynyl)-6-methyl-N-(3-methyl-5-(morpholinomethyl)phenyl)benzo[d]isoxazol-3-amine (Compound 74);

7-(imidazo[1,2-a]pyrazin-3-ylethynyl)-6-methyl-N-(3-(4-methyl-1H-imidazol-1-yl)-5-(trifluoromethyl)phenyl)benzo[d]isoxazol-3-amine (Compound 75);

$N^1$-,$N^1$-dimethyl-$N^3$-(6-methyl-7-(pyrazolo[1,5-a]pyrimidin-3-ylethynyl)benzo[d]isoxazol-3-yl)benzene-1,3-diamine (Compound 76);

6-methyl-7-(pyrazolo[1,5-a]pyridin-3-ylethynyl)-N-(3-(pyrrolidin-1-ylmethyl)-5-(trifluoromethyl)phenyl)benzo[d]isoxazol-3-amine (Compound 77);

N-(3-cyclopropyl-1,2,4-oxadiazol-5-yl)-6-methyl-7-(pyrazolo[1,5-c]pyrimidin-3-ylethynyl)benzo[d]isoxazol-3-amine (Compound 78);

N-(3-(tert-butyl)-1,2,4-oxadiazol-5-yl)-6-methyl-7-(pyrazolo[1,5-a][1,3,5]triazin-8-ylethynyl)benzo[d]isoxazol-3-amine (Compound 79);

7-([1,2,4]triazolo[4,3-a]pyridin-3-ylethynyl)-6-methyl-N-(3-(trifluoromethyl)-1,2,4-oxadiazol-5-yl)benzo[d]isoxazol-3-amine (Compound 80);

6-methyl-7-(pyridin-2-ylethynyl)-N-(3-(trichloromethyl)-1,2,4-oxadiazol-5-yl)benzo[d]isoxazol-3-amine (Compound 81);

6-methyl-N-(oxazol-2-yl)-7-(pyridazin-3-ylethynyl)benzo[d]isoxazol-3-amine (Compound 82);

6-methyl-N-(4-methyloxazol-2-yl)-7-(pyridin-3-ylethynyl)benzo[d]isoxazol-3-amine (Compound 83);

6-methyl-N-(3-(morpholinomethyl)-5-(trifluoromethyl)phenyl)-7-(pyrimidin-5-ylethynyl)benzo[d]isoxazol-3-amine (Compound 84);

6-methyl-N-(3-(morpholinomethyl)-5-(trifluoromethyl)phenyl)-7-(phthalazin-6-ylethynyl)benzo[d]isoxazol-3-amine (Compound 85);

6-methyl-N-(3-methyl-5-(morpholinomethyl)phenyl)-7-(quinazolin-7-ylethynyl)benzo[d]isoxazol-3-amine (Compound 86);

$N^1$-(7-(cinnolin-3-ylethynyl)-6-methylbenzo[d]isoxazol-3-yl)-$N^3$,$N^3$-dimethylbenzene-1,3-diamine (Compound 87);

7-((1H-indazol-5-yl)ethynyl)-N-(3-methoxyphenyl)-6-methylisoxazolo[4,5-c]pyridin-3-amine (Compound 88);

7-((1H-indazol-6-yl)ethynyl)-4,6-dimethyl-N-(3-(trifluoromethoxy)phenyl)isoxazolo[4,5-c]pyridin-3-amine (Compound 89);

2-(3-((7-((1H-pyrazolo[4,3-b]pyridin-5-yl)ethynyl)-4,5,6-trimethylbenzofuran-3-yl)amino)phenyl)-2-methylpropanenitrile (Compound 90);

7-((1H-pyrazolo[3,4-b]pyridin-5-yl)ethynyl)-6-methoxy-N-(5-(trifluoromethyl)pyridin-3-yl)furo[3,2-c]pyridin-3-amine (Compound 91);

7-((1H-pyrazolo[3,4-c]pyridin-5-yl)ethynyl)-N-(3-((4-methylpiperazin-1-yl)methyl)-5-(trifluoromethyl)phenyl)isoxazolo[4,5-d]pyrimidin-3-amine (Compound 92);

7-(imidazo[1,5-a]pyridin-6-ylethynyl)-N-(3-(morpholinomethyl)-5-(trifluoromethyl)phenyl)-6-phenylisoxazolo[4,5-c]pyridin-3-amine (Compound 93);

$N^3$-(3-methyl-5-(trifluoromethyl)phenyl)-7-(tetrazolo[1,5-a]pyridin-6-ylethynyl)-N6-(5-(trifluoromethyl)pyridin-3-yl)isoxazolo[4,5-b]pyridine-3,6-diamine (Compound 94);

7-((1H-benzo[d][1,2,3]triazol-5-yl)ethynyl)-5-ethyl-N-(3-methyl-5-((4-methylpiperazin-1-yl)methyl)phenyl)furo[2,3-c]pyridin-3-amine (Compound 95);

7-(imidazo[1,2-a]pyridin-3-ylethynyl)-6-methyl-3-(3-methyl-5-(morpholinomethyl)phenoxy)isoxazolo[4,5-b]pyridine (Compound 96);

3-((3-cyclopropyl-1,2,4-oxadiazol-5-yl)thio)-6-methyl-7-(pyrazolo[1,5-c]pyrimidin-3-ylethynyl)benzo[d]isoxazole (Compound 100);

N-(3-(tert-butyl)-1,2,4-oxadiazol-5-yl)-6-methyl-7-(pyrazolo[1,5-a][1,3,5]triazin-8-ylethynyl)isoxazolo[4,5-c]pyridin-3-amine (Compound 101);

7-([1,2,4]triazolo[4,3-a]pyridin-3-ylethynyl)-6-methyl-N-(3-(trifluoromethyl)-1,2,4-oxadiazol-5-yl)isoxazolo[4,5-c]pyridin-3-amine (Compound 102);

6-methoxy-7-(pyridin-2-ylethynyl)-N-(3-(trichloromethyl)-1,2,4-oxadiazol-5-yl)isoxazolo[4,5-b]pyridin-3-amine (Compound 103);

6-methyl-3-(oxazol-2-yloxy)-7-(pyridazin-3-ylethynyl)isoxazolo[4,5-c]pyridine (Compound 104);

6-methyl-3-((4-methyloxazol-2-yl)oxy)-7-(pyridin-3-ylethynyl)benzo[d]isoxazole (Compound 105);

6-methyl-3-((3-(morpholinomethyl)-5-(trifluoromethyl)phenyl)thio)-7-(pyrimidin-5-ylethynyl)furo[3,2-b]pyridine (Compound 106);

7-((8-methylphthalazin-6-yl)ethynyl)-3-((3-(morpholinomethyl)-5-(trifluoromethyl)phenyl)thio)furo[3,2-c]pyridine (Compound 107);

7-((2,5-dimethyl quinazolin-7-yl)ethynyl)-6-methoxy-3-(3-methyl-5-(morpholinomethyl)phenoxy)isoxazolo[4,5-c]pyridine (Compound 108);

3-((7-((6,7-dimethylcinnolin-3-yl)ethynyl)-4-methylfuro[2,3-c]pyridin-3-yl)oxy)-N,N-dimethylaniline (Compound 109);

7-(imidazo[1,2-b]pyridazin-3-ylethynyl)-6-methyl-N-(3-((4-methylpiperazin-1-yl)methyl)-5-(trifluoromethyl)phenyl)benzo[d]isoxazol-3-amine (Compound 110)

7-(imidazo[1,2-b]pyridazin-3-ylethynyl)-6-methyl-N-(3-(morpholinomethyl)-5-(trifluoromethyl)phenyl)benzo[d]isoxazol-3-amine (Compound 111);

N-(3-((cyclopropylamino)methyl)-5-(trifluoromethyl)phenyl)-7-(imidazo[1,2-b]pyridazin-3-ylethynyl)-6-methylbenzo[d]isoxazol-3-amine (Compound 112);

7-(imidazo[1,2-b]pyridazin-3-ylethynyl)-6-methyl-N-(3-(pyrrolidin-1-ylmethyl)-5-(trifluoromethyl)phenyl)benzo[d]isoxazol-3-amine (Compound 113);

N-(3-((1H-imidazol-1-yl)methyl)-5-(trifluoromethyl)phenyl)-7-(imidazo[1,2-b]pyridazin-3-ylethynyl)-6-methylbenzo[d]isoxazol-3-amine (Compound 114);

2-(3-((7-(imidazo[1,2-b]pyridazin-3-ylethynyl)-6-methylbenzo[d]isoxazol-3-yl)amino)phenyl)-2-methylpropanenitrile (Compound 115);

2-(3-((7-(imidazo[1,2-b]pyridazin-3-ylethynyl)-6-methylbenzo[d]isoxazol-3-yl)amino)-5-(trifluoromethyl)phenyl)-2-methylpropanenitrile (Compound 116);

2-(3-((7-(imidazo[1,2-b]pyridazin-3-ylethynyl)-6-methylbenzo[d]isoxazol-3-yl)amino)-5-(morpholinomethyl)phenyl)-2-methylpropanenitrile (Compound 117);

7-(imidazo[1,2-b]pyridazin-3-ylethynyl)-6-methyl-N-(3-methyl-5-(trifluoromethyl)phenyl)benzo[d]isoxazol-3-amine (Compound 118);

7-(imidazo[1,2-b]pyridazin-3-ylethynyl)-6-methyl-N-(3-(4-methyl-1H-imidazol-1-yl)-5-(trifluoromethyl)phenyl)benzo[d]isoxazol-3-amine (Compound 119);

7-(imidazo[1,2-b]pyridazin-3-ylethynyl)-6-methyl-N-(3-(trifluoromethoxy)phenyl)benzo[d]isoxazol-3-amine (Compound 120); and 7-(imidazo[1,2-b]pyridazin-3-ylethynyl)-6-methyl-N-(5-(trifluoromethyl)pyridin-3-yl)benzo[d]isoxazol-3-amine (Compound 121); or a salt or solvate thereof.

12. The compound of claim 1 having the structure of one of compounds:

7-(imidazo[1,2-b]pyridazin-3-ylethynyl)-6-methyl-N-(3-(trifluoromethyl)phenyl)benzo[d]isoxazol-3-amine (Compound 1);

7-(imidazo[1,2-b]pyridazin-3-ylethynyl)-6-methyl-N-(3-((4-methylpiperazin-1-yl)methyl)-5-(trifluoromethyl)phenyl)benzo[d]isoxazol-3-amine (Compound 110);

7-(imidazo[1,2-b]pyridazin-3-ylethynyl)-6-methyl-N-(3-(morpholinomethyl)-5-(trifluoromethyl)phenyl)benzo[d]isoxazol-3-amine (Compound 111);

N-(3-((cyclopropylamino)methyl)-5-(trifluoromethyl)phenyl)-7-(imidazo[1,2-b]pyridazin-3-ylethynyl)-6-methylbenzo[d]isoxazol-3-amine (Compound 112);

7-(imidazo[1,2-b]pyridazin-3-ylethynyl)-6-methyl-N-(3-(pyrrolidin-1-ylmethyl)-5-(trifluoromethyl)phenyl)benzo[d]isoxazol-3-amine (Compound 113);

N-(3-((1H-imidazol-1-yl)methyl)-5-(trifluoromethyl)phenyl)-7-(imidazo[1,2-b]pyridazin-3-ylethynyl)-6-methylbenzo[d]isoxazol-3-amine (Compound 114);

2-(3-((7-(imidazo[1,2-b]pyridazin-3-ylethynyl)-6-methylbenzo[d]isoxazol-3-yl)amino)phenyl)-2-methylpropanenitrile (Compound 115);

2-(3-((7-(imidazo[1,2-b]pyridazin-3-ylethynyl)-6-methylbenzo[d]isoxazol-3-yl)amino)-5-(trifluoromethyl)phenyl)-2-methylpropanenitrile (Compound 116);

2-(3-((7-(imidazo[1,2-b]pyridazin-3-ylethynyl)-6-methylbenzo[d]isoxazol-3-yl)amino)-5-(morpholinomethyl)phenyl)-2-methylpropanenitrile (Compound 117);

7-(imidazo[1,2-b]pyridazin-3-ylethynyl)-6-methyl-N-(3-methyl-5-(trifluoromethyl)phenyl)benzo[d]isoxazol-3-amine (Compound 118);

7-(imidazo[1,2-b]pyridazin-3-ylethynyl)-6-methyl-N-(3-(4-methyl-1H-imidazol-1-yl)-5-(trifluoromethyl)phenyl)benzo[d]isoxazol-3-amine (Compound 119);

7-(imidazo[1,2-b]pyridazin-3-ylethynyl)-6-methyl-N-(3-(trifluoromethoxy)phenyl)benzo[d]isoxazol-3-amine (Compound 120); and 7-(imidazo[1,2-b]pyridazin-3-ylethynyl)-6-methyl-N-(5-(trifluoromethyl)pyridin-3-yl)benzo[d]isoxazol-3-amine (Compound 121); or a salt or solvate thereof.

13. The compound of claim 1 having the structure of Compound 1,

Compound 1

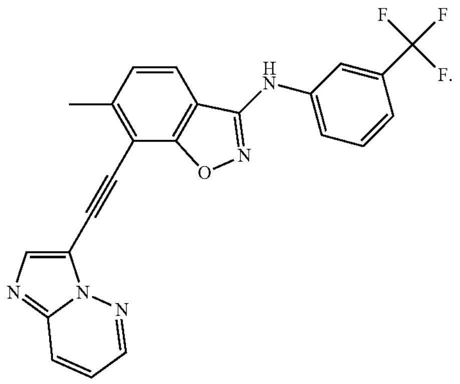

14. A pharmaceutical composition comprising:

the compound of claim 1; and a pharmaceutically acceptable carrier having the compound.

* * * * *